US006355635B1

(12) United States Patent
Elliott et al.

(10) Patent No.: US 6,355,635 B1
(45) Date of Patent: Mar. 12, 2002

(54) COMPOUNDS FOR THE TREATMENT OF OBESITY

(75) Inventors: Richard L. Elliott, East Lyme; Richard F. Hank, No. Stonington; Marlys Hammond, Salem, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/540,127

(22) Filed: Mar. 31, 2000

Related U.S. Application Data

(60) Provisional application No. 60/132,029, filed on Apr. 30, 1999.

(51) Int. Cl.[7] .................. A61K 31/5355; C07D 413/00
(52) U.S. Cl. ..................................... 514/231.5; 544/111
(58) Field of Search ........................ 514/231.5; 544/111

(56) References Cited

U.S. PATENT DOCUMENTS

| | | | |
|---|---|---|---|
| 4,440,774 A | 4/1984 | Baldwin et al. | ............. 424/267 |
| 4,853,383 A | 8/1989 | Baldwin et al. | .......... 514/235.8 |
| 5,576,337 A | 11/1996 | Bruns, Jr. et al. | ........... 514/324 |

FOREIGN PATENT DOCUMENTS

| | | |
|---|---|---|
| DE | 3935514 | 10/1989 |
| EP | 0354549 | 2/1990 |
| EP | 0448765 | 3/1990 |
| EP | 0759441 | 2/1997 |
| WO | 9614307 | 5/1996 |
| WO | 9901128 | 1/1999 |
| WO | 9948888 | 9/1999 |

OTHER PUBLICATIONS

Browne,E.J., "1,2,4–Triazole–3–ylpyridines",Aus.J.Chem. 28/11,2543–6(1975), Nov. 1975.*

James F. Flood,[*1] et. al., *Peptides*, "Dissociation of the Effects of Neuropeptide Y on Feeding and Memory: Evidence for Pre– and Postsynaptic Mediation", vol. 10, p.p. 963–966, 1989.

S. F. Leibowitz, et al., *Peptides*, "Analysis of Neuropeptide Y–Induced Feeding: Dissociation of $Y_1$ and $Y_2$ Receptor Effects on Natural Meal Patterns", vol. 12, p.p. 1251–1260, 1991.

B. G. Stanley,[*1] et al., *Peptides*, "Evidence for Neuropeptide Y Mediation of Eating Produced by Food Deprivation and for a Variant of the $Y_1$ Receptor Mediating This Peptide's Effect", vol. 13, p.p. 581–587, 1992.

Claes Wahlested[a], et al., *Regulatory Peptides*, "Evidence for different pre–and post–junctional receptors for neuropeptide Y and related peptides", vol. 13, p.p. 307–318, 1986.

Moira A. McAuley, et al., *The Journal of Pharmacology and Experimental Therapeutics*, "Possible Location and Function of Neuropeptide Y Receptor Subtypes in the Rat Mesenteric Arterial Bed[1]", vol. 261., No. 3, p.p. 863–868, 1992.

Lars Grundemar, et al., *Br. J. Pharmacol.*, "Characterization of vascular neuropeptide Y receptors", vol. 105, p.p. 45–50, 1992.

Lars Grundemar, et. al., *Tips Reviews*, "Neuropeptide Y effector systems: perspectives for drug development" vol. 15, p.p. 153–159, May 1994.

* cited by examiner

*Primary Examiner*—Mukund J. Shah
*Assistant Examiner*—Sudhaker B. Patel
(74) *Attorney, Agent, or Firm*—Peter C. Richardson; Gregg C. Benson; Arlene K. Musser

(57) ABSTRACT

NPY antagonists, methods of using such NPY antagonists and pharmaceutical compositions containing such NPY antagonists. The NPY antagonists are useful for the treatment of NPY mediated disease/conditions including obesity.

74 Claims, No Drawings

COMPOUNDS FOR THE TREATMENT OF OBESITY

This application claims priority from provisional application U.S. Ser. No. 60/132,029 filed Apr. 30,1999, the benefit of which is hereby claimed under 37 C.F.R. §1.78 (a)(3).

BACKGROUND OF INVENTION

This invention relates to NPY antagonists, particularly NPY-5 antagonists, and pharmaceutical compositions containing such antagonists and the use of such antagonists to treat, for example, obesity, feeding disorders, as well as other NPY mediated diseases/condifions in mammals, including humans, dogs, cats and horses.

Neuropeptide Y (NPY), a 36 amino acid peptide neurotransmitter, is a member of the pancreatic polypeptide class of neurotransmitters/neurohormones which has been shown to be present in both the periphery and central nervous system. NPY is one of the most potent orexogenic agents known and has been shown to play a major role in the regulation of food intake in animals. At least 6 NPY receptor subclasses have been identified and cloned to date, with two of these subclasses, NPY-1 and NPY-5, thought to be the most important receptor subtypes modulating food intake and energy expenditure.

Various animal studies have shown that activation of neuropeptide Y receptors is related to stimulation of consummatory behavior, Food and Morley *Peptides,* 10:963–966 (1989), Leibowitz and Alexander, *Peptides,* 12:1251–1260 (1991), and Stanley et al. *Peptides,* 13:581–587 (1992), and to vasoconstriction, Wahlestedt et al. *Regul. Peptides,* 13:307–318 (1986), McCauley and Westfall *J. Pharmacol. Exp. Ther.* 261:863–868 (1992), and Grundemar et al. *Br. J. Pharmacol.* 105:45–50 (1992).

Further, Grundemar and Hakanson TiPS, May 1994 [Vol.15],153–159, state that in animals, neuropeptide Y is a powerful stimulus of food intake and inducer of vasoconstriction leading to hypertension. They also point out that low levels of neuropeptide Y (NPY) are associated with loss of appetite. The reports clearly indicate that compounds that inhibit the activity of this protein will reduce hypertension and appetite in animals.

Hence, agents capable of blocking NPY binding at these receptor subtype(s) should have utility in a number of feeding disorders including obesity, anorexia nervosa, bulimia nervosa; obesity-related disorders including but not limited to insulin resistance, diabetes, hyperlipidemia, and hypertension, as well other indications for treatment where blockade of NPY activity is beneficial.

EP0759441 and U.S. Pat. No. 5,576,337 report physiological disorders related to any excess of neuropeptide Y.

In addition, a variety of publications have disclosed the use of imidazole and benzylamine derivatives for various utilities including the treatment of obesity.

WO 99/01128 discloses certain NPY5 receptor mediators useful for treating feeding disorders such as obesity and bulima as well as certain cardiovascular diseases such as essential hypertension.

WO 96/14307 describes substituted benzylamine derivatives which selectively bind to human neuropeptide Y1 receptors.

U.S. Pat. Nos. 4,440,774 and 4,853,383 disclose certain substituted imidazoles and their use as β-adrenergic blockers for the treatment of, for example, hypertension.

EP 0354549 discloses certain imidazoles which are cyan couplers useful in the photography industry.

Thus, there is clearly a need and a continuing search in this field of art for treatments for obesity.

SUMMARY OF THE INVENTION

This invention is directed to compounds of Formula I

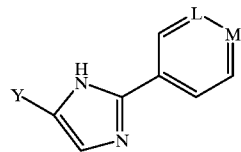

Formula 1 a prodrug thereof, or a pharmaceutically acceptable salt of said compound or of said prodrug;

wherein Y is an aromatic five to eight membered ring optionally having one to two heteroatoms selected independently from oxygen, sulfur and nitrogen or an aromatic bicyclic ring consisting of two fused three to six membered rings, taken independently, optionally having one to four heteratoms selected independently from nitrogen, sulfur and oxygen;

wherein said Y ring has a maximum of three substituents selected independently from Group I, Group II and Group III:

Group I: said Y ring is optionally mono-, di-, or tri-substituted independently with nitro, amino, hydroxy, $(C_2-C_6)$alkenyl, $(C_1-C_4)$alkylthio, halo, cyano, $(C_3-C_6)$cycloalkyl$(C_1-C_6)$alkyl, $(C_3-C_6)$cycloalkyl$(C_1-C_6)$alkyloxy,$(C_1-C_6)$alkyl, $(C_3-C_6)$cycloalkyl, $(C_1-C_6)$alkoxy or $(C_3-C_6)$cycloalkoxy, said $(C_3-C_6)$ cycloalkyl$(C_1-C_6)$alkyl, $(C_3-C_6)$cycloalkyl$(C_1-C_6)$ alkyloxy, $(C_1-C_6)$alkyl, $(C_3-C_6)$cycloalkyl, $(C_1-C_6)$ alkoxy and $(C_3-C_6)$cycloalkoxy moieties optionally substituted with one to nine fluorines;

Group II: said Y ring is optionally mono-subsfituted with a four to seven membered saturated nitrogen containing ring optionally having one to two additional heteroatoms selected independently from sulfur, oxygen or nitrogen, said four to seven membered ring optionally mono- or di-subsfituted independently with $(C_1-C_5)$ alkyl, said $(C_1-C_5)$alkyl optionally substituted with one to nine fluorines; or Group III: said Y ring is optionally mono-, or di-substituted independently with mono-N- or di-N,N-$(C_1-C_6)$alkylamino, mono-N- or di-N,N-$(C_3-C_6)$ cycloalkylamino or N-$(C_1-C_6)$alkyl-N-$(C_3-C_6)$ cycloalkylamino, said mono-N- or di-N,N-$(C_1-C_6)$ alkylamino, mono-N- or di-N,N-$(C_3-C_6)$ cycloalkylamino or N-$(C_1-C_6)$alkyl-N-$(C_3-C_6)$ cycloalkylamino optionally mono-, di-, or tri-substituted independently on each $(C_1-C_6)$alkyl or $(C_3-C_6)$cycloalkyl with $(C_3-C_6)$cycloalkyl, hydroxy, $(C_1-C_6)$alkoxy, $(C_3-C_6)$cycloalkoxy, $(C_3-C_6)$ cycloalkyl$(C_3-C_6)$alkoxy, cyano or fluoro;

L and M are each independently carbon or nitrogen, with the proviso that L and M are not the same, wherein said carbon is bonded to an $R^3$ ring through an $R^3$ ring nitrogen;

wherein $R^3$ is a four to eight membered saturated or partially saturated nitrogen containing ring optionally having one additional heteratom selected independently from sulfur, oxygen or nitrogen;

wherein said additional optional $R^3$ ring nitrogen is optionally mono-substituted with:

1) H or a T ring, optionally linked through $(C_1-C_8)$alkyl or carbonyl wherein said T ring is a partially saturated or fully unsaturated five to eight membered ring optionally having one to two heteroatoms selected independently from oxygen, sulfur and nitrogen or said T ring is a four to seven membered saturated ring having one to two heteroatoms selected independently from sulfur, oxygen or nitrogen or said T ring is an aromatic bicyclic ring consisting of two fused three to six membered rings, taken independently, optionally having one to four heteratoms selected independently from nitrogen, sulfur and oxygen;

wherein said T ring is substituted with a maximum of three substituents selected independently from Group IV, Group V and Group VI (this phase and analogous phrases used herein is exemplified as follows: there may be 3 substituents from Group IV for a total of 3 substituents, there may be 2 substituents from Group V and 1 substituent from group IV for a total of 3 substituents, etc.):

Group IV: said T ring is optionally mono-, di- or tri-substituted independently with nitro, amino, hydroxy, $(C_2-C_6)$alkenyl, $(C_1-C_4)$alkylthio, halo, cyano, $(C_1-C_6)$alkyl, $(C_3-C_6)$cycloalkyl, $(C_3-C_6)$cycloalkyl$(C_1-C_6)$alkyl, $(C_3-C_6)$cycloalkyl$(C_1-C_6)$alkyloxy, $(C_1-C_6)$alkoxy, $(C_3-C_6)$cycloalkoxy, said $(C_1-C_6)$alkyl, $(C_3-C_6)$cycloalkyl, $(C_1-C_6)$alkoxy, $(C_3-C_6)$cycloalkyl$(C_1-C_6)$alkyl, $(C_3-C_6)$cycloalkyl$(C_1-C_6)$alkyloxy and $(C_3-C_6)$cycloalkoxy moieties optionally substituted with one to nine fluorines;

Group V: said T ring optionally mono- or di-substituted independently with mono-N- or di-N,N-$(C_1-C_6)$alkylamino, mono-N- or di-N,N-$(C_3-C_6)$cycloalkylamino or N-$(C_1-C_6)$alkyl-N-$(C_3-C_6)$cycloalkylamino wherein said mono-N- or di-N,N-$(C_1-C_6)$alkylamino, mono-N- or di-N,N-$(C_3-C_6)$cycloalkylamino or N-$(C_1-C_6)$alkyl-N-$(C_3-C_6)$cycloalkylamino is optionally mono-, di-, or tri-substituted independently on each of said $(C_1-C_6)$alkyl or $(C_3-C_6)$cycloalkyl with $(C_3-C_6)$cycloalkyl, hydroxy, $(C_1-C_3)$alkoxy, $(C_3-C_6)$cycloalkoxy, $(C_3-C_6)$cycloalkyl$(C_1-C_3)$alkoxy, cyano or fluoro;

Group VI: said T ring is optionally mono-substituted with a four to seven membered saturated nitrogen containing ring optionally having one to two additional heteroatoms selected independently from sulfur, oxygen or nitrogen linked to the aromatic T ring through nitrogen, said four to seven membered ring optionally mono-substituted with $(C_1-C_5)$alkyl, said $(C_1-C_5)$alkyl optionally substituted with one to nine fluorines;

2) $(C_1-C_8)$alkyl, $(C_3-C_8)$cycloalkyl or $(C_3-C_8)$cycloalkyl$(C_1-C_8)$alkyl; wherein said $(C_1-C_8)$alkyl, $(C_3-C_8)$cycloalkyl or $(C_3-C_8)$cycloalkyl$(C_1-C_8)$alkyl is optionally substituted with one to nine fluorines and wherein said $(C_1-C_8)$alkyl, $(C_3-C_8)$cycloalkyl or $(C_3-C_8)$cycloalkyl$(C_1-C_8)$alkyl is optionally substituted with a maximum of three substituents selected independently from Group VII, Group VIII, Group IX and Group X:

Group VII: said $(C_1-C_8)$alkyl, $(C_3-C_8)$cycloalkyl or $(C_3-C_8)$cycloalkyl$(C_1-C_8)$alkyl optionally mono-, di- or tri-substituted independently with mono-N- or di-N,N-$(C_1-C_6)$alkylaminocarbonyl, mono-N- or di-N,N-$(C_3-C_6)$cycloalkylaminocarbonyl, N-$(C_1-C_6)$alkyl-N-$(C_3-C_6)$cycloalkylaminocarbonyl, carboxy, nitro, amino, hydroxy, $(C_2-C_6)$alkenyl, $(C_1-C_4)$alkylthio, halo, cyano, $(C_1-C_6)$alkyl, $(C_3-C_6)$cycloalkyl, $(C_1-C_6)$alkoxy, or $(C_3-C_6)$cycloalkoxy, said mono-N- or di-N, N-$(C_1-C_6)$alkylaminocarbonyl, mono-N- or di-N,N-$(C_3-C_6)$cycloalkylaminocarbonyl, N-$(C_1-C_6)$alkyl-N-$(C_3-C_6)$cycloalkylaminocarbonyl, $(C_1-C_6)$alkyl, $(C_1-C_6)$cycloalkyl, $(C_1-C_6)$alkoxy, and $(C_3-C_6)$cycloalkoxy moieties optionally substituted with one to nine fluorines;

Group VIII: said $(C_1-C_8)$alkyl, $(C_3-C_8)$cycloalkyl or $(C_3-C_8)$cycloalkyl$(C_1-C_8)$alkyl optionally mono-substituted with a four to seven membered saturated nitrogen containing ring, linked through a ring nitrogen, said ring optionally having one to two additional heteroatoms selected independently from suflur, oxygen or nitrogen, said four to seven membered ring optionally substituted with $(C_1-C_5)$alkyl, said $(C_1-C_5)$alkyl optionally substituted with one to nine fluorines;

Group IX: said $(C_1-C_8)$alkyl, $(C_3-C_8)$cycloalkyl or $(C_3-C_8)$cycloalkyl$(C_1-C_8)$alkyl optionally mono-, di- or tri-substituted independently with mono-N- or di-N, N-$(C_1-C_6)$alkylamino, mono-N- or di-N,N-$(C_3-C_6)$cycloalkylamino or N-$(C_1-C_6)$alkyl-N-$(C_3-C_6)$cycloalkylamino, said mono-N- or di-N,N-$(C_1-C_6)$alkylamino, mono-N- or di-N,N-$(C_3-C_6)$cycloalkylamino or N-$(C_1-C_6)$alkyl-N-$(C_3-C_6)$cycloalkylamino optionally mono-, di-, or tri-substituted independently on each $(C_1-C_6)$alkyl or $(C_3-C_6)$cycloalkyl with $(C_3-C_6)$cycloalkyl, hydroxy, $(C_1-C_3)$alkoxy, $(C_3-C_6)$cycloalkoxy, cyano, or fluoro;

Group X: said $(C_1-C_8)$alkyl, $(C_3-C_8)$cycloalkyl or $(C_3-C_8)$cycloalkyl$(C_1-C_6)$alkyl optionally mono-, di- or tri-substituted independently with $(C_1-C_6)$alkoxycarbonyl or $(C_1-$ )alkylformyl, said $(C_1-C_6)$alkoxycarbonyl or $(C_1-C_6)$alkylformyl optionally mono-, di- or tri-substituted independently with hydroxy, cyano, fluoro, $(C_1-C_6)$alkyl, $(C_1-C_6)$alkoxy, $(C_3-C_6)$cycloalkyl, $(C_3-C_6)$cycloalkyl$(C_1-C_6)$alkyl, $(C_3-C_6)$cycloalkyl$(C_1-C_6)$alkoxy or $(C_3-C_6)$cycloalkoxy said $(C_1-C_6)$alkyl, $(C_1-C_6)$alkoxy, $(C_3-C_6)$cycloalkyl, $(C_3-C_6)$cycloalkyl$(C_1-C_6)$alkyl, $(C_3-C_6)$cycloalkyl$(C_1-C_6)$alkoxy or $(C_3-C_6)$cycloalkoxy, optionally substituted with one to nine fluorines;

3) $(C_1-C_8)$alkoxycarbonyl, $(C_3-C_8)$cycloalkoxycarbonyl, $(C_3-C_8)$cycloalkyl$(C_1-C_8)$alkoxycarbonyl, $(C_1-C_8)$alkylformyl, $(C_3-C_8)$cycloalkylformyl or $(C_1-C_8)$cycloalkyl$(C_1-C_8)$alkylformyl, said $(C_1-C_8)$alkoxycarbonyl, $(C_3-C_8)$cycloalkoxycarbonyl, $(C_3-C_8)$cycloalkyl$(C_1-C_8)$alkoxycarbonyl, $(C_1-C_8)$alkylformyl, $(C_3-C_8)$cycloalkylformyl or $(C_3-C_8)$cycloalkyl$(C_1-C_8)$alkylformyl optionally mono-, di- or tri-substituted independently with hydroxy, cyano, fluoro, $(C_1-C_6)$alkoxy, $(C_1-C_6)$alkyl, $(C_3-C_6)$cycloalkyl, $(C_3-C_6)$cycloalkyl$(C_1-C_6)$alkyl, $(C_3-C_6)$cycloalkyl$(C_1-C_6)$alkoxy or $(C_3-C_6)$cycloalkoxy, said$(C_1-C_6)$alkoxy, $(C_1-C_6)$alkyl, $(C_3-C_6)$cycloalkyl, $(C_3-C_6)$cycloalkyl$(C_1-C_6)$alkyl, $(C_3-C_6)$cycloalkyl$(C_1-C_6)$alkoxy or $(C_1-C_6)$cycloalkoxy optionally substituted with from one to nine fluorines;

4) sulfonyl, said sulfonyl optionally mono-substituted with amino, hydroxy, $(C_2-C_8)$alkenyl, $(C_1-C_8)$alkyl, $(C_3-C_8)$cycloalkyl, $(C_1-C_8)$alkoxy, $(C_3-C_8)$cycloalkoxy, $(C_3-C_8)$cycloalkyl$(C_1-C_8)$alkyl or $(C_3-C_8)$cycloalkyl$(C_1-C_8)$alkyloxy said $(C_2-C_8)$alkenyl, $(C_1-C_8)$alkyl, $(C_3-C_8)$cycloalkyl, $(C_1-C_8)$alkoxy, $(C_1-C_8)$cycloalkyl$(C_1-C_8)$alkyl, $(C_3-C_8)$cycloalkyl$(C_1-C_8)$alkyloxy and $(C_1-C_8)$cycloalkoxy moieties optionally substituted with one to nine fluoros;

or said sulfonyl optionally mono-substituted with mono-N- or di-N,N-($C_1$–$C_6$)alkylamino, mono-N- or di-N,N-($C_3$–$C_6$)cycloalkylamino or N-($C_1$–$C_6$)alkyl-N-($C_3$–$C_6$)cycloalkylamino;

wherein said mono-N- or di-N,N-($C_1$–$C_6$)alkylamino, mono-N- or di-N,N-($C_3$–$C_6$)cycloalkylamino or N-($C_1$–$C_6$)alkyl-N-($C_3$–$C_6$)cycloalkylamino is optionally mono-, di-, or tn-substituted independently on each of said ($C_1$–$C_6$)alkyl or ($C_3$–$C_6$)cycloalkyl with ($C_3$–$C_6$)cycloalkyl, hydroxy, ($C_1$–$C_3$)alkoxy, ($C_3$–$C_6$) cycloalkoxy, cyano or fluoro;

or said sulfonyl is optionally mono-substituted with a partially unsaturated or fully unsaturated five to eight membered ring optionally having one to two heteroatoms selected independently from oxygen, sulfur and nitrogen, a four to seven membered saturated ring having one to two heteroatoms selected independently from oxygen, sulfur or nitrogen or an aromatic bicyclic ring consisting of two fused three to six membered rings, taken independently, optionally having one to four heteratoms selected independently from nitrogen, sulfur and oxygen;

wherein said ring is optionally mono-, di-, or tri-substituted independently with nitro, amino, hydroxy, ($C_2$–$C_6$)alkenyl, ($C_1$–$C_4$)alkylthio, halo, cyano, ($C_3$–$C_6$)cycloalkyl($C_1$–$C_6$)alkyl, ($C_3$–$C_6$)cycloalkyl ($C_1$–$C_6$)alkyloxy, ($C_1$–$C_6$)alkyl, ($C_3$–$C_6$)cycloalkyl, ($C_1$–$C_6$)alkoxy, ($C_3$–$C_6$)cycloalkoxy, said ($C_3$–$C_6$) cycloalkyl($C_1$–$C_6$)alkyl, ($C_3$–$C_6$)cycloalkyl($C_1$–$C_6$) alkyloxy, ($C_1$–$C_6$)alkyl, ($C_3$–$C_6$)cycloalkyl, ($C_1$–$C_6$) alkoxy and ($C_3$–$C_6$)cycloalkoxy moieties optionally substituted with one to nine fluorines;

wherein said $R^3$ ring is optionally mono-, or di-substituted independently on a single carbon or optionally mono-substituted independently on two separate carbons with $R^5$ or $R^6$ wherein $R^5$ and $R^6$ are independently
1) H, carboxy, oxo, amino, halo, cyano, hydroxy, nitro, ($C_2$–$C_6$)alkenyl, ($C_1$–$C_4$)alkylthio, ($C_1$–$C_4$)alkoxy, ($C_3$–$C_8$)cycloalkoxy, ($C_3$–$C_8$)cycloalkyl($C_1$–$C_8$)alkoxy, said ($C_1$–$C_8$)alkoxy, ($C_3$–$C_8$)cycloalkyl($C_1$–$C_8$)alkoxy and ($C_3$–$C_8$)cycloalkoxy substituents optionally substituted with one to nine fluorines or optionally mono- or di-substituted with hydroxy;
2) mono-N- or di-N,N-($C_1$–$C_6$)alkylamino, mono-N- or di-N,N-($C_3$–$C_6$)cycloalkylamino or N-($C_1$–$C_6$)alkyl-N-($C_3$–$C_6$)cycloalkylamino, said mono-N- or di-N,N-($C_1$–$C_6$)alkylamino, mono-N- or di-N,N-($C_3$–$C_6$) cycloalkylamino or N-($C_1$–$C_6$)alkyl-N-($C_3$–$C_6$) cycloalkylamino optionally mono-, di-, or tri-substituted independently on each ($C_1$–$C_6$)alkyl or ($C_3$–$C_6$) cycloalkyl with ($C_3$–$C_6$)cycloalkyl, hydroxy, ($C_1$–$C_6$) alkoxy, ($C_3$–$C_6$)cycloalkoxy, ($C_3$–$C_6$)cycloalkyl($C_1$–$C_6$) alkoxy, cyano or substituted with one to nine fluorines;
3) ($C_1$–$C_8$)alkoxycarbonyl, ($C_3$–$C_8$)cycloalkoxycarbonyl, ($C_3$–$C_8$)cycloalkyl($C_1$–$C_8$)alkoxycarbonyl, ($C_1$–$C_8$) alkylformyl, ($C_3$–$C_8$)cycloalkylformyl or ($C_3$–$C_8$) cycloalkyl($C_1$–$C_8$)alkylformyl said ($C_1$–$C_8$) alkoxycarbonyl, ($C_3$–$C_8$)cycloalkoxycarbonyl, ($C_3$–$C_8$) cycloalkyl($C_1$–$C_8$)alkoxycarbonyl, ($C_1$–$C_8$)alkylformyl, ($C_3$–$C_8$)cycloalkylformyl or ($C_3$–$C_8$)cycloalkyl($C_1$–$C_8$) alkylformyl optionally mono-, di- or tri-substituted independently with hydroxy, cyano, fluoro, ($C_1$–$C_6$)alkoxy or ($C_1$–$C_6$)alkyl, said($C_1$–$C_6$)alkoxy or ($C_1$–$C_6$)alkyl optionally substituted with from one to nine fluorines;
4) an X ring, optionally linked through ($C_1$–$C_8$)alkyl or carbonyl, wherein said X ring is a partially unsaturated or fully unsaturated five to eight membered ring optionally having one to two heteroatoms selected independently from oxygen, sulfur and nitrogen or said X ring is a four to seven membered saturated ring having one to three heteroatoms selected independently from oxygen, sulfur and nitrogen or said X ring is an aromatic bicyclic ring consisting of two fused three to six membered rings, taken independently, optionally having one to four heteroatoms selected independently from nitrogen, sulfur and oxygen; wherein said X ring is optionally substituted with a maximum of three substituents selected independently from Group XI, Group XII or Group XIII Group XI: wherein said X ring is optionally mono-, di- or tri-substituted independently with nitro, amino, hydroxy, ($C_2$–$C_6$)alkenyl, ($C_1$–$C_4$)alkylthio, halo, cyano, ($C_1$–$C_6$)alkyl, ($C_3$–$C_6$)cycloalkyl, ($C_3$–$C_6$) cycloalkyl($C_1$–$C_6$)alkyl, ($C_3$–$C_6$)cycloalkyl($C_1$–$C_6$) alkoxy, ($C_1$–$C_6$)alkoxy, ($C_3$–$C_6$)cycloalkoxy, said ($C_1$–$C_6$)alkyl, ($C_3$–$C_6$)cycloalkyl, ($C_1$–$C_6$)alkoxy, ($C_3$–$C_6$)cycloalkyl($C_1$–$C_6$)alkyl, ($C_3$–$C_6$)cycloalkyl ($C_1$–$C_6$)alkoxy, and ($C_3$–$C_6$)cycloalkoxy moieties optionally substituted with one to nine fluorines;

Group XII: said X ring is optionally mono- or di-substituted independently with mono-N- or di-N,N-($C_1$–$C_6$)alkylamino, mono-N- or di-N,N-($C_3$–$C_6$) cycloalkylamino or N-($C_1$–$C_6$)alkyl-N-($C_3$–$C_6$) cycloalkylamino;

wherein said mono-N- or di-N,N-($C_1$–$C_6$)alkylamino, mono-N- or di-N,N-($C_3$–$C_6$)cycloalkylamino or N-($C_1$–$C_6$)alkyl-N-($C_3$–$C_6$)cycloalkylamino is optionally mono-, di-, or tri-substituted independently on each of said ($C_1$–$C_6$)alkyl or ($C_3$–$C_6$)cycloalkyl with ($C_3$–$C_6$)cycloalkyl, hydroxy, ($C_1$–$C_3$)alkoxy, ($C_3$–$C_6$) cycloalkoxy, cyano or fluoro; or Group XIII: said X ring is optionally mono-substituted with a four to seven membered saturated nitrogen containing ring optionally having one to two additional heteroatoms selected independently from sulfur, oxygen or nitrogen linked to the X ring through nitrogen, said four to seven membered ring optionally substituted with ($C_1$–$C_5$)alkyl, said ($C_1$–$C_5$)alkyl optionally substituted with one to nine fluorines; 5) ($C_1$–$C_8$)alkyl, ($C_3$–$C_8$)cycloalkyl or ($C_3$–$C_8$)cycloalkyl($C_1$–$C_8$)alkyl, said ($C_1$–$C_8$)alkyl, ($C_3$–$C_8$)cycloalkyl or ($C_3$–$C_8$) cycloalkyl($C_1$–$C_8$)alkyl optionally substituted with one to nine fluorines and said ($C_1$–$C_8$)alkyl, ($C_3$–$C_8$) cycloalkyl or ($C_3$–$C_8$)cycloalkyl($C_1$–$C_8$)alkyl optionally substituted with a maximum of three substituents selected independently from Group XIV, XV, XVI or XVII; wherein Group XIV: said ($C_1$–$C_8$)alkyl, ($C_3$–$C_8$)cycloalkyl ($C_1$–$C_8$)alkyl or ($C_3$–$C_8$)cycloalkyl is optionally mono, di- or tri-substituted independently with mono-N- or di-N,N-($C_1$–$C_6$)alkylaminocarbonyl mono-N- or di-N, N-($C_3$—$C_6$)cycloalkylaminocarbonyl, N-($C_1$–$C_6$) alkyl-N-($C_3$–$C_6$)cycloalkylaminocarbonyl, carboxy, nitro, amino, hydroxy, ($C_2$–$C_6$)alkenyl, ($C_1$–$C_4$) alkylthio, halo, cyano, ($C_1$–$C_6$)alkyl, ($C_3$–$C_6$) cycloalkyl, ($C_1$–$C_6$)alkoxy, ($C_3$–$C_6$)cycloalkoxy, ($C_1$–$C_6$)alkoxycarbonyl, said mono-N- or di-N,N-($C_1$–$C_6$)alkylaminocarbonyl, mono-N- or di-N,N-($C_3$–$C_6$)cycloalkylaminocarbonyl, N-($C_1$–$C_6$)alkyl-N-($C_3$–$C_6$)cycloalkylaminocarbonyl, ($C_1$–$C_6$)alkyl, ($C_3$–$C_6$)cycloalkyl, ($C_1$–$C_6$)alkoxy and ($C_3$–$C_6$) cycloalkoxy moieties optionally substituted with one to nine fluorines;

Group XV: said $(C_1-C_8)$alkyl, $(C_3-C_8)$cycloalkyl or $(C_3-C_8)$cycloalkyl$(C_1-C_8)$alkyl optionally mono-substituted with a four to seven membered saturated nitrogen containing ring, linked through a ring nitrogen, optionally having one to two additional heteroatoms selected independently from sulfur, oxygen or nitrogen, said four to seven membered ring optionally substituted with $(C_1-C_5)$alkyl, said $(C_1-C_5)$alkyl optionally substituted with one to nine fluorines;

Group XVI: said $(C_1-C_8)$alkyl, $(C_3-C_8)$cycloalkyl or $(C_3-C_8)$cycloalkyl$(C_1-C_8)$alkyl optionally mono-, di- or tri-substituted independently with mono-N- or di-N,N-$(C_1-C_6)$alkylamino, mono-N- or di-N,N-$(C_3-C_6)$cycloalkylamino, or N-$(C_1-C_6)$alkyl-N-$(C_3-C_6)$cycloalkylamino, said mono-N- or di-N,N-$(C_1-C_6)$alkylamino, mono-N- or di-N,N-$(C_3-C_6)$cycloalkylamino or N-$(C_1-C_6)$alkyl-N-$(C_3-C_6)$cycloalkylamino optionally mono, di-, or tri-substituted independently on each $(C_1-C_6)$alkyl or $(C_3-C_6)$cycloalkyl with $(C_3-C_6)$cycloalkyl, hydroxy, $(C_1-C_3)$alkoxy, $(C_3-C_6)$cycloalkoxy, cyano or fluoro;

Group XVII: said $(C_1-C_8)$alkyl, $(C_3-C_8)$cycloalkyl or $(C_3-C_8)$cycloalkyl$(C_1-C_8)$alkyl optionally mono-, di- or tri-substituted independently with $(C_1-C_6)$alkoxycarbonyl or $(C_1-C_6)$alkylformyl, said $(C_1-C_6)$alkoxycarbonyl or $(C_1-C_6)$alkylformyl optionally mono-, di- or tri-substituted independently with hydroxy, cyano, fluoro, $(C_1-C_6)$alkyl, $(C_1-C_6)$alkoxy, $(C_3-C_6)$cycloalkyl or $(C_3-C_6)$cycloalkoxy, said $(C_1-C_6)$alkyl, $(C_1-C_6)$alkoxy, $(C_3-C_6)$cycloalkyl or $(C_3-C_6)$cycloalkoxy optionally substituted with one to nine fluorines;

6) sulfonyl, said sulfonyl optionally mono-substituted with amino, hydroxy, $(C_2-C_8)$alkenyl, $(C_1-C_8)$alkyl, $(C_3-C_8)$cycloalkyl, $(C_3-C_8)$cycloalkyl$(C_1-C_8)$alkyl, $(C_3-C_8)$cycloalkyl$(C_1-C_8)$alkoxy, $(C_1-C_8)$alkoxy, $(C_3-C_8)$cycloalkoxy, said $(C_1-C_8)$alkenyl, $(C_3-C_8)$cycloalkyl$(C_1-C_8)$alkyl, $(C_3-C_8)$cycloalkyl$(C_1-C_8)$alkoxy, $(C_1-C_8)$alkyl, $(C_3-C_8)$cycloalkyl, $(C_1-C_8)$alkoxy or $(C_3-C_8)$cycloalkoxy moieties optionally substituted with one to nine fluorines or said sulfonyl optionally mono-substituted with mono-N- or di-N,N-$(C_1-C_6)$alkylamino, mono-N- or di-N,N-$(C_3-C_6)$cycloalkylamino or N-$(C_1-C_6)$alkyl-N-$(C_3-C_6)$cycloalkylamino;

wherein said mono-N- or di-N,N-$(C_1-C_6)$alkylamino, mono-N- or di-N,N-$(C_3-C_6)$cycloalkylamino or N-$(C_1-C_6)$alkyl-N-$(C_3-C_6)$cycloalkylamino is optionally mono-, di-, or tri-substituted independently on each of said $(C_1-C_6)$alkyl or $(C_3-C_6)$cycloalkyl with $(C_3-C_6)$cycloalkyl, hydroxy, $(C_1-C_3)$alkoxy, $(C_3-C_6)$cycloalkoxy, cyano or fluoro.

A preferred group of compounds, designated the A Group, contains those compounds having the Formula I as shown above wherein Y is phenyl, benzofuranyl, pyrrolyl or thiophenyl, said Y aromatic rings optionally mono- or di-substituted independently with chloro, fluoro, $(C_1-C_4)$alkoxy, hydroxy, $(C_1-C_4)$ alkyl, cyano, trifluoromethyl or trifluoromethoxy;

L is carbon;

M is nitrogen;

$R^3$ is a five to seven membered diaza saturated ring;

$R^3$ is optionally mono-substituted on nitrogen with $(C_1-C_8)$alkyl, $(C_3-C_8)$cycloalkyl or $(C_3-C_8)$cycloalkyl$(C_1-C_8)$alkyl;

wherein said $(C_1-C_8)$alkyl, $(C_3-C_8)$cycloalkyl or $(C_3-C_8)$cycloalkyl$(C_1-C_8)$alkyl are optionally mono- or di-substituted independently with hydroxy and optionally substituted with one to nine fluorines; or $R^3$ is optionally mono-substituted on nitrogen with a carbonyl linked T ring wherein the T ring is phenyl, furanyl or thiophenyl, wherein said ring is optionally mono-, di-, or tri-substituted independently with hydroxy, halo, $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy, said $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy moieties optionally substituted with one to nine fluorines; or $R^3$ is optionally mono-substituted on nitrogen with a five to eight membered aromatic T ring optionally having one or two heteroatoms selected from nitrogen or sulfur, said T ring optionally linked through $(C_1-C_6)$alkyl, wherein said T ring is optionally mono-, di-, or tri-substituted independently with hydroxy, halo, $(C_1-C_6)$cycloalkyl$(C_1-C_6)$alkyl, $(C_3-C_6)$cycloalkyl$(C_1-C_6)$alkoxy, $(C_1-C_6)$alkyl, $(C_3-C_6)$cycloalkyl, $(C_1-C_6)$alkoxy or $(C_3-C_6)$cycloalkoxy;

wherein said $(C_3-C_6)$cycloalkyl$(C_1-C_6)$alkyl, $(C_3-C_6)$cycloalkyl$(C_1-C_6)$alkoxy, $(C_1-C_6)$alkyl, $(C_3-C_6)$cycloalkyl, $(C_1-C_6)$alkoxy or $(C_3-C_6)$cycloalkoxy moieties are optionally substituted with one to nine fluorines; and pharmaceutically acceptable salts thereof.

A group of compounds which is preferred among the A Group of compounds, designated the B Group, contains those compounds wherein $R^3$ is a five to six membered diaza saturated ring; and $R^3$ is optionally mono-substituted on nitrogen with $(C_1-C_8)$alkyl, $(C_3-C_8)$cycloalkyl or $(C_3-C_8)$cycloalkyl$(C_1-C_8)$alkyl wherein said $(C_1-C_8)$alkyl, $(C_3-C_8)$cycloalkyl or $(C_3-C_8)$cycloalkyl$(C_1-C_8)$alkyl are optionally mono- or di-substituted with hydroxy and optionally substituted with one to nine fluorines; or $R^3$ is optionally mono-substituted on nitrogen with phenyl, said phenyl optionally linked through $(C_1-C_6)$alkyl, said phenyl optionally mono-, di-, or tri-substituted independently with hydroxy, halo, $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy;

wherein said $(C_3-C_6)$cycloalkyl$(C_1-C_6)$alkyl, $(C_3-C_6)$cycloalkyl$(C_1-C_6)$alkoxy, $(C_1-C_6)$alkyl, $(C_1-C_6)$cycloalkyl, $(C_1-C_6)$alkoxy or $(C_3-C_6)$cycloalkoxy moieties optionally substituted with one to nine fluorines; or $R^3$ is optionally mono-substituted on nitrogen with pyridyl or pyrimidyl, said pyridyl or pyrimidyl optionally linked through $(C_1-C_6)$alkyl, and pharmaceutically acceptable salts thereof.

A group of compounds which is preferred among the B Group of compounds, designated the C Group, contains those compounds wherein Y is phenyl optionally mono- or di-substituted independently with chloro, fluoro, $(C_1-C_2)$ alkyl, cyano or trifluoromethyl; and $R^3$ is piperazinyl optionally mono-substituted on the nitrogen with $(C_1-C_4)$alkyl, $(C_3-C_6)$cycloalkyl or $(C_3-C_6)$cycloalkyl$(C_1-C_4)$alkyl, said substituents optionally mono-substituted with hydroxy or mono-, di-, or tri-substituted with fluoro, and pharmaceutically acceptable salts thereof.

Especially preferred compounds within the C Group of compounds are compounds wherein a. Y is 3,4-dichlorophenyl; and
   $R^3$ is N-ethylpiperazinyl;
b. Y is 3-chlorophenyl; and
   $R^3$ is N-isobutylpiperazinyl;
c. Y is 3,4-difluorophenyl; and
   $R^3$ is N-cyclopropylmethylpiperazinyl;
d. Y is 3-chlorophenyl; and
   $R^3$ is N-(n-propyl)piperazinyl;
e. Y is 3-chloro,4-fluorophenyl; and
   $R^3$ is N-cyclopropylmethylpiperazinyl;
f. Y is 4-chloro-3-methylphenyl; and
   $R^3$ is N-cyclopropylmethylpiperazinyl;
g. Y is 3,4-difluorophenyl; and
   $R^3$ is N-(2-cyclopropylethyl)-piperazinyl;
h. Y is 3-chloro-4-fluorophenyl; and
   $R^3$ is N-isobutylpiperazinyl;
i. Y is 3-chloro-fluorophenyl; and
   $R^3$ is N-(2-cyclopropylethyl)-piperazinyl;
j. Y is 3-ethylphenyl; and
   $R^3$ is N-isobutylpiperazinyl;
k. Y is 3-chlorophenyl; and
   $R^3$ is N-2,2,2-trifluoroethylpiperazinyl;
l. Y is 4-trifluoromethylphenyl; and
   $R^3$ is N-isobutylpiperazinyl;
m. Y is 3,5-di-fluorophenyl; and
   $R^3$ is N-isobutylpiperazinyl;
n. Y is 3-chlorophenyl; and
   $R^3$ is N-(3-hydroxy-1,2-dimethyl-n-propyl)piperazinyl;
o. Y is 3-cyanophenyl; and
   $R^3$ is N-isobutylpiperazinyl;
p. Y is 3-cyanophenyl; and
   $R^3$ is N-cyclopropylmethylpiperazinyl; and pharmaceutically acceptable salts of said compounds.

Especially preferred compounds of Formula I are the compounds:

1-{4-[4-(3,4-Dichloro-phenyl)-1H-imidazol-2-yl]-pyridin-2-yl}-4-ethyl-piperazine;
1-{4-[4-(3-Chloro-phenyl)-1H-imidazol-2-yl]-pyridin-2-yl}-4-isobutyl-piperazine;
1-{4-[4-(3,4-Difluoro-phenyl)-1H-imidazol-2-yl]-pyridin-2-yl}-4-cyclopropylmethyl-piperazine;
1-{4-[4-(3-Chloro-phenyl)-1H-imidazol-2-yl]-pyridin-2-yl}-4-propyl-piperazine;
1-{4-[4-(3-Chloro-4-fluoro-phenyl)-1H-imidazol-2-yl]-pyridin-2-yl}-4-cyclopropylmethyl-piperazine;
1-{4-[4-(4-Chloro-3-methyl-phenyl)-1H-imidazol-2-yl]-pyridin-2-yl}-4-cyclopropylmethyl-piperazine;
1-{4-[4-(3,4-Difluoro-phenyl)-1H-imidazol-2-yl]-pyridin-2-yl}-4-cyclopropylethyl-piperazine;
1-{4-[4-(3-Chloro-4-Fluoro-phenyl)-1H-imidazol-2-yl]-pyridin-2-yl}-4-isobutyl-piperazine; and pharmaceutically acceptable salts of said compounds.

Other especially preferred compounds of Formula I are the compounds:

1-{4-[4-(3-Chloro-4-fluoro-phenyl)-1H-imidazol-2-yl]-pyridin-2-yl}-4-cyclopropylethyl-piperazine;
1-{4-[4-(3-Ethyl-phenyl)-1H-imidazol-2-yl]-pyridin-2-yl}-4-isobutyl-piperazine;
1-(4-[4-(3-Chloro-phenyl)-1H-imidazol-2-yl]-pyridin-2-yl)-4-(2,2,2-trifluoro-ethyl)-piperazine;
1-{4-[4-(4-Trifluoromethyl-phenyl)-1H-imidazol-2-yl]-pyridin-2-yl}-4-cyclopropylmethyl-piperazine;
1-{4-[4-(3,5-Difluoro-phenyl)-1H-imidazol-2-yl]-pyridin-2-yl}-4-isobutyl-piperazine;
3-(4-{4-[4-(3-Chloro-phenyl)-1H-imidazol-2-yl]-pyridin-2-yl}-piperazin-1-yl)-2-methyl-butan-1-ol;
3-{2-[2-(4-Isobutyl-piperazin-1-yl)-pyridin-4-yl]-1H-imidazol-4-yl}-benzonitrile;
3-{2-[2-(4-Cyclopropylmethyl-piperazin-1-yl)-pyridin-4-yl]-1H-imidazol-4-yl}-benzonitrile; and pharmaceutically acceptable salts of said compounds.

A preferred group of compounds, designated the D Group, contains those compounds having the Formula I as shown above wherein Y is phenyl, benzofuranyl, pyrrolyl or thiophenyl, said Y aromatic rings optionally mono- or di-substituted independently with chloro, fluoro, $(C_1-C_4)$alkoxy, hydroxy, $(C_1-C_4)$ alkyl, cyano, trifluoromethyl or trifluoromethoxy;

L is nitrogen;
M is carbon;
$R^3$ is a five to seven membered diaza saturated ring;
$R^3$ is optionally mono-substituted on nitrogen with $(C_1-C_8)$ alkyl, $(C_3-C_8)$cycloalkyl or $(C_3-C_8)$cycloalkyl$(C_1-C_8)$ alkyl;

wherein said $(C_1-C_8)$alkyl, $(C_3-C_8)$cycloalkyl or $(C_3-C_8)$ cycloalkyl$(C_1-C_8)$alkyl are optionally mono- or di-substituted independently with hydroxy and optionally substituted with one to nine fluorines; or $R^3$ is optionally mono-substituted on nitrogen with a carbonyl linked T ring wherein said T ring is phenyl, furanyl or thiophenyl, wherein said ring is optionally mono-, di-, or tri-substituted independently with hydroxy, halo, $(C_3-C_6)$cycloalkyl$(C_1-C_6)$alkyl, $(C_1-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$ cycloalkoxy, said $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$ cycloalkoxy moieties optionally substituted with one to nine fluorines; or $R^3$ is optionally mono-substituted on nitrogen with a five to eight membered aromatic T ring optionally having one or two heteroatoms selected independently from nitrogen or sulfur, said T ring optionally linked through $(C_1-C_6)$alkyl, wherein said T ring is optionally mono-, di-, or tri-substituted independently with hydroxy, halo, $(C_3-C_6)$ cycloalkyl$(C_1-C_6)$alkyl, $(C_3-C_6)$cycloalkyl$(C_1-C_6)$ alkoxy, $(C_1-C_6)$alkyl, $(C_3-C_6)$cycloalkyl, $(C_1-C_6)$ alkoxy or $(C_3-C_6)$cycloalkoxy;

wherein said $(C_1-C_6)$cycloalkyl$(C_1-C_6)$alkyl, $(C_3-C_6)$ cycloalkyl$(C_1-C_6)$alkoxy, $(C_1-C_6)$alkyl, $(C_1-C_6)$ cycloalkyl, $(C_1-C_6)$alkoxy or $(C_3-C_6)$cycloalkoxy moieties are optionally substituted with one to nine fluorines; and pharmaceutically acceptable salts thereof.

A group of compounds which is preferred among the D Group of compounds, designated the E Group, contains those compounds wherein $R^3$ is a five to six membered diaza saturated ring; and
$R^3$ is optionally mono-substituted on nitrogen with $(C_1-C_8)$ alkyl, $(C_3-C_8)$cycloalkyl or $(C_3-C_8)$cycloalkyl$(C_1-C_8)$ alkyl wherein said $(C_1-C_8)$alkyl, $(C_3-C_8)$cycloalkyl or $(C_3-C_8)$ cycloalkyl$(C_1-C_8)$alkyl are optionally mono- or di-substituted with hydroxy and optionally substituted with one to nine fluorines; or $R^3$ is optionally mono-substituted on nitrogen with phenyl, said phenyl optionally linked through $(C_1-C_6)$ alkyl, said phenyl optionally mono-, di-, or tri-substituted independently with hydroxy, halo, $(C_3-C_6)$ cycloalkyl$(C_1-C_6)$alkyl, $(C_3-C_6)$cycloalkyl$(C_1-C_6)$ alkoxy,$(C_1-C_6)$alkyl, $(C_3-C_6)$cycloalkyl, $(C_1-C_6)$ alkoxy or $(C_3-C_6)$cycloalkoxy;

wherein said $(C_3-C_6)$cycloalkyl$(C_1-C_6)$alkyl, $(C_3-C_6)$ cycloalkyl$(C_1-C_6)$alkoxy, $(C_1-C_6)$alkyl, $(C_3-C_6)$ cycloalkyl, $(C_1-C_6)$alkoxy or $(C_3-C_6)$cycloalkoxy moieties are optionally substituted with one to nine fluorines; or $R^3$ is optionally mono-substituted on nitrogen with pyridyl or a pyrimidyl ring, said pyridyl or pyrimidyl ring optionally linked through $(C_1-C_6)$alkyl, and pharmaceutically acceptable salts thereof.

A group of compounds which is preferred among the E Group of compounds, designated the F Group, contains those compounds wherein Y is phenyl optionally mono- or di-substituted independently with chloro, fluoro, $(C_1-C_2)$ alkyl, cyano or trifluoromethyl; and $R^3$ is piperazinyl optionally monosubstituted on the nitrogen with $(C_1-C_4)$alkyl, $(C_3-C_6)$cycloalkyl or $(C_3-C_6)$ cycloalkyl$(C_1-C_4)$alkyl, said substituents optionally mono-substituted with hydroxy or mono-, di- or tri-substituted with fluoro, and pharmaceutically acceptable salts thereof.

Especially preferred compounds within the F Group of compounds are compounds wherein a. Y is 4-fluorophenyl; and
$R^3$ is N-isobutylpiperazinyl;
b. Y is 4-fluorophenyl; and
$R^3$ is N-cyclopropylmethylpiperazinyl;
c. Y is 3,4-dichlorophenyl; and
$R^3$ is N-cyclopropylmethylpiperazinyl;
d. Y is 3,4-dichlorophenyl; and
$R^3$ is N-isobutylpiperazinyl;
e. Y is 4-chlorophenyl; and
$R^3$ is N-ethylpiperazinyl;
f. Y is 4-chlorophenyl; and
$R^3$ is N-isobutylpiperazinyl;
g. Y is 3-chlorophenyl; and
$R^3$ is N-ethylpiperazinyl;
h. Y is 2-chlorophenyl; and
$R^3$ is N-ethylpiperazinyl;
i. Y is 4-fluorophenyl; and
$R^3$ is N-2,2,2-trifluoroethylpiperazinyl;
j. Y is 3-chlorophenyl; and
$R^3$ is N-2,2,2-trifluoroethylpiperazinyl;
k. Y is 4-chlorophenyl; and
$R^3$ is N-2,2,2-trifluoroethylpiperazinyl;
l. Y is 3-chloro-4-fluorophenyl; and
$R^3$ is N-ethylpiperazinyl; and
pharmaceutically acceptable salts of said compounds.

Other especially preferred compounds of Formula I are the compounds:

1-{5-[4-(4-Fluoro-phenyl)-1H-imidazol-2-yl]-pyridin-2-yl}-4-isobutyl-piperazine;
1-Cyclopropylmethyl-4-{5-[4-(4-fluoro-phenyl)-1H-imidazol-2-yl]-pyridin-2-yl}-piperazine;
1-Cyclopropylmethyl-4-{5-[4-(3,4-dichloro-phenyl)-1H-imidazol-2-yl]-pyridin-2-yl)-piperazine;
1-{5-[4-(3,4-Dichloro-phenyl)-1H-imidazol-2-yl]-pyridin-2-yl}-4-isobutyl-piperazine;
1-{5-[4-(4-Chloro-phenyl)-1H-imidazol-2-yl]-pyridin-2-yl}-4-ethyl-piperazine;
1-{5-[4-(4-Chloro-phenyl)-1H-imidazol-2-yl]-pyridin-2-yl}-4-isobutyl-piperazine;

and pharmaceutically acceptable salts of said compounds.

Other especially preferred compounds of Formula I are the compounds:

1-{5-[4-(3-Chloro-phenyl)-1H-imidazol-2-yl]-pyridin-2-yl}-4-ethyl-piperazine;
1-{5-[4-(2-Chloro-phenyl)-1H-imidazol-2-yl]-pyridin-2-yl}-4-ethyl-piperazine;
1-{4-[4-(4-Fluoro-phenyl)-1H-imidazol-2-yl]-pyridin-2-yl}-4-(2,2,2-trifluoro-ethyl)-piperazine;
1-{4-[4-(3-Chloro-phenyl)-1H-imidazol-2-yl]-pyridin-2-yl}-4-(2,2,2-trifluoro-ethyl)-piperazine;
1-{4-[4-(4-Chloro-phenyl)-1H-imidazol-2-yl]-pyridin-2-yl}-4-(2,2,2-trifluoro-ethyl)-piperazine;
1-{5-[4-(3-Chloro-4-fluoro-phenyl)-1H-imidazol-2-yl]-pyridin-2-yl}-4-ethyl-piperazine;

and the pharmaceutically acceptable salts of said compounds.

A preferred group of compounds, designated the G Group, contains those compounds having the Formula I as shown above wherein Y is phenyl, benzofuranyl, pyrrolyl or thiophenyl, said Y rings optionally mono- or di-substituted independently with chloro, fluoro, $(C_1-C_4)$alkoxy, hydroxy, $(C_1-C_4)$ alkyl, cyano, trifluoromethyl or trifluoromethoxy;

L is carbon;

M is nitrogen;

$R^3$ is a four to six membered saturated mono-aza ring optionally substituted on carbon;

$R^3$ is optionally mono- or di-substituted independently with hydroxy, oxo, amino, halo, mono-N- or di-N,N-$(C_1-C_6)$ alkylamino, mono-N- or di-N,N-$(C_3-C_6)$ cycloalkylamino, N-$(C_1-C_6)$alkyl-N-$(C_3-C_6)$ cycloalkylamino, $(C_1-C_8)$alkyl, $(C_3-C_8)$cycloalkyl, $(C_3-C_8)$cycloalkyl$(C_1-C_8)$alkyl, $(C_1-C_8)$alkoxy, $(C_3-C_8)$ cycloalkoxy or $(C_3-C_8)$cycloalkyl$(C_1-C_8)$alkoxy;

wherein said mono-N- or di-N,N-$(C_1-C_6)$alkylamino, mono-N- or di-N,N-$(C_3-C_6)$cycloalkylamino, N-$(C_1-C_6)$alkyl-N-$(C_3-C_6)$cycloalkylamino, $(C_1-C_8)$ alkyl, $(C_3-C_8)$cycloalkyl, $(C_3-C_8)$cycloalkyl$(C_1-C_8)$ alkyl, $(C_1-C_8)$alkoxy, $(C_3-C_8)$cycloalkoxy or $(C_3-C_8)$ cycloalkyl$(C_1-C_8)$alkoxy are optionally mono- or di-substituted with hydroxy and optionally substituted with one to nine fluorines; or $R^3$ is optionally mono-substituted with a five to eight membered aromatic X ring optionally having one to two heteroatoms selected independently from nitrogen or sulfur, said X ring optionally linked through $(C_1-C_6)$alkyl or carbonyl wherein said X ring is optionally mono-, di-, or tri-substituted independently with hydroxy, halo, $(C_3-C_6)$ cycloalkyl$(C_1-C_6)$alkyl, $(C_3-C_6)$cycloalkyl$(C_1-C_6)$ alkoxy, $(C_1-C_6)$alkyl, $(3-C_6)$cycloalkyl, $(C_1-C_6)$ alkoxy or $(C_3-C_6)$cycloalkoxy;

wherein said $(C_3-C_6)$cycloalkyl$(C_1-C_6)$alkyl, $(C_3-C_6)$ cycloalkyl$(C_1-C_6)$alkoxy, $(C_1-C_6)$alkyl, $(C_3-C_6)$ cycloalkyl, $(C_1-C_6)$alkoxy or $(C_3-C_6)$cycloalkoxy moieties are optionally substituted with one to nine fluorines; or R³ is optionally mono-substituted with a four to seven membered saturated nitrogen containing X ring optionally having one to two additional heteroatoms selected independently from oxygen, nitrogen and sulfur, said ring linked to R³ through N, said link optionally containing a $(C_1-C_6)$alkyl, and pharmaceutically acceptable salts thereof.

A group of compounds which is preferred among the G Group of compounds, designated the H Group, contains those compounds wherein R³ is optionally mono-substituted with hydroxy, amino, halo, mono-N- or di-N,N-$(C_1-C_6)$alkylamino, $(C_1-C_8)$ alkoxy, $(C_3-C_8)$cycloalkoxy, $(C_1-C_8)$alkyl, $(C_3-C_8)$ cycloalkyl, $(C_3-C_8)$cycloalkyl$(C_1-C_8)$alkoxy or $(C_3-C_8)$ cycloalkyl$(C_1-C_8)$alkyl, said mono-N- or di-N,N-$(C_1-C_8)$alkylamino, $(C_1-C_8)$alkoxy, $(C_3-C_8)$cycloalkoxy, $(C_1-C_8)$alkyl, $(C_3-C_8)$cycloalkyl, $(C_3-C_8)$cycloalkyl $(C_1-C_8)$alkoxy or $(C_3-C_8)$cycloalkyl$(C_1-C_8)$alkyl optionally mono- or di-substituted with hydroxy or optionally substituted with one to nine fluorines; or R³ is optionally mono-substituted with X, wherein X is phenyl, optionally linked through $(C_1-C_6)$alkyl or carbonyl, said phenyl optionally mono-, di- or tri-substituted independently with hydroxy, halo, $(C_3-C_6)$ cycloalkyl$(C_1-C_6)$alkyl, $(C_3-C_6)$cycloalkyl$(C_1-C_6)$ alkoxy,$(C_1-C_6)$alkyl, $(C_3-C_6)$cycloalkyl, $(C_1-C_6)$alkoxy or $(C_3-C_6)$cycloalkoxy, said $(C_3-C_6)$cycloalkyl$(C_1-C_6)$ alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$ cycloalkoxy moieties optionally substituted with one to nine fluorines; or R³ is optionally mono-substituted with pyridyl or a pyrimidyl X ring, said X ring optionally linked through carbonyl, and pharmaceutically acceptable salts thereof.

A group of compounds which is preferred among the H Group of compounds, designated the I Group, contains those compounds wherein Y is phenyl, said phenyl optionally mono- or di-substituted independently with chloro, fluoro, $(C_1-C_4)$alkoxy, hydroxy, $(C_1-C_4)$ alkyl, cyano, trifluoromethyl or trifluoromethoxy;

R³ is pyrrolidinyl or piperidinyl;

R³ is optionally mono-substituted with hydroxy, amino, halo, mono-N- or di-N,N-$(C_1-C_6)$alkylamino, $(C_1-C_8)$ alkoxy, $(C_3-C_8)$cycloalkoxy, $(C_1-C_8)$alkyl, $(C_3-C_8)$ cycloalkyl, $(C_3-C_8)$cycloalkyl$(C_1-C_8)$alkoxy or $(C_3-C_8)$ cycloalkyl$(C_1-C_8)$alkyl, said $(C_1-C_8)$alkoxy, $(C_3-C_8)$ cycloalkoxy, $(C_1-C_8)$alkyl, $(C_3-C_8)$cycloalkyl, $(C_3-C_8)$ cycloalkyl$(C_1-C_8)$alkoxy or $(C_3-C_8)$cycloalkyl$(C_1-C_8)$ alkyl optionally mono- or di-substituted with hydroxy or optionally having one to nine fluorines; or R³ is optionally mono-substituted with phenyl, said phenyl optionally mono-substituted with hydroxy,$(C_3-C_6)$ cycloalkyl$(C_1-C_8)$alkyl, $(C_3-C_6)$cycloalkyl$(C_1-C_6)$ alkoxy,$(C_1-C_6)$alkyl, $(C_3-C_6)$cycloalkyl, $(C_1-C_6)$alkoxy or $(C_3-C_6)$cycloalkoxy, said $(C_3-C_6)$cycloalkyl$(C_1-C_6)$ alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$ cycloalkoxy moieties optionally substituted with one to nine fluorines, and pharmaceutically acceptable salts thereof.

A group of compounds which is preferred among the I Group of compounds, designated the J Group, contains those compounds wherein R³ is pyrrolidinyl or piperidinyl;

R³ is optionally monosubstituted with hydroxy, amino, halo, mono-N- or di-N,N-$(C_1-C_6)$alkylamino, $(C_1-C_8)$alkoxy, $(C_3-C_8)$cycloalkoxy, $(C_1-C_8)$alkyl, $(C_3-C_8)$cycloalkyl, $(C_3-C_8)$cycloalkyl$(C_1-C_8)$alkoxy or $(C_3-C_8)$cycloalkyl $(C_1-C_8)$alkyl, said $(C_1-C_8)$alkoxy, $(C_1-C_8)$cycloalkoxy, $(C_1-C_8)$alkyl, $(C_3-C_8)$cycloalkyl, $(C_3-C_8)$cycloalkyl $(C_1-C_8)$alkoxy or $(C_3-C_8)$cycloalkyl$(C_1-C_8)$alkyl optionally mono- or di-substituted with hydroxy or optionally substituted with one to nine fluorines, and pharmaceutically acceptable salts thereof.

Especially preferred compounds within the J Group of compounds are compounds wherein a. Y is 3,4-di-chlorophenyl; and R³ is 4-hydroxypiperidinyl;

b. Y is 3,4-di-chlorophenyl; and

R³ is 2-hydroxyethylpyrrolidinyl;

c. Y is 3,4-di-chlorophenyl; and

R³ is 3-hydroxypiperidinyl;

and pharmaceutically acceptable salts of said compounds.

Especially preferred compounds of Formula I are the compounds

4'-[4-(3,4-Dichloro-phenyl)-1H-imidazol-2-yl]-3,4,5,6-tetrahydro-2H-[1,2']bipyridinyl-4-ol;

2-{4'-[4-(3,4-Dichloro-phenyl)-1H-imidazol-2-yl]-3,4,5,6-tetrahydro-2H-[1,2]bipyridinyl-4-yl}-ethanol;

1-{4-[4-(3,4-Dichloro-phenyl)-1H-imidazol-2-yl]-pyridin-2-yl}-pyrrolidin-3-ol; and pharmaceutically acceptable salts of said compounds.

A preferred group of compounds, designated the K Group, contains those compounds having the Formula I as shown above wherein Y is phenyl, benzofuranyl, pyrrolyl or thiophenyl, said Y rings optionally mono- or di-substituted independently with chloro, fluoro, $(C_1-C_4)$alkoxy, hydroxy, $(C_1-C_4)$ alkyl, cyano, trifluoromethyl or trifluoromethoxy;

L is nitrogen;

M is carbon;

R³ is a four to six membered saturated mono-aza ring optionally substituted on carbon;

R³ is optionally mono- or di-substituted independently with hydroxy, oxo, amino, halo, mono-N- or di-N,N-$(C_1-C_6)$ alkylamino, mono-N- or di-N,N-$(C_3-C_6)$ cycloalkylamino, N-$(C_1-C_6)$alkyl-N-$(C_3-C_6)$ cycloalkylamino, $(C_1-C_8)$alkyl, $(C_3-C_8)$cycloalkyl, $(C_3-C_8)$cycloalkyl$(C_1-C_8)$alkyl, $(C_1-C_8)$alkoxy, $(C_3-C_8)$ cycloalkoxy or $(C_3-C_8)$cycloalkyl$(C_1-C_6)$alkoxy;

wherein said mono-N- or di-N,N-$(C_1-C_6)$alkylamino, mono-N- or di-N,N-$(C_3-C_6)$cycloalkylamino, N-$(C_1-C_6)$alkyl-N-$(C_3-C_6)$cycloalkylamino, $(C_1-C_8)$ alkyl, $(C_3-C_8)$cycloalkyl, $(C_3-C_8)$cycloalkyl$(C_1-C_8)$ alkyl, $(C_1-C_8)$alkoxy, $(C_3-C_8)$cycloalkoxy or $(C_3-C_8)$ cycloalkyl$(C_1-C_8)$alkoxy are optionally mono- or di-substituted with hydroxy and optionally substituted with one to nine fluorines; or R³ is optionally monosubstituted with a five to eight membered aromatic X ring optionally having one or two heteroatoms independently selected from nitrogen or sulfur, said X ring optionally linked through $(C_1-C_6)$alkyl or carbonyl, wherein said X ring is optionally mono-, di-, or tri-substituted independently with hydroxy, halo, $(C_3-C_6)$cycloalkyl$(C_1-C_6)$alkyl, $(C_3-C_6)$cycloalkyl $(C_1-C_6)$alkoxy, $(C_1-C_6)$alkyl, $(C_3-C_6)$cycloalkyl, $(C_1-C_6)$alkoxy or $(C_3-C_6)$cycloalkoxy;

wherein said $(C_3-C_6)$cycloalkyl$(C_1-C_6)$alkyl, $(C_3-C_6)$ cycloalkyl$(C_1-C_6)$alkoxy, $(C_1-C_6)$alkyl, $(C_3-C_6)$ cycloalkyl, $(C_1-C_6)$alkoxy or $(C_3-C_6)$cycloalkoxy moieties optionally substituted with one to nine fluorines; or $R^3$ is optionally mono-substituted with a four to seven membered saturated nitrogen containing X ring optionally having one to two additional heteroatoms selected independently from oxygen, nitrogen and sulfur, said ring linked to $R^3$ through N, said link optionally containing a $(C_1-C_6)$alkyl, and pharmaceutically acceptable salts thereof.

A group of compounds which is preferred among the K Group of compounds, designated the L Group, contains those compounds wherein $R^3$ is optionally mono-substituted with hydroxy, amino, halo, mono-N- or di-N,N-$(C_1-C_6)$alkylamino, $(C_1-C_8)$alkoxy, $(C_3-C_8)$cycloalkoxy, $(C_1-C_8)$alkyl, $(C_3-C_8)$cycloalkyl, $(C_3-C_8)$cycloalkyl$(C_1-C_8)$alkoxy or $(C_3-C_8)$cycloalkyl$(C_1-C_8)$alkyl, said mono-N- or di-N,N-$(C_1-C_6)$alkylamino, $(C_1-C_8)$alkoxy, $(C_1-C_8)$cycloalkoxy, $(C_1-C_8)$alkyl, $(C_1-C_8)$cycloalkyl, $(C_3-C_8)$cycloalkyl$(C_1-C_8)$alkoxy or $(C_3-C_8)$cycloalkyl$(C_1-C_8)$alkyl optionally mono- or di-substituted with hydroxy or optionally substituted with one to nine fluorines; or $R^3$ is optionally mono-substituted with X, wherein X is phenyl, said phenyl optionally mono-, di- or tri-substituted independently with hydroxy, halo, $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy, said $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy moieties optionally substituted with one to nine fluorines; or $R^3$ is optionally mono-substituted with a pyridyl or pyrimidyl X ring, said X ring optionally linked through carbonyl, and pharmaceutically acceptable salts thereof.

A group of compounds which is preferred among the L Group of compounds, designated the M Group, contains those compounds wherein Y is phenyl, said phenyl optionally mono- or di-substituted independently with chloro, fluoro, $(C_1-C_4)$alkoxy, hydroxy, $(C_1-C_4)$ alkyl, cyano, trifluoromethyl or trifluoromethoxy;

$R^3$ is pyrrolidinyl or piperidinyl;

$R^3$ is optionally mono-substituted with hydroxy, amino, halo, mono-N- or di-N,N-$(C_1-C_6)$alkylamino, $(C_1-C_8)$alkoxy, $(C_3-C_8)$cycloalkoxy, $(C_1-C_8)$alkyl, $(C_3-C_8)$cycloalkyl, $(C_3-C_8)$cycloalkyl$(C_1-C_8)$alkoxy or $(C_3-C_8)$cycloalkyl$(C_1-C_8)$alkyl, said $(C_1-C_8)$alkoxy, $(C_3-C_8)$cycloalkoxy, $(C_1-C_8)$alkyl, $(C_3-C_8)$cycloalkyl, $(C_3-C_8)$cycloalkyl$(C_1-C_8)$alkoxy or $(C_3-C_8)$cycloalkyl$(C_1-C_8)$alkyl optionally mono- or di-substituted with hydroxy or optionally substituted with one to nine fluorines; or $R^3$ is optionally mono-substituted with phenyl, said phenyl optionally mono-substituted with hydroxy,$(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy, said $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy moieties optionally substituted with one to nine fluorines, and pharmaceutically acceptable salts thereof.

A group of compounds which is preferred among the M Group of compounds, designated the N Group, contains those compounds wherein $R^3$ is pyrrolidinyl or piperidinyl;

$R^3$ is optionally mono-substituted with hydroxy, amino, halo, mono-N- or di-N,N-$(C_1-C_6)$alkylamino, $(C_1-C_8)$alkoxy, $(C_3-C_8)$cycloalkoxy, $(C_1-C_8)$alkyl, $(C_3-C_8)$cycloalkyl, $(C_3-C_8)$cycloalkyl$(C_1-C_8)$alkoxy or $(C_3-C_8)$cycloalkyl$(C_1-C_8)$alkyl, said $(C_1-C_8)$alkoxy, $(C_3-C_8)$cycloalkoxy, $(C_1-C_8)$alkyl, $(C_3-C_8)$cycloalkyl, $(C_3-C_8)$cycloalkyl$(C_1-C_8)$alkoxy or $(C_3-C_8)$cycloalkyl$(C_1-C_8)$alkyl optionally mono- or di-substituted with hydroxy or optionally substituted with one to nine fluorines, and pharmaceutically acceptable salts thereof.

Especially preferred compounds within the N Group of compounds are compounds wherein a. Y is 3,4-di-chlorophenyl; and $R^3$ is 4-hydroxypiperidinyl;

b. Y is 3,4-di-chlorophenyl; and $R^3$ is 3-isobutylaminopyrrolidinyl; and pharmaceutically acceptable salts of said compounds.

Especially preferred compounds of Formula I are the compounds:

5'-[4-(3,4-Dichloro-phenyl)-1H-imidazol-2-yl]-3,4,5,6-tetrahydro-2H-[1,2]bipyridinyl-4-ol;

(1-{5-[4-(3,4-Dichloro-phenyl)-1H-imidazol-2-yl]-pyridin-2-yl}-pyrrolidin-3-yl)-isobutyl-amine; and pharmaceutically acceptable salts of said compounds.

A preferred group of compounds, designated the O Group, contains those compounds having the Formula I as shown above wherein Y is phenyl, benzofuranyl, pyrrolyl or thiophenyl, said Y rings optionally mono- or di-substituted independently with chloro, fluoro, $(C_1-C_4)$alkoxy, hydroxy, $(C_1-C_4)$alkyl, cyano, trifluoromethyl or trifluoromethoxy;

L is carbon;

M is nitrogen;

$R^3$ is a five to seven membered diaza mono- or di-substituted saturated ring;

wherein $R^3$ is optionally mono- or di-substituted independently on carbon with hydroxy, amino, halo, mono-N- or di-N,N-$(C_1-C_6)$alkylamino, mono-N- or di-N,N-$(C_3-C_6)$cycloalkylamino, N-$(C_1-C_6)$alkyl-N-$(C_3-C_6)$cycloalkylamino, $(C_1-C_8)$alkyl, $(C_3-C_8)$cycloalkyl, $(C_3-C_8)$cycloalkyl$(C_1-C_8)$alkyl, $(C_1-C_8)$alkoxy, $(C_3-C_8)$cycloalkoxy or $(C_3-C_8)$cycloalkyl$(C_1-C_8)$alkoxy;

wherein said mono-N- or di-N,N-$(C_1-C_6)$alkylamino, mono-N- or di-N,N-$(C_3-C_6)$cycloalkylamino, N-$(C_1-C_6)$alkyl-N-$(C_3-C_6)$cycloalkylamino, $(C_1-C_6)$alkyl, $(C_3-C_8)$cycloalkyl, $(C_3-C_8)$cycloalkyl$(C_1-C_8)$alkyl, $(C_1-C_8)$alkoxy, $(C_3-C_8)$cycloalkoxy or $(C_3-C_8)$cycloalkyl$(C_1-C_8)$alkoxy are optionally mono- or di-substituted with hydroxy and optionally substituted with one to nine fluorines; or $R^3$ is optionally mono-substituted on carbon with a five to eight membered aromatic X ring optionally having one heteroatom selected from nitrogen or sulfur, said X ring optionally linked through $(C_1-C_6)$alkyl, wherein said X ring is optionally mono-, di-, or tri-substituted independently with hydroxy, halo, $(C_3-C_6)$cycloalkyl$(C_1-C_6)$alkyl, $(C_3-C_6)$cycloalkyl$(C_1-C_6)$alkoxy, $(C_1-C_6)$alkyl, $(C_3-C_6)$cycloalkyl, $(C_1-C_6)$alkoxy or $(C_3-C_6)$cycloalkoxy;

wherein said $(C_3-C_6)$cycloalkyl$(C_1-C_6)$alkyl, $(C_3-C_6)$cycloalkyl$(C_1-C_6)$alkoxy, $(C_1-C_6)$alkyl, $(C_3-C_6)$cycloalkyl, $(C_1-C_6)$alkoxy or $(C_3-C_6)$cycloalkoxy moieties areoptionally substituted with one to nine fluorines; or $R^3$ is optionally mono-substituted on carbon with an X ring linked through carbonyl, wherein X is phenyl, furanyl or thiophenyl, wherein said X ring is optionally mono, di-, or tri-subsfituted independently with hydroxy, halo, $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy, said $(C_3-C_6)$cycloalkyl$(C_1-C_6)$alkyl, $(C_3-C_6)$cycloalkyl$(C_1-C_6)$alkoxy, $(C_1-C_6)$alkyl, $(C_3-C_6)$cycloalkyl, $(C_1-C_6)$alkoxy or $(C_3-C_6)$cycloalkoxy moieties optionally substituted with one to nine fluoros; or $R^3$ is optionally monosubstituted on carbon with a four to seven membered saturated nitrogen containing X ring optionally having one to two additional heteroatoms selected independently from oxygen, nitrogen and sulfur, said ring linked to $R^3$ through N, said link optionally containing a $(C_1-C_8)$alkyl; and $R^3$ is optionally mono-substituted on nitrogen with $(C_1-C_8)$alkyl, $(C_3-C_8)$cycloalkyl or $(C_3-C_8)$cycloalkyl$(C_1-C_8)$alkyl;

wherein said $(C_1-C_8)$alkyl, $(C_3-C_8)$cycloalkyl or $(C_3-C_8)$cycloalkyl$(C_1-C_8)$alkyl are optionally mono- or di-substituted independently with hydroxy and optionally substituted with one to nine fluorines; or $R^3$ is optionally mono-substituted on nitrogen with a carbonyl linked T ring wherein said T ring is phenyl, furanyl or thiophenyl, wherein said ring is optionally mono-, di-, or tri-substituted independently with hydroxy, halo, $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy, said $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_1-C_6)$cycloalkoxy moieties optionally substituted with one to nine fluorines; or $R^3$ is optionally mono-substituted on nitrogen with a five to eight membered aromatic T ring optionally having one or two heteroatoms selected independently from nitrogen or sulfur, said T ring optionally linked through $(C_1-C_6)$alkyl, wherein said T ring is optionally mono-, di-, or tri-substituted independently with hydroxy, halo, $(C_3-C_6)$cycloalkyl$(C_1-C_6)$alkyl, $(C_3-C_6)$cycloalkyl$(C_1-C_6)$alkoxy, $(C_1-C_6)$alkyl, $(C_3-C_6)$cycloalkyl, $(C_1-C_6)$alkoxy or $(C_3-C_6)$cycloalkoxy;

wherein said $(C_3-C_6)$cycloalkyl$(C_1-C_6)$alkyl, $(C_3-C_6)$cycloalkyl$(C_1-C_6)$alkoxy, $(C_1-C_6)$alkyl, $(C_3-C_6)$cycloalkyl, $(C_1-C_6)$alkoxy or $(C_3-C_6)$cycloalkoxy moieties are optionally substituted with one to nine fluorines; and pharmaceutically acceptable salts thereof.

A group of compounds which is preferred among the O Group of compounds, designated the P Group, contains those compounds wherein $R^3$ is a five to seven membered diaza saturated ring mono-substituted on carbon;

wherein $R^3$ is optionally mono-substituted with hydroxy, amino, halo, mono-N- or di-N,N-$(C_1-C_6)$alkylamino, $(C_1-C_8)$alkoxy, $(C_3-C_8)$cycloalkoxy, $(C_1-C_8)$alkyl, $(C_3-C_8)$cycloalkyl, $(C_3-C_8)$cycloalkyl$(C_1-C_8)$alkoxy or $(C_3-C_8)$cycloalkyl$(C_1-C_8)$alkyl, said $(C_1-C_8)$alkoxy, $(C_3-C_8)$cycloalkoxy, $(C_1-C_8)$alkyl, $(C_3-C_8)$cycloalkyl, $(C_3-C_8)$cycloalkyl$(C_1-C_8)$alkoxy or $(C_3-C_8)$cycloalkyl$(C_1-C_8)$alkyl optionally mono- or di-substituted with hydroxy or optionally substituted with one to nine fluorines; or $R^3$ is optionally mono-substituted with phenyl, said phenyl optionally mono-substituted with hydroxy,$(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy, said $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy moieties optionally substituted with one to nine fluorines, and pharmaceutically acceptable salts thereof.

A group of compounds which is preferred among the O Group of compounds, designated the Q Group, contains those compounds wherein $R^3$ is a five to seven membered diaza saturated ring, said ring mono-substituted on carbon and mono-substituted on nitrogen;

wherein $R^3$ is optionally mono-substituted on nitrogen with $(C_1-C_8)$alkyl, $(C_3-C_8)$cycloalkyl or $(C_3)$cycloalkyl$(C_1-C_8)$alkyl wherein said $(C_1-C_8)$alkyl, $(C_3-C_8)$cycloalkyl or $(C_3-C_8)$cycloalkyl$(C_1-C_8)$alkyl are optionally mono-, di- or tri-substituted independently with hydroxy, halo, $(C_1-C_6)$cycloalkyl; or $R^3$ is optionally mono-substituted on nitrogen with phenyl, said phenyl optionally linked through $(C_1-C_6)$alkyl, said phenyl optionally mono-, di-, or tri-substituted independently with hydroxy, halo, $(C_3-C_6)$cycloalkyl$(C_1-C_6)$alkyl, $(C_3-C_6)$cycloalkyl$(C_1-C_6)$alkoxy, $(C_1-C_6)$alkyl, $(C_3-C_6)$cycloalkyl, $(C_1-C_6)$alkoxy or $(C_3-C_6)$cycloalkoxy;

wherein said $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy moieties are optionally substituted with one to nine fluorines; or $R^3$ is optionally mono-substituted on nitrogen with a pyridyl or pyrimidyl ring, said pyridyl or pyrimidyl ring optionally linked through $(C_1-C_6)$alkyl; or $R^3$ is mono-substituted on carbon with hydroxy, amino, halo, mono-N- or di-N,N-$(C_1-C_6)$alkylamino, $(C_1-C_8)$alkoxy, $(C_3-C_8)$cycloalkoxy, $(C_1-C_8)$alkyl, $(C_3-C_8)$cycloalkyl, $(C_3-C_8)$cycloalkyl$(C_1-C_8)$alkoxy or $(C_3-C_8)$cycloalkyl$(C_1-C_8)$alkyl, said $(C_1-C_8)$alkoxy, $(C_3-C_3)$cycloalkoxy, $(C_1-C_8)$alkyl, $(C_3-C_8)$cycloalkyl, $(C_3-C_8)$cycloalkyl$(C_1-C_8)$alkoxy or $(C_3-C_8)$cycloalkyl$(C_1-C_8)$alkyl optionally mono- or di-substituted with hydroxy or optionally substituted with one to nine fluorines, and pharmaceutically acceptable salts thereof.

A preferred group of compounds, designated the R Group, contains those compounds having the Formula I as shown above wherein Y is phenyl, benzofuranyl, pyrrolyl or thiophenyl, said Y ring optionally mono- or di-substituted independently with chloro, fluoro, $(C_1-C_4)$alkoxy, hydroxy, $(C_1-C_4)$alkyl, cyano, trifluoromethyl or trifluoromethoxy;

L is nitrogen;

M is carbon;

$R^3$ is a five to seven membered diaza mono- or di-substituted saturated ring;

wherein $R^3$ is optionally mono- or di-substituted independently on carbon with hydroxy, amino, halo, mono-N- or di-N,N-$(C_1-C_6)$alkylamino, mono-N- or di-N,N-$(C_3-C_6)$cycloalkylamino, N-$(C_1-C_6)$alkyl-N-$(C_3-C_6)$cycloalkylamino, $(C_1-C_8)$alkyl, $(C_3-C_8)$cycloalkyl, $(C_3-C_8)$cycloalkyl$(C_1-C_8)$alkyl, $(C_1-C_8)$alkoxy, $(C_3-C_8)$cycloalkoxy or $(C_3-C_8)$cycloalkyl$(C_1-C_8)$alkoxy;

wherein said mono-N- or di-N,N-$(C_1-C_6)$alkylamino, mono-N- or di-N,N-$(C_3-C_6)$cycloalkylamino, N-($C_1$–$C_8$)alkyl-N-($C_3$–$C_8$)cycloalkylamino, ($C_1$–$C_8$) alkyl, ($C_3$–$C_{83}$)cycloalkyl, ($C_3$–$C_8$)cycloalkyl($C_1$–$C_8$) alkyl, ($C_1$–$C_8$)alkoxy, ($C_3$–$C_8$)cycloalkoxy or ($C_3$–$C_8$) cycloalkyl($C_1$–$C_8$)alkoxy are optionally mono- or di-substituted with hydroxy and optionally substituted with one to nine fluorines; or $R^3$ is optionally mono-substituted on carbon with a five to eight membered aromatic X ring optionally having one heteroatom selected from nitrogen or sulfur, said X ring optionally linked through ($C_1$–$C_6$)alkyl, wherein said X ring is optionally mono-, di-, or tri-substituted independently with hydroxy, halo, ($C_3$–$C_6$)cycloalkyl($C_1$–$C_6$)alkyl, ($C_3$–$C_6$)cycloalkyl($C_1$–$C_6$)alkoxy, ($C_1$–$C_6$)alkyl, ($C_3$–$C_6$)cycloalkyl, ($C_1$–$C_6$)alkoxy or ($C_3$–$C_6$)cycloalkoxy;

wherein said ($C_3$–$C_6$)cycloalkyl($C_1$–$C_6$)alkyl, ($C_3$–$C_6$) cycloalkyl($C_1$–$C_6$)alkoxy, ($C_1$–$C_6$)alkyl, ($C_3$–$C_6$) cycloalkyl, ($C_1$–$C_6$)alkoxy or ($C_3$–$C_6$)cycloalkoxy moieties are optionally substituted with one to nine fluorines;

$R^3$ is optionally mono-substituted on carbon with an X ring inked through carbonyl, wherein X is phenyl, furanyl or thiophenyl, wherein said X ring is optionally mono-, di-, or tri-substituted independently with hydroxy, halo, ($C_3$–$C_6$) cycloalkyl($C_1$–$C_6$)alkyl, ($C_3$–$C_6$)cycloalkyl($C_1$–$C_6$) alkoxy,($C_1$–$C_6$)alkyl, ($C_3$–$C_6$)cycloalkyl, ($C_1$–$C_6$) alkoxy or ($C_3$–$C_6$)cycloalkoxy, said ($C_1$–$C_6$)cycloalkyl ($C_1$–$C_6$)alkyl, ($C_3$–$C_6$)cycloalkyl($C_1$–$C_6$)alkoxy, ($C_1$–$C_6$)alkyl, ($C_3$–$C_6$)cycloalkyl, ($C_1$–$C_6$)alkoxy or ($C_1$–$C_6$)cycloalkoxy moieties optionally substituted with one to nine fluoros; or $R^3$ is optionally mono-substituted on carbon with a four to seven membered saturated nitrogen containing X ring optionally having one to two additional heteroatoms selected independently from oxygen, nitrogen and sulfur, said ring linked to $R^3$ through N, said link optionally containing a ($C_1$–$C_6$)alkyl; and $R^3$ is optionally mono-substituted on nitrogen with ($C_1$–$C_8$) alkyl, ($C_3$–$C_8$)cycloalkyl or ($C_3$–$C_8$)cycloalkyl($C_1$–$C_8$) alkyl;

wherein said ($C_1$–$C_8$)alkyl, ($C_3$–$C_8$)cycloalkyl or ($C_3$–$C_8$) cycloalkyl($C_1$–$C_8$)alkyl are optionally mono- or di-substituted with hydroxy and optionally substituted with one to nine fluorines; or $R^3$ is optionally mono-substituted on nitrogen with a carbonyl linked T ring wherein said T ring is phenyl, furanyl or thiophenyl, wherein said ring is optionally mono-, di-, or tri-substituted independently with hydroxy, halo, ($C_1$–$C_6$)cycloalkyl($C_1$–$C_6$)alkyl, ($C_3$–$C_6$)cycloalkyl($C_1$–$C_6$)alkoxy,($C_1$–$C_6$)alkyl, ($C_3$–$C_6$)cycloalkyl, ($C_1$–$C_6$)alkoxy or ($C_1$–$C_6$) cycloalkoxy, said ($C_3$–$C_6$)cycloalkyl($C_1$–$C_6$)alkyl, ($C_3$–$C_6$)cycloalkyl($C_1$–$C_6$)alkoxy,($C_1$–$C_6$)alkyl, ($C_3$–$C_6$)cycloalkyl, ($C_1$–$C_6$)alkoxy or ($C_3$–$C_6$) cycloalkoxy moieties optionally substituted with one to nine fluoros; or $R^3$ is optionally mono-substituted on nitrogen with a five to eight membered aromatic T ring optionally having one or two heteroatoms independently selected from nitrogen or sulfur, said T ring optionally linked through ($C_1$–$C_6$)alkyl, wherein said T ring is optionally mono-, di-, or tri-substituted independently with hydroxy, halo, ($C_3$–$C_6$) cycloalkyl($C_1$–$C_6$)alkyl, ($C_3$–$C_6$)cycloalkyl($C_1$–$C_6$) alkoxy, ($C_1$–$C_6$)alkoxy, ($C_1$–$C_6$)Cycloalkyl, ($C_1$–$C_6$) alkoxy or ($C_3$–$C_6$)cycloalkoxy;

wherein said ($C_3$–$C_6$)cycloalkyl($C_1$–$C_6$)alkyl, ($C_{1–C_6}$) cycloalkyl($C_1$–$C_6$)alkoxy, ($C_1$–$C_6$)alkyl, ($C_3$–$C_6$) cycloalkyl, ($C_1$–$C_6$)alkoxy or ($C_3$–$C_6$)cycloalkoxy moieties optionally substituted with one to nine fluorines; and pharmaceutically acceptable salts thereof.

A group of compounds which is preferred among the R Group of compounds, designated the S Group, contains those compounds wherein $R^3$ is a five to seven membered diaza saturated ring mono-substituted on carbon;

wherein $R^3$ is optionally mono-substituted with hydroxy, amino, halo, mono-N- or di-N,N-($C_1$–$C_6$)alkylamino, ($C_1$–$C_8$) alkoxy, ($C_3$–$C_8$)cycloalkoxy, ($C_1$–$C_8$)alkyl, ($C_3$–$C_8$) cycloalkyl, ($C_3$–$C_8$)cycloalkyl($C_1$–$C_8$)alkoxy or ($C_3$–$C_8$) cycloalkyl($C_1$–$C_8$)alkyl, said ($C_1$–$C_8$)alkoxy, ($C_3$–$C_8$) cycloalkoxy, ($C_1$–$C_8$)alkyl, ($C_3$–$C_8$)cycloalkyl, ($C_3$–$C_8$) cycloalkyl($C_1$–$C_8$)alkoxy or ($C_3$–$C_8$)cycloalkyl($C_1$–$C_8$) alkyl optionally mono- or di-substituted with hydroxy or optionally substituted withone to nine fluorines; or $R^3$ is optionally mono-substituted with phenyl, said phenyl optionally mono-substituted with hydroxy,($C_3$–$C_6$) cycloalkyl($C_1$–$C_6$)alkyl, ($C_3$–$C_6$)cycloalkyl($C_1$–$C_3$) alkoxy,($C_1$–$C_6$)alkyl, ($C_3$–$C_6$)cycloalkyl, ($C_1$–$C_6$)alkoxy or ($C_3$–$C_6$)cycloalkoxy, said ($C_3$–$C_8$)cycloalkyl($C_1$–$C_6$) alkyl, ($C_3$–$C_6$)cycloalkyl($C_1$–$C_6$)alkoxy,($C_1$–$C_6$)alkyl, ($C_3$–$C_6$)cycloalkyl, ($C_1$–$C_6$)alkoxy or ($C_3$–$C_6$) cycloalkoxy moieties optionally substituted with one to nine fluorines, and pharmaceutically acceptable salts thereof.

A group of compounds which is preferred among the S Group of compounds, designated the T Group, contains those compounds wherein $R^3$ is a five to seven membered diaza saturated ring, said ring mono-substituted on carbon and mono-substituted on nitrogen; wherein $R^3$ is optionally mono-substituted on nitrogen with ($C_1$–$C_8$)alkyl, ($C_3$–$C_8$)cycloalkyl or ($C_1$–$C_8$)cycloalkyl($C_1$–$C_8$)alkyl wherein said ($C_1$–$C_8$) alkyl, ($C_3$–$C_8$)cycloalkyl or ($C_3$–$C_8$)cycloalkyl($C_1$–$C_8$) alkyl are optionally mono-, di- or tri-substituted independently with hydroxy, halo, ($C_1$–$C_6$)cycloalkyl; or $R^3$ is optionally monosubstituted on nitrogen with phenyl, said phenyl optionally linked through ($C_1$–$C_6$)alkyl, said phenyl optionally mono-, di-, or tri-substituted independently with hydroxy, halo, ($C_3$–$C_6$)cycloalkyl($C_1$–$C_6$) alkyl, ($C_3$–$C_6$)cycloalkyl($C_1$–$C_6$)alkoxy,($C_1$–$C_6$)alkyl, ($C_3$–$C_6$)cycloalkyl, ($C_1$–$C_6$)alkoxy or ($C_3$–$C_6$) cycloalkoxy;

wherein said ($C_3$–$C_6$)cycloalkyl($C_1$–$C_8$)alkyl, ($C_3$–$C_6$) cycloalkyl($C_1$–$C_6$)alkoxy,($C_1$–$C_6$)alkyl, ($C_3$–$C_6$) cycloalkyl, ($C_1$–$C_6$)alkoxy or ($C_3$–$C_6$)cycloalkoxy moieties are optionally substituted with one to nine fluorines; or $R^3$ is optionally mono-substituted on nitrogen with a pyridyl or pyrimidyl ring, said pyridyl or pyrimidyl ring optionally linked through ($C_1$–$C_6$)alkyl; and $R^3$ is mono-substituted on carbon with hydroxy, amino, halo, mono-N- or di-N,N-($C_1$–$C_6$)alkylamino, ($C_1$–$C_8$)alkoxy, ($C_3$–$C_8$)cycloalkoxy, ($C_1$–$C_8$)alkyl, ($C_3$–$C_8$)cycloalkyl, ($C_3$–$C_8$)cycloalkyl($C_1$–$C_8$)alkoxy or ($C_3$–$C_8$)cycloalkyl ($C_1$–$C_8$)alkyl, said ($C_1$–$C_8$)alkoxy, ($C_3$–$C_8$)cycloalkoxy, ($C_1$–$C_8$)alkyl, ($C_3$–$C_8$)cycloalkyl, ($C_3$–$C_8$)cycloalkyl ($C_1$–$C_8$)alkoxy or ($C_3$–$C_8$)cycloalkyl($C_1$–$C_8$)alkyl optionally mono- or di-substituted with hydroxy or optionally substituted with one to nine fluorines, and pharmaceutically acceptable salts thereof.

An especially preferred compound within the T Group of compounds is the compound wherein Y is 4-fluorophenyl; and $R^3$ is 4-isobutyl-3-methylpiperazinyl; and pharmaceutically acceptable salts thereof.

An especially preferred compound of Formula I is the compound 4-{5-[4-(4-Fluoro-phenyl)-1H-imidazol-2-yl]-pyridin-2-yl}-1-isobutyl-2-methyl-piperazine and pharmaceutically acceptable salts thereof.

A preferred group of compounds, designated the U Group, contains those compounds having the Formula I as shown above wherein L is carbon;

M is nitrogen;

$R^3$ is piperazinyl, wherein the additional optional ring nitrogen is substituted as described above for the Formula I compounds; and Y is phenyl optionally substituted with a maximum of three substituents selected independently from Group I, Group II, and Group III and pharmaceutically acceptable salts thereof.

A preferred group of compounds, designated the V Group, contains those compounds having the Formula I as shown above wherein L is nitrogen;

M is carbon;

$R^3$ is piperazinyl, wherein the additional optional ring nitrogen is substituted as described above for the Formula I compounds; and Y is phenyl optionally substituted with a maximum of three substituents selected independently from Group I, Group II, and Group III and pharmaceutically acceptable salts thereof.

Another aspect of this invention is directed to compounds of Formula LXX

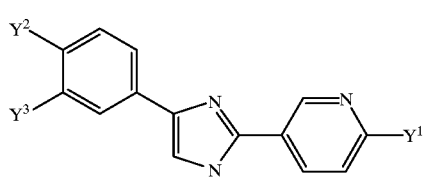

LXX wherein $Y^1$ is halo, mesylate, p-tosylate, nosylate, piperazinyl or besylate; and $Y_2$ and $Y_3$ are independently H, halo, $(C_1–C_6)$alkyl, $(C_3–C_6)$ cycloalkyl, cyano, $(C_1–C_6)$alkoxy, or $(C_3–C_6)$ cycloalkoxy, said $Y_2$ and $Y_3$ substituents optionally substituted with from one to nine fluorines.

A preferred group of compounds, designated the M Group, contains those compounds having the Formula LXX as shown above wherein $Y^1$ is halo; and $Y^2$ and $Y^3$ are independently H, chloro, fluoro, $(C_1–C_6)$ alkyl, $(C_1–C_6)$alkoxy, or cyano, said $(C_1–C_6)$alkyl or $(C_1–C_6)$alkoxy $Y^2$ and $Y^3$ substituents optionally substituted with from one to three fluorines.

Especially preferred compounds of Formula LXX are the compounds wherein a. $Y^1$ is chloro; and
$Y^2$ and $Y^3$ are chloro;

b. $Y^1$ is chloro; and
$Y^2$ is chloro and $Y^3$ is fluoro;

c. $Y^1$ is chloro; and
$Y^2$ is H and $Y^3$ is cyano;

d. $Y^1$ is piperazinyl; and
$Y^2$ and $Y^3$ are chloro;

e. $Y^1$ is piperazinyl; and
$Y^2$ is chloro and $Y^3$ is fluoro;

f. $Y^1$ is piperazinyl; and
$Y^2$ is H and $Y^3$ is cyano.

Another aspect of this invention is a method of treating a mammal (e.g., human, dogs, cats and horses) having a disease or condition mediated by NPY by administering a therapeutically effective amount of a compound of Formula I, a prodrug thereof, or a pharmaceutically acceptable salt of said compound or of said prodrug to the mammal. It is preferred that the receptor is the NPY-5 receptor.

A preferred dosage is about 0.001 to 100 mg/kg/day of the Formula I compound or a prodrug thereof. An especially preferred dosage is about 0.01 to 50 mg/kg/day of a compound of Formula I, a prodrug thereof, or a pharmaceutically acceptable salt of said compound or of said prodrug.

Another aspect of this invention is directed to a method of treating obesity comprising administering to a mammal (e.g., a female or male human) in need of such treatment a therapeutically effective amount of a compound of Formula I or a prodrug thereof, or a pharmaceutically acceptable salt of said compound or of said prodrug.

Another aspect of this invention is directed to a method for treating eating and metabolic disorders such as bulimia and anorexia comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating hyperlipidemia comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating cellulite and fat accumulation comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating type II diabetes comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating diseases related to the heart, blood vessels or renal system comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating a vasospasm comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating heart failure comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating shock comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating cardiac hypertrophy comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating increased blood pressure comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating angina comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating myocardial infarction comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating sudden cardiac death comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating arrythmia comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating peripheral vascular disease comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating an abnormal renal condition such as impaired flow of fluid or abnormal mass transport comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating renal failure comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating conditions related to increased sympathetic nerve activity for example, during or after coronary artery surgery, and operations and surgery in the gastrointestinal tract comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating cerebral diseases and diseases related to the central nervous system comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating cerebral infarction comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating neurodegeneration comprising administering to a mammal (e.g., a female or male human) a therapeutically effective amount of a compound of Formula 1, a prodrug thereof, or a pharmaceutically acceptable salt of said compound or of said prodrug.

Another aspect of this invention is directed to a method for treating impaired cognition comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating Alzheimer's disease comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating epilepsy comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating seizures comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating stroke comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating conditions related to stroke comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating cerebral vasospasm comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating cerebral hemorrhage comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating depression comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating anxiety comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating schizophrenia comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating dementia comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating addiction and/or substance abuse including nicotine, cocaine and alcohol abuse comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating attention deficit disorder comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating sleep disorders comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating seasonal affective disorder comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating conditions related to pain or nociception comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating migraine comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating disorders related to disruption of circadian rhythms including jet lag comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating diseases related to abnormal gastrointestinal motility and secretion comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating different forms of ileus comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating diarrhea and/or fecal incontinence comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating a gastric ulcer comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating neurogenic voiding dysfunction comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating urinary incontinence comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating Crohn's disease comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating irritable bowel syndrome comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating inflammatory bowel disease comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating nausea comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating emesis comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating sexual dysfunction comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating reproductive disorders comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for altering fertility comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating conditions or disorders associated with inflammation comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating respiratory diseases comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating asthma comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating conditions related to asthma comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating bronchoconstriction comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating nasal congestion, allergies or seasonal allergies comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating diseases related to abnormal hormone release comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating abnormal luteinizing hormone release comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating abnormal growth hormone release comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating abnormal insulin release comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating abnormal prolactin release comprising administering to a mammal (e.g., a female or male human) a therapeutically effective amount of a compound of Formula I, a prodrug thereof, or a pharmaceutically acceptable salt of said compound or of said prodrug.

In addition to the "direct" effect of the compounds of this invention on the NPY5 subtype there are diseases/conditions that will benefit from the weight loss such as insulin resistance, impaired glucose tolerance, Type II Diabetes, hypertension, hyperlipidemia, cardiovascular disease, gall stones, certain cancers, sleep apnea, etc.

This invention is also directed to pharmaceutical compositions which comprise an amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of obesity which comprise an obesity treating amount of a compound of Formula I, a prodrug thereof, or a pharmaceutically acceptable salt of said compound or of said prodrug and a pharmaceutically acceptable vehicle, diluent or carrier.

In the above pharmaceutical compositions and methods preferred Formula I compounds include the preferred groups of compounds described above labeled as Group A- to Group V.

Yet another aspect of this invention is combinations of a compound of Formula I, a prodrug thereof, or a pharmaceutically acceptable salt of said compound or of said prodrug and other compounds as described below.

Accordingly, another aspect of this invention is a method for treating obesity comprising administering to a mammal (e.g., a female or male human)
  a. an amount of a first compound, said first compound being a Formula I compound, a prodrug thereof, or a pharmaceutically acceptable salt of said compound or of said prodrug; and
  b. an amount of a second compound, said second compound being a $\beta_3$ agonist, a thyromimetic agent, an eating behavior modifying agent, or a NPY antagonist wherein the amounts of the first and second compounds result in a therapeutic effect.

This invention is also directed to a pharmaceutical combination composition comprising: a therapeutically effective amount of a composition comprising
  a first compound, said first compound being a Formula I compound, a prodrug thereof, or a pharmaceutically acceptable salt of said compound or of said prodrug;
  a second compound, said second compound being a β3 agonist, a thyromimetic agent, an eating behavior modifying agent, or a NPY antagonist; and/or optionally
  a pharmaceutical carrier, vehicle or diluent.

Another aspect of this invention is a kit comprising:
  a. an amount of a Formula I compound, a prodrug thereof, or a pharmaceutically acceptable salt of said compound or of said prodrug and a pharmaceutically acceptable carrier, vehicle or diluent in a first unit dosage form;
  b. an amount of a $\beta_3$ agonist, a thyromimetic agent, an eating behavior modifying agent, or a NPY antagonist and a pharmaceutically acceptable carrier, vehicle or diluent in a second unit dosage form; and
  c. means for containing said first and second dosage forms wherein the amounts of the first and second compounds result in a therapeutic effect.

Preferred antiobesity agents (taken singly or in any combination thereof) in the above combination methods, combination compositions and combination kits are described below.

The following are anorectic and/or antiobesity agents: phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotoninergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glycagon-like peptide-1 receptor and ciliary neurotrophic factors such as Axokine.

Particularly preferred antiobesity agents in the above combination methods, combination compositions and combination kits are sibutramine, fenfluramine, dexfenfluramine, bromocriptine, phentermine, ephedrine and leptin.

Preferred antiobesity $\beta_3$-agonists in the above combination methods, combination compositions and combination kits are:
{4-[2-(2-[6-aminopyridin-3-y]-2(R)-hydroxyethylamino)ethoxy]phenyl}acetic acid,
4-{2-[2-(6-aminopyridin-3-yl)-2(R)-hydroxyethylamino]ethoxy}benzoic acid,
{4-[2-(2-[6-aminopyridin-3-yl]-2(R)-hydroxyethylamino)ethoxy]phenyl}propionic acid,
or {4-[2-(2-[6-aminopyridin-3-yl]-2(R)-hydroxyethylamino)ethoxy]phenoxy}acetic acid.

Another aspect of this invention is a method treating diabetes comprising administering to a mammal (e.g., a female or male human)
  a. an amount of a first compound, said first compound being a Formula I compound, a prodrug thereof, or a pharmaceutically acceptable salt of said compound or of said prodrug; and
  b. an amount of a second compound, said second compound being an aldose reductase inhibitor, a glycogen phosphorylase inhibitor, a sorbitol dehydrogenase inhibitor, insulin, metformin, acarbose, a thiazolidinedione such as troglitazone, rezulin, a glitazone such as rosaglitazone or pioglitazone, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising
  a first compound, said first compound being a Formula I compound, a prodrug thereof, or a pharmaceutically acceptable salt of said compound or of said prodrug;
  a second compound, said second compound being an aldose reductase inhibitor, a glycogen phosphorylase inhibitor, a sorbitol dehydrogenase inhibitor, insulin, metformin, acarbose, a thiazolidinedione such as troglitazone, rezulin, a glitazone such as rosaglitazone or pioglitazone, a sulfonylurea, glipazide, glyburide, or chlorpropamide; and optionally
  a pharmaceutical carrier, vehicle or diluent.

Another aspect of this invention is a kit comprising:
  a. an amount of a Formula I compound, a prodrug thereof, or a pharmaceutically acceptable salt of said compound or of said prodrug and a pharmaceutically acceptable carrier, vehicle or diluent in a first unit dosage form;
  b. an amount of an aldose reductase inhibitor, a glycogen phosphorylase inhibitor, a sorbitol dehydrogenase inhibitor, insulin, metformin, acarbose, a thiazolidinedione such as troglitazone, rezulin, a glitazone such as rosaglitazone or pioglitazone, a sulfonylurea, glipazide, glyburide, or chlorpropamide and a pharmaceutically acceptable carrier, vehicle or diluent in a second unit dosage form; and
  c. means for containing said first and second dosage forms wherein the amounts of the first and second compounds result in a therapeutic effect.

In the above combination methods, combination compositions and kits a preferred aldose reductase inhibitor is 1-phthalazineacetic acid, 3,4-dihydro-4-oxo-3-[[5-trifluoromethyl)-2-benzothiazolyl]methyl]- or a pharmaceutically acceptable salt thereof.

In the above combination compositions, combination methods and kits preferred glycogen phosphorylase inhibitors (taken singly or in any combination) are
  5-chloro-1H-indole-2-carboxylic acid [(1S)-((R)-hydroxy-dimethylcarbamoyl-methyl)-2-phenyl-ethyl]-amide,
  5,6-dichloro-1H-indole-2-carboxylic acid {(1S)-[(R)-hydroxy-(methoxy-methyl-carbamoyl)-methyl]-2-phenyl-ethyl}-amide,
  5-chloro-1H-indole-2-carboxylic acid {(1S)-[(R)-hydroxy-(methoxy-methyl-carbamoyl)-methyl]-2-phenyl-ethyl}-amide,
  5-chloro-1H-indole-2-carboxylic acid ((1S)-{(R)-hydroxy-[(2-hydroxy-ethyl)-methyl-carbamoyl]-methyl}-2-phenyl-ethyl)-amide,
  5-chloro-1H-indole-2-carboxylic acid {(1S)-[(R)-hydroxy-(methyl-pyridin-2-yl-carbamoyl)-methyl]-2-phenyl-ethyl}-amide or
  5-chloro-1H-indole-2-carboxylic acid ((1S)-{(R)-hydroxy-[methyl-(2-pyridin-2-yl-ethyl)-carbamoyl]-methyl}-2-phenyl-ethyl)-amide.

5-chloro-1H-indole-2-carboxylic acid [(1S)-benzyl-(2R)-hydroxy-3-(4-methyl-piperazin-1-yl)-3-oxo-propyl]-amide hydrochloride, 5-chloro-1H-indole-2-carboxylic acid [(1S)-benzyl-(2R)-hydroxy-3-(3-hydroxy-azetidin-1-yl)-3-oxo-propyl]-amide, 5-chloro-1H-indole-2-carboxylic acid ((1S)-benzyl-(2R)-hydroxy-3-isoxazolidin-2-yl-3-oxo-propyl)-amide, 5-Chloro-1H-indole-2-carboxylic acid ((1S)-benzyl-(2R)-hydroxy-3-[1,2]oxazinan-2-yl-3-oxo-propyl)-amide, 5-chloro-1H-indole-2-carboxylic acid [(1S)-benzyl-(2R)-hydroxy-3-((3S)-hydroxy-pyrrolidin-1-yl)-3-oxo-propyl]-amide, 5-chloro-1H-indole-2-carboxylic acid [(1S)-benzyl-3-((3S,4S)-dihydroxy-pyrrolidin-1-yl)-(2R)-hydroxy-3-oxo-propyl]-amide, 5-chloro-1H-indole-2-carboxylic acid [(1S)-benzyl-3-((3R,4S)-dihydroxy-pyrrolidin-1-yl)-(2R)-hydroxy-3-oxo-propyl]-amide or 5-chloro-1H-indole-2-carboxylic acid ((1S)-benzyl-(2R)-hydroxy-3-morpholin-4-yl-3-oxo-propyl)-amide.

5-chloro-1H-indole-2-carboxylic acid [(1S)-benzyl-2-(3-hydroxylmino-pyrrolidin-1-yl)-2-oxo-ethyl]-amide, 5-chloro-1H-indole-2-carboxylic acid [2-(cis-3,4-dihydroxy-pyrrolidin-1-yl)-2-oxo-ethyl]-amide, 5-chloro-1H-indole-2-carboxylic acid [2-((3S,4S)-dihydroxy-pyrrolidin-1-yl)-2-oxo-ethyl]-amide, 5-chloro-1H-indole-2-carboxylic acid [(1S)-benzyl-2-(cis-3,4-dihydroxy-pyrrolidin-1-yl)-2-oxo-ethyl]-amide, 5-chloro-1H-indole-2-carboxylic acid [2-(1,1-dioxo-thiazolidin-3-yl)-2-oxo-ethyl]-amide, 5-chloro-1H-indole-2-carboxylic acid (2-oxo-2-thiazolidin-3-yl-ethyl)-amide, 5-chloro-1H-indole-2-carboxylic acid [(1S)-(4-fluoro-benzyl)-2-(4-hydroxy-piperidin-1-yl)-2-oxo-ethyl]-amide, 5-chloro-1H-indole-2-carboxylic acid [(1S)-benzyl-2-((3RS)-hydroxy-piperidin-1-yl)-2-oxo-ethyl]-amide, 5-chloro-1H-indole-2-carboxylic acid [2-oxo-2-((1RS)-oxo-1-thiazolidin-3-yl)-ethyl]-amide, 5-chloro-1H-indole-2-carboxylic acid [(1S)-(2-fluoro-benzyl)-2-(4-hydroxy-piperidin-1-yl)-2-oxo-ethyl]-amide, 5-chloro-1H-indole-2-carboxylic acid [(1S)-benzyl-2-((3S,4S)-dihydroxy-pyrrolidin-1-yl)-2-oxo-ethyl]-amide, 5-chloro-1H-indole-2-carboxylic acid [(1S)-benzyl-2-(3-hydroxy-azetidin-1-yl)-2-oxo-ethyl]-amide, 5-Chloro-1H-indole-2-carboxylic acid [(1S)-benzyl-2-(3-hydroxylmino-azetidin-1-yl)-2-oxo-ethyl]-amide or 5-chloro-1H-indole-2-carboxylic acid [(1S)-benzyl-2-(4-hydroxylmino-piperidin-1-yl)-2-oxo-ethyl]-amide.

Yet another aspect of this invention is directed to pharmaceutical compositions comprising a compound of Formula I or a pharmaceutically acceptable salt or prodrug thereof and a anti-atherosclerotic agent.

Another aspect of this invention is a method treating atherosclerosis comprising administering to a mammal (e.g., a female or male human)

a. an amount of a first compound, said first compound being a Formula I compound, a prodrug thereof, or a pharmaceutically acceptable salt of said compound or of said prodrug; and b. an amount of a second compound, said second compound being a lipid lowering agent such as atorvastatin wherein the amounts of the first and second compounds result in a therapeutic effect.

This invention is also directed to a pharmaceutical combination composition comprising: a therapeutically effective amount of a composition comprising a first compound, said first compound being a Formula I compound, a prodrug thereof, or a pharmaceutically acceptable salt of said compound or of said prodrug;

a second compound, said second compound being a lipid lowering agent such as atorvastatin; and/or optionally a pharmaceutical carrier, vehicle or diluent.

Another aspect of this invention is a kit comprising:

a. an amount of a Formula I compound, a prodrug thereof, or a pharmaceutically acceptable salt of said compound or of said prodrug and a pharmaceutically acceptable carrier, vehicle or diluent in a first unit dosage form;

b. an amount of a lipid lowering agent such as atorvastatin and a pharmaceutically acceptable carrier, vehicle or diluent in a second unit dosage form; and c. means for containing said first and second dosage forms wherein the amounts of the first and second compounds result in a therapeutic effect.

Yet another aspect of this invention is directed to pharmaceutical compositions comprising a compound of Formula I or a pharmaceutically acceptable salt or prodrug thereof and a cardiovascular agent.

Another aspect of this invention is a method for treating cardiovascular disease comprising administering to a mammal (e.g., a female or male human)

a. an amount of a first compound, said first compound being a Formula I compound, a prodrug thereof, or a pharmaceutically acceptable salt of said compound or of said prodrug; and b. an amount of a second compound, said second compound being a cardiovascular agent wherein the amounts of the first and second compounds result in a therapeutic effect.

This invention is also directed to a pharmaceutical combination composition comprising: a therapeutically effective amount of a composition comprising a first compound, said first compound being a Formula I compound, a prodrug thereof, or a pharmaceutically acceptable salt of said compound or of said prodrug;

a second compound, said second compound being a cardiovascular agent; and/or optionally a pharmaceutical carrier, vehicle or diluent.

Another aspect of this invention is a kit comprising:

a. an amount of a Formula I compound, a prodrug thereof, or a pharmaceutically acceptable salt of said compound or of said prodrug and a pharmaceutically acceptable carrier, vehicle or diluent in a first unit dosage form;

b. an amount of a cardiovascular agent and a pharmaceutically acceptable carrier, vehicle or diluent in a second unit dosage form; and c. means for containing said first and second dosage forms wherein the amounts of the first and second compounds result in a therapeutic effect. In the above combination compositions, combination methods and kits, preferably the cardiovascular agents are for example, β-blockers (e.g., acebutolol, atenolol, bopindolol, labetolol, mepindolol, nadolol, oxprenol, pindolol, propranolol, sotalol), calcium channel blockers (e.g., amlodipine, nifedipine, nisoldipine, nitrendipine, verapamil), potassium channel openers, adenosine, adenosine agonists, ACE inhibitors (e.g., captopril, enalapril), nitrates (e.g., isosorbide dinitrate, isosorbide 5-mononitrate, glyceryl trinitrate), diuretics (e.g., hydrochlorothiazide, indapamide, piretanide, xipamide), glycosides (e.g., digoxin, metildigoxin), thrombolytics (e.g. tPA), platelet inhibitors (e.g., reopro), aspirin, dipyridamol, potassium chloride, clonidine, prazosin or adenosine A3 receptor agonists.

In all of the above combination compositions, combination methods and kits preferred Formula I compounds include the preferred groups of compounds described above labeled as Group A to Group V.

The term "treating", "treat" or "treatment" as used herein includes preventative (e.g., prophylactic) and palliative treatment. By "pharmaceutically acceptable" it is meant the carrier, diluent, excipients, and/or salt must be compatible with the other ingredients of the formulation, and not deleterious to the recipient thereof.

The expression "prodrug" refers to compounds that are drug precursors which following administration, release the drug in vivo via some chemical or physiological process (e.g., a prodrug on being brought to the physiological pH or through enzyme action is converted to the desired drug form).

Exemplary five to six membered aromatic rings optionally having one or two heteroatoms selected independently from oxygen, nitrogen and sulfur are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl and pyrazinyl.

Exemplary partially saturated, fully saturated or fully unsaturated five to eight membered rings optionally having one to three heteroatoms selected independently from oxygen, sulfur and nitrogen are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4-oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, taken independently, optionally having one to four heteroatoms selected independently from nitrogen, sulfur and oxygen are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c) thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

By alkylene is meant saturated hydrocarbon (straight chain or branched) herein a hydrogen atom is removed from each of the terminal carbons. Exemplary f such groups (assuming the designated length encompases the particular example) re methylene, ethylene, propylene, butylene, pentylene, hexylene, heptylene).

By halo is meant chloro, bromo, iodo, or fluoro.

By alkyl is meant straight chain saturated hydrocarbon or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl.

By alkoxy is meant straight chain saturated alkyl or branched saturated alkyl bonded through an oxygen. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

As used herein the term mono-N- or di-N,N-$(C_1-C_x)$alkyl . . . refers to the $(C_1-C_x)$alkyl moiety taken independently when it is di-N,N-$(C_1-C_x)$alkyl. (x refers to integers). In an analagous manner the term mono-N- or di-N,N-$(C_y-C_x)$ cycloalkyl . . . refers to the $(C_y-C_x)$cycloalkyl moiety taken independently when it is di-N,N-$(C_y-C_x)$cycloalkyl . . . (x and y refers to integers).

It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesuffonate. Where more than one basic moiety exists the expression includes multiple salts (e.g., di-salt). The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

As used herein, the expressions "reaction-inert solvent" and "inert solvent" refers to a solvent or mixture of solvents which does not interact with starting materials, reagents, intermediates or products in a manner which adversely affects the yield of the desired product.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates and solvates of the compounds of this invention are also included.

DMF means N,N-dimethylformamide. DMSO means dimethyl sulfoxide. THF means tetrahydrofuran.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$O, $^{14}$O, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$O are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples below, by substituting a readily available isotopically labelled reagent for a non-isotopically labelled reagent.

Other features and advantages will be apparent from the remainder of the specification and claims which describe the invention.

DETAILED DESCRIPTION OF THE INVENTION

In general the compounds of this invention can be made by processes which include processes analogous to those known in the chemical arts, particularly in light of the description contained herein. Certain processes for the manufacture of the compounds of this invention are provided as further features of the invention and are illustrated by the following reaction schemes. These processes may be carried out in sequential or convergent synthetic routes. Other processes may be described in the experimental section. Purification procedures include crystallization and normal phase or reverse phase chromatography.

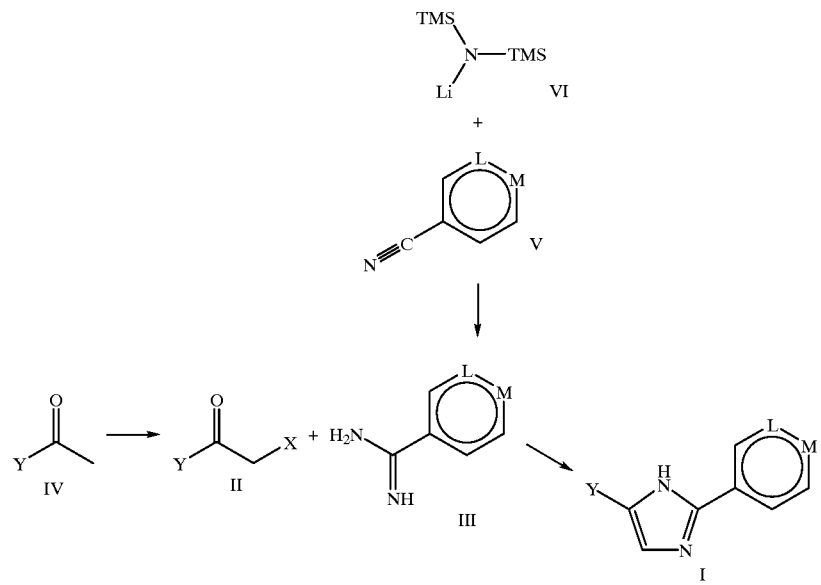

SCHEME I

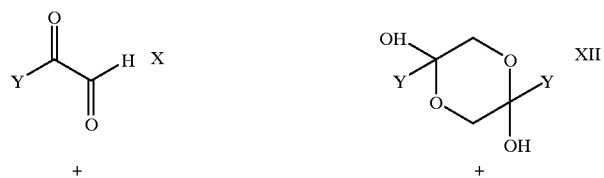

SCHEME II

-continued
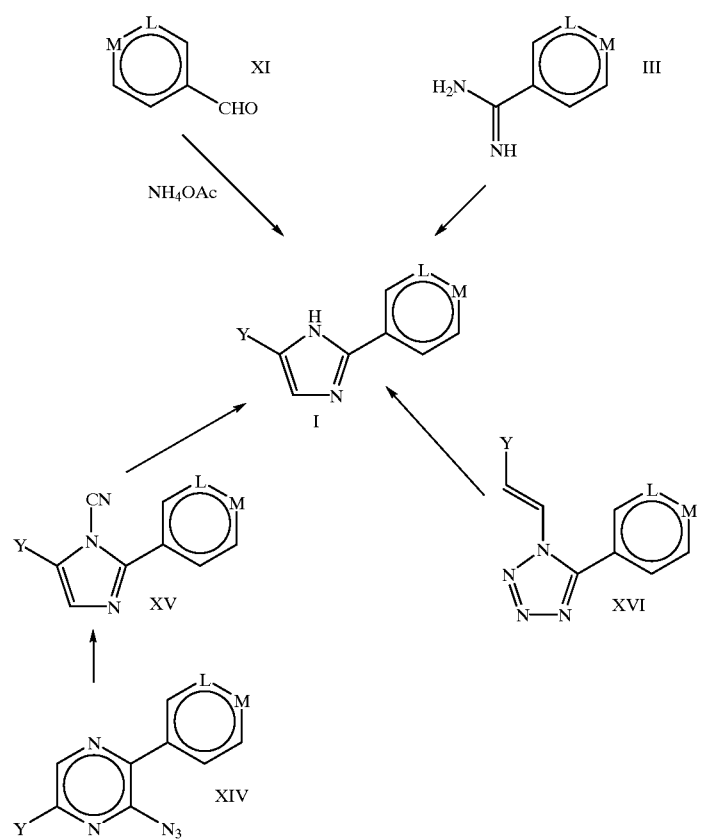
SCHEME III
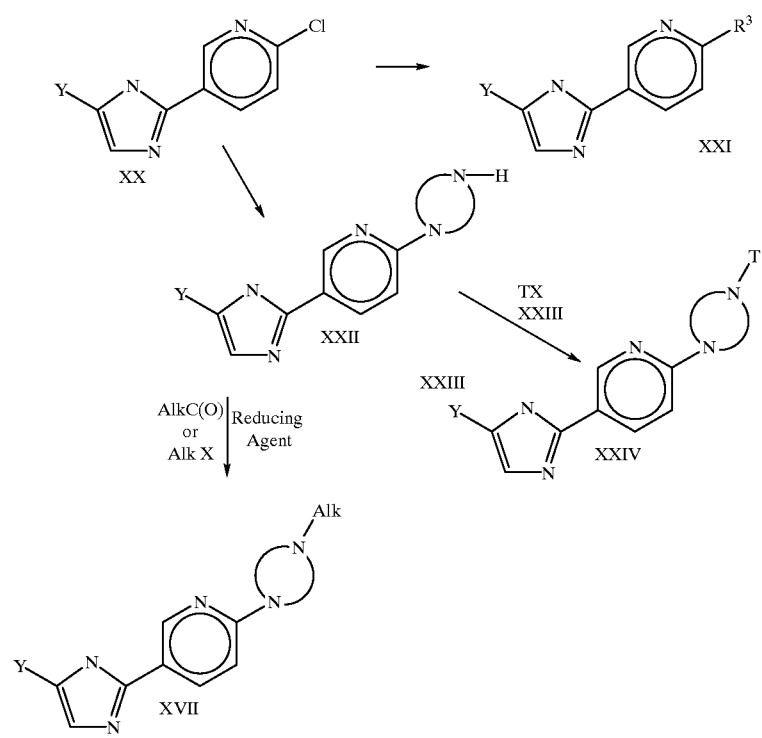

-continued
SCHEME IV
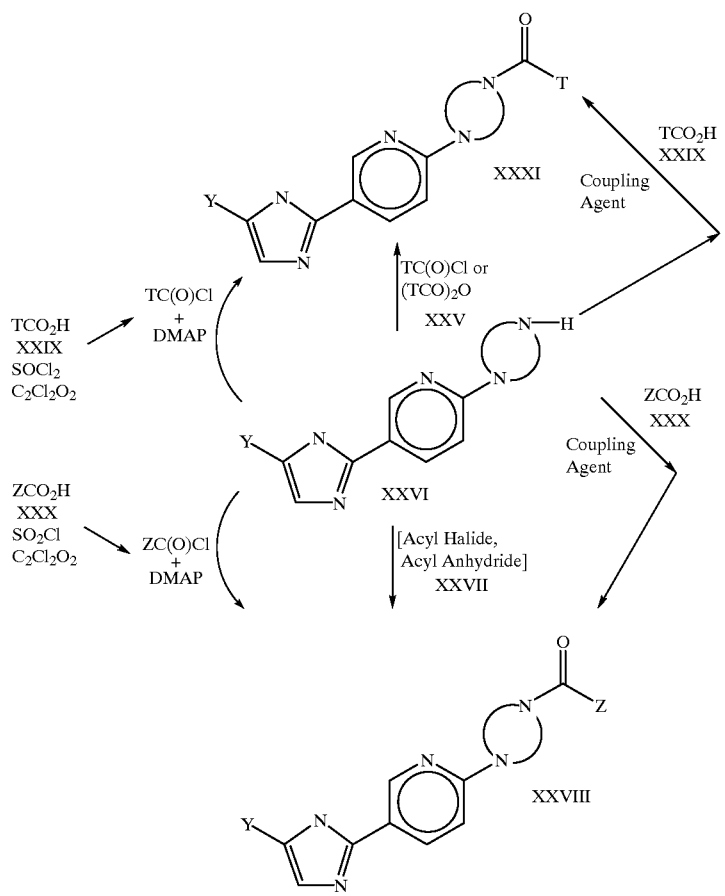
SCHEME V
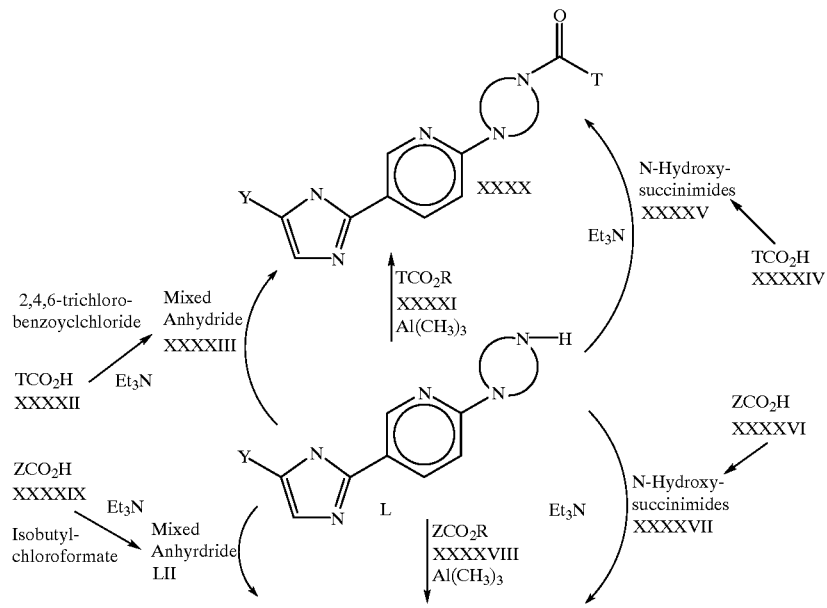

-continued

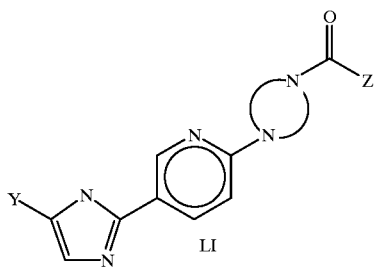

As an initial note, in the preparation of the Formula I compounds it is noted that some of the preparation methods useful for the preparation of the compounds described herein may require protection of remote functionality (e.g., primary amine, secondary amine, carboxyl). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene and P. G. M. Wuts, *Protective Groups in Organic Synthesis*, John Wiley & Sons, New York, 1991.

According to Reaction Scheme I, the Formula I compounds wherein Y, L and M are as described above may be prepared by coupling a Formula III amidine wherein L and M are as described above with the appropriate Formula II haloketone compound wherein Y is as described above and wherein X is $C_1$, Br, or 1.

The Formula III amidine is coupled (see *J. Med. Chem.* 1979, 22, 687) with the Formula II haloketone in an inert solvent such as toluene, THF or chloroform at a temperature of about 20° C. to about 70° C. for about 2 to about 48 hours. Saturated aqueous potassium carbonate may be added to the reaction mixture to facilitate the reaction. In some cases, the uncyclized keto amidine is observed and can be closed, either under thermal conditions such as refluxing in an inert solvent such as toluene or under acidic conditions such as acetic acid in warm chloroform.

The Formula II haloketones wherein Y is as described above and wherein X is Cl, Br, or I are typically available commercially or may be prepared from the corresponding Formula IV methyl ketone wherein Y is as described above by halogenation.

Typically, the Formula IV methyl ketone is treated with a suitable halogenating agent such as molecular bromine in an inert solvent such as dichloromethane or an acidic solvent such as acetic acid at a temperature of about −10° C. to about 23° C. for about 0.5 to about 24 hours.

The Formula III amidines wherein L and M are described above are typically available from commercial sources or may be prepared according to methods known in the literature (e.g., *J. Med. Chem.* 1995, 38, 2251–2255) for example, addition of an "ammonia equivalent" nucleophile to the appropriate Formula V nitrile (wherein L and M are as described above).

Generally, a suitable nucleophile such as lithium hexamethyldisilazide is added to the appropriate Formula V nitrile in an aprotic solvent such as tetrahydrofuran (THF) at a temperature of about −30° C. to about 30° C. for about 1 to about 48 hours.

According to Scheme II the Formula I compounds wherein Y, L and M are as described above may be prepared by combining the Formula X keto aldehyde wherein Y is as described above with the appropriate Formula XI aromatic aldehyde wherein L and M are as described above.

Typically, a Formula X keto aldehyde is combined at a temperature of about 20° C. to about 30° C. for about 12 to about 48 hours with the appropriate Formula XI aldehyde in the presence of ammonium acetate in a polar protic solvent such as methanol (see J. J. Baldwin, et al., *J. Med. Chem.* 1979, 22, 687–694).

Alternatively, Formula I compounds wherein Y, L and M are as described above may be prepared by amidination of a Formula XII hydroxydioxolane wherein Y is as described above with the appropriate Formula III amidine wherein L and M are as described above.

Typically, the Formula XII hydroxydioxolane is reacted with a Formula III amidine in an ammonia containing solvent such as buffered aqueous ammonia at a temperature of about 70° C. to about 100° C. for about 0.5 to about 5 hours (see *J. Med. Chem.* 1995, 38, 2251).

Alternatively, Formula I compounds wherein Y, L and M are as described above may be prepared by rearrangement of an appropriate Formula XV cyanoimidazole wherein Y, L and M are as described above.

Typically, the Formula XV cyanoimidazole is treated with a mineral base such as 10% potassium hydroxide in a water-miscible solvent such as methanol at a temperature of about 20° C. to about 30° C. for about 12 to about 14 hours(see *J. Het. Chem.* 1983, 20, 1277). Alternatively, the cyano group may be removed under suitably acidic conditions such as 20% sulfuric acid at reflux for 5 to 7 hours (see *Heterocyies,* 1985, 23, 1549).

The Formula XV compounds wherein Y, L and M are as described above may be prepared by rearrangement of an appropriate Formula XIV azidopyrazine wherein Y, L and M are as described above.

Typically, thermolysis with resultant rearrangement of the Formula XIV azidopyrazine at an elevated temperature such as about 220° C. to about 240° C. for about 30 seconds to about 60 seconds (no solvent-neat conditions) yields the corresponding Formula XV compound (see *J. Het. Chem.* 1983, 20, 1277 and *Heterocycles,* 1985, 23, 1549). Alternatively, irradiation with resultant rearrangement of the Formula XIV azidopyrazines at a temperature of about 20° C. to 30° C. in an inert and non-absorbing solvent such as ethanol for about 30 minutes to about 6 hours yields the formula XV compound (see *J. Het. Chem.* 1983,20, 1277).

Alternatively, Formula I compounds wherein Y, L and M are as described above may also be prepared from the corresponding Formula XVI tetrazole wherein Y, L and M are as described above via rearrangement.

Typically, the Formula XVI tetrazole is irradiated in an inert and non-absorbing solvent such as light petroleum or ethanol at a temperature of about 20° C. to about 30° C. for about 0.5 to about 6 hours (see *J. Chem. Soc., Perkin Trans. 1* 1984, 1933).

In an alternate route to compounds of Formula I and in accordance with Scheme III the Formula XX chloropyridyl imidazole compound (wherein Y is as described above; such compounds may be prepared as described in Scheme I) is reacted with an appropriate nucleophile such as morpholine, an alkylpiperazine, an arylpiperazine or piperidine under suitable conditions such as a temperature of about 90° C. to about 150° C. for about 2 to about 48 hours in the neat nucleophile or in the presence of a non-nucleophilic solvent such as DMSO or toluene resulting in the corresponding Formula XXI or XXII compounds wherein Y and $R^3$ are as described above (such compounds are Formula I compounds and they may also be intermediates to other Formula I compounds).

Those skilled in the art will recognize that although Scheme III and the following Schemes IV and V depict a particular regioisomer, the same synthetic routes maybe used for the alternative regioisomer (the pyridyl nitrogen in the 4-position)., Formula I compounds (e.g., Formula XXIV compounds) may also be prepared by further functionalization of Formula XXII compounds. For example, Formula XXIV compounds wherein Y and T are as described above may be prepared by arylation of the corresponding Formula XXII compound wherein Y is as described above.

Typically, the Formula XXII compound and appropriate halides (TX), such as a substituted or unsubstituted 2-chloropyridine or a substituted or unsubstituted 2-chloropyrimidine are combined at a temperature of about 80° C. to about 150° C. for about 1 to about 48 hours in a non-nucleophilic solvent such as toluene or DMSO. Alternatively, the Formula XXIV compounds wherein T is aromatic may be prepared by a palladium-catalyzed amination reaction starting from the appropriate aryl bromide, chloride, or iodide (see Wagaw, S.; Buchwald, S. L., *J. Org. Chem.* 1996, 61,7240–7241. Old, D. W.; Wolfe, J. P.; Buchwald, S. L., *J. Am. Chem. Soc.,* 1998, 120, 9722–9723).

Exemplary of further functionalization of Formula XXII compounds are methods where the cyclic amine is alkylated to prepare Formula XVII compounds wherein Y is as described above and Alk is alky), cycloalkyl, cycloalkylalkyl, or heteroalkyl (saturated T ring) optionally substituted as described above.

Generally, the Formula XVII compound is prepared by a reductive amination of the appropriate aldehyde or ketone with a reducing agent such as sodium triacetoxyborohydride in an aprotic solvent such as THF or 1,2-dichloroethane at a temperature of about 20° C. to about 30° C. for about 1 to about 48 hours, optionally in the presence of a carboxylic acid such as acetic acid to promote the reaction. Alternatively, imine formation may be promoted by the initial addition of a Lewis acid such as titanium (IV) chloride in an aprotic solvent such as dichloromethane followed by the addition of a reducing agent such as sodium cyanoborohydride at a temperature of about 20° C. to about 30° C. for about 1 to about 48 hours. Alternatively, Formula XVII compounds may be prepared by the alkylation of Formula XXII compounds with the appropriate alkyating agent such as an alkyl bromide, chloride, iodide, or tosylate in an organic solvent such as dimethylformamide (DMF) in the presence of a mineral base such as potassium carbonate or sodium hydride at a temperature of about 20° C. to about 100° C. for about 1 to about 48 hours.

According to Scheme IV Formula XXXI wherein T is as described above and Formula XXVIII compounds, wherein Z is an alkyl, cycloalkyl, or cycloalkylalkyl optionally sustituted as described above etc., may be prepared by acylation of the appropriate Formula XXVI compound wherein Y is as described above.

Typically, the Formula XXVI compound is combined with the appropriate acylating agent such as a Formula XXVII acyl chloride, bromide, or anhydride or a Formula XXV acid chloride, bromide or anhydride in an aprotic solvent such as dichloromethane in the presence of an organic base such as triethylamine at a temperature of about 0° C. to about 30° C. for about 1 to about 48 hours.

Formula XXXI and XXVIII compounds may also be prepared from the corresponding Formula XXVI cyclic amine by coupling with the appropriate acid, such as the Formula XXX acid wherein Z is an alkyl, cycloalkyl or cycloalkylalkyl moiety optionally substituted as described above or Formula XXIX carboxylic acid wherein T is as described above, in the presence of an appropriate coupling agent. A suitable coupling agent is one which transforms a carboxylic acid into a reactive species which in turn forms an amide linkage on reaction with an amine.

The coupling agent may be a reagent which effects this condensation in a one pot process when mixed together with the carboxylic acid and cyclic amine. Exemplary coupling reagents are 1-(3-dimethylaminopropyl)-3-ethylcarbodiimide hydrochloride-hydroxybenzotriazole (EDC/HBT), dicyclohexylcarbodiimide/hydroxybenzotriazole(DCC/HBT), 2-ethoxy-1-ethoxycarbonyl-1,2-dihydroquinoline (EEDQ), DCC/4-dimethylaminopyridine (DMAP), EDC/DMAP, Benzotriazol-1-yloxytris(dimethylamino)phosphonium hexafluorophosphate (BOPYDMAP and diethylphosphorylcyanide. The coupling is performed in an inert solvent, preferably an aprotic solvent at a temperature of about −20° C. to about 50° C. for about 1 to about 48 hours, in the presence of an organic base such as N-methylmorpholine. Exemplary solvents include acetonitrile, dichloromethane, dimethylformamide and chloroform or mixtures thereof.

Alternatively, the coupling agent may also be that agent which converts the carboxylic acid to an activated intermediate which is isolated and/or formed in a first step and allowed to react with the cyclic amine in a second step. Examples of such coupling agents and activated intermediates are thionyl chloride or oxalyl chloride which form the acid chloride, cyanurc fluoride which forms an acid fluoride or an alkyl chloroformate such as isobutyl or isopropenyl chloroformate or propanephosphonic anhydride (propanephosphonic acid anhydride, PPA) (with a tertiary amine base) which forms a mixed anhydride of the carboxylic acid, or carbonyldiimidazole which forms an acylimidazole. If the coupling agent is oxalyl chloride, it is advantageous to employ a small amount of dimethylformamide as cosolvent with another solvent (such as dichloromethane) to catalyze the formation of the acid chloride. This activated acid derivative may be coupled by mixing with excess cyclic amine in an appropriate solvent together with an appropriate base. Appropriate solvent/base combinations are for example, dichloromethane, dimethylformamide or acetonitrile or mixtures thereof in the presence of excess cyclic amine as base. Other appropriate solvent/base combinations include water or a $((C_1–C_5)$alcohol) or a mixture thereof together with a cosolvent such as dichloromethane, tetrahydrofuran or dioxane and a base such as sodium, potassium or lithium hydroxide in sufficient quantity to consume the acid liberated in the reaction. Use of these coupling agents and appropriate selection of solvents and temperatures are known to those skilled in the art or can be readily determined from the literature. These and other exemplary conditions useful for coupling carboxylic acids are described in Houben-Weyl, Vol XV, part II, E. Wunsch, Ed., G. Theime Verlag, 1974, Stuttgart; M. Bodansky, Principles of Peptide Synthesis, Springer-Verlag, Berlin 1984; and The Peptides, Analysis, Synthesis and Biology (ed. E. Gross and J. Meienhofer), vols 1–5 (Academic Press, NY 1979–1983).

Additionally, according to Scheme V Formula XXXX and Formula LI compounds may be prepared by coupling the appropriate Formula L compound with the appropriate Formula XXXXIII or Formula LII mixed anhydride in an inert solvent such as dichloromethane at a temperature of about −10° C. to about 30° C. for about 0.5 to about 24 hours. The mixed anhydrides may be prepared from a corresponding Formula XXXXII T ring containing carboxylic acid, for example wherein T is as described above, or a Formula XXXXIX acid, wherein Z is an alkyl, cycloalkyl or cycloalkylalkyl acid optionally substituted as described above, using a reagent such as 2,4,6-trichlorobenzoyl chloride or isobutyl chloroformate, as appropriate, and a base such as triethylamine in an inert solvent such as dichloromethane at a temperature of about −10° C. to about 30° C. for about 0.5 to about 24 hours.

Formula XXXXIV T ring containing carboxylic acid, wherein T is as described above, or a Formula XXXXVI acid, wherein Z is an alkyl, cycloalkyl or cycloalkylalky acid optionally substituted as described above can be coupled with N-hydroxysuccinimide using a suitable coupling agent such as DCC or EDC in an inert solvent such as dimethoxyethane at a temperature of about −10° C. to about 25° C. for about 1 to about 48 hours to yield the corresponding Formula XXXXV and Formula XXXXVII N-hydroxysucciminimides. The resulting Formula XXXXV and Formula XXXXVII N-hydroxysucciminimides are reacted with the appropriate Formula L compound in the presence of a base such as triethylamine in an inert solvent such as 1,2-dimethoxyethane at a temperature of about 20° C. to about 30° C. for about 0.5 to about 24 hours to prepare the corresponding Formula LI and Formula XXXX compounds.

In an alternate route to Formula XXXX and Formula LI compounds, Formula XXXXI T ring containing esters such as methyl or ethyl esters and Formula XXXXVIII aliphatic esters such as methyl or ethyl esters can be reacted with a Formula L compound that has been activated by a reagent such as trimethylaluminum in an inert solvent such as toluene at a temperature of about 0° C. to about 40° C. for about 1 to about 48 hours.

Prodrugs of this invention may be made by standard methods. For example, where an alcohol function has been derivatized as an ether may be prepared by combining the alcohol with the appropriate alkyl bromide or iodide in the presence of a base such as potassium carbonate in an inert solvent such as dimethylformamide at a temperature of about 0 to 100° C. for about 1 to about 24 hours. Alkanoylaminomethyl ethers may be obtained by reaction of the alcohol with a bis-(alkanoylamino)methane in the presence of a catalytic amount of acid in an inert solvent such as tetrahydrofuran, according to a method described in U.S. Pat. No. 4,997,984. Alternatively, these compounds may be prepared by the methods described by Hoffman et al. in J. Org. Chem. 1994, 59, 3530.

The starting materials and reagents for the above described compounds are readily available or can be easily synthesized by those skilled in the art using conventional methods of organic synthesis. For example, the aromatic hydrazines used in this invention can be prepared from the corresponding aromatic amines by diazotization followed by reduction conveniently using stannous chloride using procedures known to those skilled in the art. For example, many of the compounds used herein are related to, or are derived from compounds found in nature, in which there is a large scientific interest and commercial need, and accordingly many such compounds are commercially available or are reported in the literature or are easily prepared from other commonly available substances by methods which are reported in the literature.

Some of the compounds of this invention have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of this invention. Also, some of the compounds of this invention are atropisomers (e.g., substituted biaryls) and are considered as part of this invention.

Those skilled in the art will recognize that the compounds of Formula I can exist in several tautomeric forms. All such tautomeric forms are considered as part of this invention. For example, all of the tautomeric forms of the imidazole moiety, as depicted below, of the compounds of Formula I are included in this invention. Also, for example all ketoenol or imine-enamine forms of the compounds of Formula I are included in this invention.

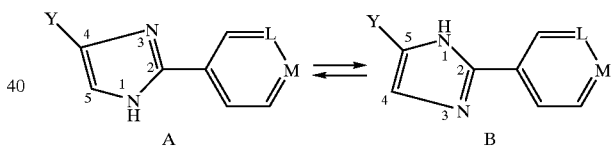

In a related matter, those skilled in the art will recognize that the compound names contained herein are based on a nomenclature convention wherein the tautomer configuration is as depicted in the "A" tautomer above. Thus, the Y substituent is in the four position. An alternative nomenclature convention would be based on the "B" tautomer depicted above and in that convention the Y substituent would be in the five position.

Some of the compounds of this invention are acidic and they form a salt with a pharmaceutically acceptable cation. All of the compounds of this invention are basic and they form a salt with a pharmaceutically acceptable anion. All such salts, including di- and tri-salts are within the scope of this invention and they can be prepared by conventional methods. For example, they can be prepared simply by contacting the acidic and basic entities, in either an aqueous, non-aqueous or partially aqueous medium. The salts are recovered either by filtration, by precipitation with a non-solvent followed by filtration, by evaporation of the solvent, or, in the case of aqueous solutions, by lyophilization, as appropriate.

In addition, when the compounds of this invention form metabolites, hydrates or solvates they are also within the scope of the invention.

Furthermore, it will be understood by those skilled in the art that the compounds, prodrugs and pharmaceutically acceptable salts thereof of the present invention, including pharmaceutical compositions and formulations containing these compounds, prodrugs and salts can be used in a wide variety of combination therapies to treat the conditions and diseases described above. Thus, the compounds, prodrugs and pharmaceutically acceptable salts thereof of the present invention can be used in conjunction with other pharmaceutical agents for the treatment of the disease/conditions described herein. For example, they may be used in combination with pharmaceutical agents that treat obesity, diabetes, hypertension, hyperlipidemia, cardiovascular disease, anxiety, depression, or psychosis. In combination therapy treatment, both the compounds, prodrugs and pharmaceutically acceptable salts thereof of this invention and the other drug therapies are administered to mammals (e.g., humans, male or female, dogs, cats, horses) by conventional methods.

Any β-adrenergic agonist may be used as the second compound in the combination aspect of this invention. -Adrenergic agents have been categorized into $\beta_1$, $\beta_2$, and $\beta_3$ subtypes. Agonists of P-receptors promote the activation of adenyl cyclase. Activation of $\beta_1$ receptors invokes increases in heart rate. Activation of $\beta_2$ receptors induces relaxation of smooth muscle tissue which produces a drop in blood pressure and the onset of skeletal muscle tremors. Activation of $\beta_3$ receptors is known to stimulate lipolysis, which is the breakdown of adipose tissue triglycerides to glycerol and fatty acids. Activation of $\beta_3$ receptors also stimulates the metabolic rate, thereby increasing energy expenditure. Accordingly, activation of $\beta_3$ receptors promotes the loss of fat mass. Compounds that stimulate β receptors are therefore useful as anti-obesity agents. Compounds which are $\beta_3$-receptor agonists have hypoglycemic and/or anti-diabetic activity. Such activity is readily determined by those skilled in the art according to standard assays (International Patent Application, Publication No. WO 96135671). Several compounds are described and referenced below; however, other β-adrenergic agonists will be known to those skilled in the art. International Patent Application, Publication No. WO 96135671 (the disclosure of which is incorporated herein by reference) discloses compounds, such as substituted tee aminopyridines, which are adrenergic agonists. International Patent Application, Publication No. WO 93(16189 (the disclosure of which is incorporated herein by reference) discloses the use of selective $\beta_3$ receptor agonists in combination with compounds which modify eating behavior for the treatment of obestiy.

Any thyromimetic antiobesity agent may be used as the second compound in the combination aspect of this invention. These compounds are tissue selective thyroid hormone agonists. These compounds are able to induce weight loss by mechanisms other than appetite suppression, e.g., through stimulation of the metabolic rate in peripheral tissue, which, in turn, produces weight loss. Such metabolic effects are readily measured by those skilled in the art according to standard assays (for example, by indirect calorimetry). A variety of these compounds are described and referenced below, however other thyromimetic antiobesity agents will be known to those skilled in the art It is well known to one of ordinary skill in the art that selectivity of thermogenic effect is an important requirement for a useful therapeutic agent in the treatment of, for example, obesity and related conditions. U.S. Pat. Nos. 5,401,772; 5,567,674; and 5,654, 468, the disclosures of which are incorporated herein by reference, describe a series of heteroacetic acid derivatives.

Any eating behavior modifying compound may be used as the second compound of this invention. Compounds which modify eating behavior include anorectic agents, which are compounds which diminish the appetite. Such classes of anorectic agents are well known to one of ordinary skill in the art. A variety of these compounds are described and referenced above; however, other anorectic agents will be known to those skilled in the art and are described below. A particularly preferred monoamine reuptake inhibitor is sibutramine, which can be prepared as disclosed in U.S. Pat. No. 4,929,629, the disclosure of which is incorporated herein by reference. Preferred serotoninergic agents include fenfluramine and dexfenfluramine, which can be prepared as disclosed in U.S. Pat. No. 3,198,834, the disclosure of which is incorporated herein by reference. A particularly preferred dopamine agonist is bromocriptine, which can be prepared as disclosed in U.S. Pat. Nos. 3,752,814 and 3,752,888, the disclosures of which are incorporated herein by reference. Another preferred anorectic agent is phentermine, which can be prepared as disclosed in U.S. Pat. No. 2,408,345, the disclosure of which is incorporated herein by reference.

Any other NPY receptor antagonists may be used as the second component in the combination aspect of this invention. The term NPY receptor antagonist refers to compounds which interact with NPY receptors and inhibit the activity of neuropeptide Y at those receptors and thus are useful in treating disorders associated with neuropeptide Y, such as feeding disorders, including obesity. Such inhibition is readily determined by those skilled in the art according to standard assays. In addition, the compounds described and referenced below are NPY receptor antagonists; however, other NPY receptor antagonists will also be known to those skilled in the art. WO 99/07703 (the disclosure of which is hereby incorporated by reference) discloses certain 4-aminopyrrole (3,2-d) pyrimidines as neuropeptide Y receptor antagonists. Other such compounds are disclosed in the following WO publications the disclosures of which are hereby incorporated by reference: WO 96(14307; WO 96/40660; WO 98(03492; WO 98(03494; WO 98/03493; WO 96(14307; and WO 96(40660.

For the treatment of Alzheimer's disease, any cholinomimetic drug, such as Donepizil, may be used as the second compound in the combination aspect of this invention.

For the treatment of anxiety, any antianxiolytic drug, such as a benzodiazepine, valium, or librium, may be used as the second compound in the combination aspect of this invention.

For the treatment of depression, any tricyclic antidepressant such as, desipramine, or any selective serotonin reuptake inhibitor (SSRI's), such as ZOLOFT® and PROZAC®, may be used as the second compound in the combination aspect of this invention.

For the treatment of psychosis, any typical or atypical antipsychotic drug, such as haloperidol or clozapine may be used as the second compound in the combination aspect of this invention.

For the treatment of for example, diabetes related diseases/conditions any aldose reductase inhibitor may be used as the second compound in the combination aspect of this invention. The term aldose reductase inhibitor refers to a compound which inhibits the bioconversion of glucose to sorbitol catalyzed by the enzyme aldose reductase. Such inhibition is readily determined by those skilled in the art according to standard assays (J. Malone, Diabetes, 29:861–864, 1980, "Red Cell Sorbitol, an Indicator of Diabetic Control"). A variety of aldose reductase inhibitors are described and referenced below; however other aldose reductase inhibitors will be known to those skilled in the art. Examples of aldose reductase inhibitors useful in the compositions and methods of this invention include, for example, zopolrestat.

For the treatment of for example, diabetes related diseases/conditions any glycogen phosphorylase inhibitor may be used as the second compound in the combination aspect of this invention. The term glycogen phosphorylase inhibitor refers to any substance or agent or any combination of substances and/or agents which reduces, retards or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis). Such actions are readily determined by those skilled in the art according to standard assays described in the following publications which describe a variety of these compounds: WO 96139384, published Dec. 12, 1996; and WO 96/39385, published Dec. 12, 1996; the disclosures of these applications are hereby incorporated by reference herein. Other preferred glycogen phosphorylase inhibitors are described above.

For the treatment of for example, diabetes related diseases/conditions any sorbitol dehydrogenase inhibitor may be used as the second compound in the combination aspect of this invention. The term sorbitol dehydrogenase inhibitor refers to a compound which inhibits the enzyme sorbitol dehydrogenase, which catalyzes the oxidation of sorbitol to fructose. Such inhibition is readily determined by those skilled in the art according to standard assays (as described in U.S. Pat. No. 5,728,704 and references cited therein). A variety of these compounds are described and referenced below; however other sorbitol dehydrogenase inhibitors will be known to those skilled in the art. U.S. Pat. No. 5,728,704 (the disclosure of which is hereby incorporated by reference) discloses substituted pyrimidines to inhibit sorbitol dehydrogenase, lower fructose levels, and/or treat or prevent diabetic complications, such as diabetic neuropathy, diabetic retinopathy, diabetic nephropathy, diabetic microangiopathy and diabetic macroangiopathy.

Any other known or commercially marketed anti-diabetic compound may be used as the second compound in the combination aspect of this invention. A variety of such compounds are described above in the Summary section; however other such compounds will be known to those skilled in the art.

Neuropeptide Y (NPY) and related peptides (such as pancreatic polypeptide and peptide YY) are broadly distributed in central and peripheral neurons and have a broad array of biological activity mediated through the NPY receptors that exist in a variety of tissues. NPY (and related peptides) affect the cardiovascular system, vasculature, hormonal secretions, and central nervous system, renal, gastrointestinal and pulmonary systems and metabolism. NPY potently stimulates hyperphagia and induces insulin resistance. Thus NPY antagonists are useful in the treatment of the disease/conditions described above.

As a consequence of their action in reducing body fat (lipolysis) the compounds of the present invention possess utility for increasing lean meat deposition and/or improving the lean meat to fat ratio in edible animals including poultry and ungulate animals such as swine, cattle, sheep, and goats.

Compounds of formula I can additionally be used for the treatment of obese household pets, for example companion animals such as dogs and cats.

The utility of the compounds of the present invention as medical agents in the treatment of diseases, such as are detailed herein in mammals (e.g. humans) for example, obesity in patients or to induce weight loss or for anorectic activity is demonstrated by the activity of the compounds of this invention in conventional preclinical assays described below. Such assays also provide a means whereby the activities of the compounds of this invention can be compared with the activities of other known compounds. The results of these comparisons are useful for determining dosage levels in mammals, including humans, for the treatment of such diseases.

Assay for NPY-5 Binding $[^{125}I]$ peptide YY (PYY) Binding at Human NPY Receptors Expressed in Sf9 Cells Baculovirus-infected Sf9 cells (American Tissue Culture Collection, ACTT, Rockville, Md.) expressing recombinant human NPY 5 receptors are harvested at 48 hours. h NPY-Y5 receptor cDNA is cloned using standard cloning techniques. (Ref: *Molecular Cloning A Laboratory Manual*, 2nd Edition, J. Sambrook, E. F. Fritsch, T. Maniatis; Cold Spring Habor Laboratory Press; Cold Spring Habor, N.Y., 1989) and cells were transfected using calcium phosphate. At the time of harvest, cells pellets are resuspended in lysis buffer (20 mM Tris-HCl, pH 7.4, 5 mM EDTA, 0.5 ug/ml leupeptin, 2 ug/ml Aprotonin and 200 mM PMSF) and homogenized using a Polytron (setting 3, 25–30 seconds). Homogenates are centrifuged at 4° C. for 5 minutes at 200×g (–1.5 rpm) to pellet the nuclei. The supernatant is collected into a fresh tube and centifuged at 48,000×g for 10 minutes. Pellets are washed once in lysis buffer and centrifuged. The final pellet is resuspended in phosphate buffered saline (PBS) and stored in aliquots at –80° C. Purified membranes are washed using PBS and resuspended in binding buffer (50 mM Tris(HCl), pH 7.4, 5 mM KCl, 120 mM NaCl 2 mM $CaCl_2$, 1 mM $MgCl_2$ 0.1% bovine seurm albumin (BSA)). Membranes (20 ug/reaction tube) are added to polypropylene tubes containing 0.035 nM $[^{125}I]PYY$(porcine) (Dupont New Research Products, Boston MA), compounds ranging from $10^{-12}$ M to $10^{-5}$ M, and buffer to yield a final volume of 0.5 mL. Nonspecific binding is determined in the presence of 1 uM NPY(human) (Sigma; St. Louis, MO) and accounts for 10% of total binding. Following a 2 hour incubation at room temperature, the reaction is terminated by rapid vacuum filtration. Samples are filtered over presoaked GF/C Whatman filters (1.0% polyethylenemine) and rinsed 2 times with 5 mL cold binding buffer without BSA. A gamma counter is used to count filters with an efficiency of 85%. $IC_{50}$ values are calculated with the non-linear curve fitting program RS/1 (SigmaPlot, Jandel).

Y5 Ca mobilization assay

A stable *Bowes melanoma* cell line is generated expressing functional Y5 receptors useful for the secondary screening of Y5 antagonists using a calcium fluorescence assay. The coding sequence for human Y5 receptor h NPY-Y5 receptor cDNA is cloned using standard cloning techniques (Ref: *Molecular Cloning A Laboratory Manual*, 2nd Edition, J. Sambrook, E. F. Fritsch, T. Maniatis; Cold Spring Habor Laboratory Press; Cold Spring Habor, N.Y., 1989) and is subcloned into a novel mammalian expression vector called phe (Ref: B. S. Sachais et al., *J. Biol. Chem.*, 1998, 266:231 92322). This expression vector has a Harvey murine sarcoma virus long terminal repeat to drive expression of the Y5 structural gene. This plasmid construct is used along with calcium phosphates to stably transfect human Bowes melanoma cells (HMCB; obtained from ATCC, Rockville, Md.), a cell line in which several Gαi-linked receptors are expressed at reasonable levels and are coupled to functional responses. Cells are maintained at 37° C. and 5% $CO_2$ in Eagle's minimum essential medium with 0.1 mM non-essential amino acids, 1.0 mM sodium pyruvate and 25 mM HEPES which is supplemented with 10% fetal bovine serum (pH 7.3). This cell host exhibits low levels of Y1 responses and sites, and no other NPY-induced responses. The Y1 antagonist BIBP3226 (Research Biochemicals International, Natick, Mass.) at 10 uM completely blocks the endogenous NPY response. A single clonal cell line is isolated and characterized with the agonist peptide NPY. In the presence of 10 uM BIBP3226, NPY stimulated calcium mobilization with an $EC_{50}$ from 9 nM to 54 nM in ten independent studies.

Cells are plated onto 96 well plates at 30,000 cells I well for twenty-four hours. The cells are rinsed with buffered saline (consisting of: 115 mM NaCl, 0.96 mM $NaH_2PO_4$, 1 mM $MgSO_4$, 25 mM HEPES, 2 mM $CaCl_2$, 5 mM KCl, 5 mM Glucose, 1 mM Probenecid) and incubated for 1.5 hrs. in the fluorescent $Ca^{2+}$ indicator Fluo-3 AM (10 $\mu$M, Teflabs, Austin, Tex.) made in the same buffered saline. Cells are rinsed twice with buffer supplemented with 1 mM carbachol and 10 ,M BIBP3226. NPY applied to HMCB Y5 cells produce a concentration dependent increase in intracellular calcium as determined by an increase in fluorescence read on a Fluorometric Imaging Plate Reader (FLIPR, Molecular Devices, Sunnyvale, Calif.). The concentration of NPY used in these experiments is between the $EC_{30}$ and $EC_{50}$ as determined just prior to each experiment. Fluorescence increase in response to NPY in the presence of test compounds was compared to control responses in the same plate and the $IC_{50}$ for each compound is determined by a fit of the data to the logistic equation (Kaleidograph software, Reading Pa.).

PYY 3–36 Induced GTPγ$^{35}$S Binding at Human NPY Y5 Receptors Co-Expressed With GaO. GαO, Gβ1, and Gβ2 in Sf9 Cells Agonist induced GTPγ$^{35}$S binding by G-protein coupled receptors (GPCR) provides a functional measure of G-protein activation. This assay has been widely used for many GPCR's and offers the possibility to distinguish agonists from antagonists and to determine potency and efficacy of agonists for a given GPCR (Thomas et al., 1995; OBoyle and Lawler, 1995). GTPγ$^{35}$S binding activity is measured using a modification of a previously described method (Wieland and Jacobs, 1994). Log-phase Sf9 cells (ATCC, Rockville, Md.) are co-infected with separate baculoviral stocks encoding the hNPY Y5 (cloned using standard cloning techniques (Ref: *Molecular Cloning A Laboratory Manual,* 2nd Edition, J. Sambrook, E. F. Fritsch, T. Maniatis; Cold Spring Habor Laboratory Press; Cold Spring Habor, N.Y., 1989) receptor and the G-protein subunits αo, β1, and γ2 (purchased from BioSignal Montreal, Canada) followed by culturing in Hink's TNM-FH insect medium supplemented Grace's with 4.1 mM L-Gln, 3.3a/L LAH, 3.3 g/L ultrafiltered yeastolate and 10% heat-inactivated fetal bovine serum at 27° C. 72 hours post infection, a sample of cell suspension is analyzed for viability by trypan blue dye exclusion, and the remaining Sf9 cells are harvested via centrifugation (300 rpm/10 min/4° C.). Each pellet is resuspended in homogenization buffer (10 mM HEPES, 250 mM sucrose, 0.5 $\mu$g/ml leupeptin, 2 $\mu$g/ml Aprotonin, 200 $\mu$M PMSF and 2.5 mM EDTA, pH 7.4) and homogenized using a Polytron (setting 5 for 30 seconds). The homogenate is centrifuged at 40° C. for 10 minutes at 536×g to pellet the nuclei. The supernatant is collected into a fresh tube and centrifuged twice in the same buffer at 48,000×g for 40 minutes. The final pellet for each membrane preparation is resuspended in DPBS containing 5 mM EDTA and stored in aliquots at −80° C. On the day of the assay, thawed membrane homogenates are resuspended in assay buffer (50 mM Tris pH 7.0, 120 mM NaCl, 2 mM $MgCl_2$, 2 mM EGTA, 0.1% BSA, 0.1 mM bacitracin, 100KIU/mL Aprotinin, 5 $\mu$M GDP) and added to reaction tubes at a concentration of 30 mg/reaction tube. After adding test compounds at concentrations ranging from $10^{-11}$M to $10^{-5}$M, reactions are initiated by the addition of both 100 pM GTPγ$^{35}$S and PYY 3-36 ranging in concentration from 0.001 nM to 1.0 $\mu$M (final volume of 0.250 ml). Following a 30 minute incubation at RT, the reaction is terminated by vacuum filtration over GF/C filters (Pre-soaked in wash buffer, 0.1% BSA) with ice-cold wash buffer (50 mM Tris pH 7.0, 120 mM NaCl). Bound GTPγ$^{35}$S is determined by liquid scintillation spectrometry. Non-specific binding is defined by 10 mM GTPγS. To estimate the $EC_{50}$, $IC_{50}$ and $K_i$, the results of GTP±$^{35}$S binding experiments are analyzed using SigmaPlot software (Jandel).

In Vivo Methods

SINGLE DOSE EFFECTS ON FOOD AND WATER INTAKE AND BODY WEIGHT GAIN IN FASTED RATS

Subjects.

Male Sprague-Dawley rats (Sasco, St. Louis, Mo.) weighing 210–300 g at the beginning of the experiment are used. Animals are triple-housed in stainless steel hanging cages in a temperature (22° C.±20) and humidity (40–70% RH) controlled animal facility with a 12:12 hour light-dark cycle. Food (Standard Rat Chow, PMI Feeds Inc., #5012) and water are available ad libitum.

Apparatus.

Consumption data is collected while the animals are housed in Nalgene Metabolic cages (Model #650-0100). Each cage is comprised of subassemblies made of clear polymethlypentene (PMP), polycarbonate (PC), or stainless steel (SS). All parts disassemble for quick and accurate data collection and for cleaning. The entire cylinder-shaped plastic and SS cage rests on a SS stand and houses one animal.

The animal is contained in the round Upper Chamber (PC) assembly (12 cm high and 20 cm in diameter) and rests on a SS floor. Two subassemblies are attached to the Upper Chamber. The first assembly consists of a SS feeding chamber (10 cm long, 5 cm high and 5 cm wide) with a PC feeding drawer attached to the bottom. The feeding drawer has two compartments: a food storage compartment with the capacity for approximately 50 g of pulverized rat chow, and a food spillage compartment. The animal is allowed access to the pulverized chow by an opening in the SS floor of the feeding chamber. The floor of the feeding chamber does not allow access to the food dropped into the spillage compartment.

The second assemby includes a water bottle support, a PC water bottle (100 ml capacity) and a graduated water spillage collection tube. The water bottle support funnels any spilled water into the water spillage collection tube.

The lower chamber consists of a PMP separating cone, PMP collection funnel, PMP fluid (urine) collection tube, and a PMP solid (feces) collection tube. The separating cone is attached to the top of the collection funnel, which in turn is attached to the bottom of the Upper Chamber. The urine runs off the separating cone onto the walls of the collection funnel and into the urine collection tube. The separating cone also separates the feces and funnels it into the feces collection tube.

Food consumption, water consumption, and body weight are measured with an Ohaus Portable Advanced scale (±0.1 g accuracy).

Procedure.

Prior to the day of testing, animals are habituated to the testing apparatus by placing each animal in a Metabolic cage for 1 hour. On the day of the experiment, animals that are food deprived the previous night are weighed and assigned to treatment groups. Assignments are made using a quasi-random method utilizing the body weights to assure that the treatment groups have similar average body weight. Animals are then administered either vehicle (generally 0.5% methyl cellulose, MC) or test compound. At that time, the feeding drawer filled with pulverized chow, the filled water bottle, and the empty urine and feces collection tubes are weighed. Two hours after test compound treatment, each animal is weighed and placed in a Metabolic Cage. Following a one hour test session, animals are removed and body weight obtained. The food and water containers are then weighed and the data recorded.

Test Compound.

Test Compound (suspended in 0.5% MC) or 0.5% MC is administered orally (0.1–50 mg/kg for oral (PO) dosing) using a gavage tube connected to a 3 or 5 ml syringe at a volume of 10 ml/kg. In some instances test compound is administered by a systemic route (e.g. by intravenous injection 0.1–20 mg/kg for i.v. dosing). Test compound for oral dosing is made into a homogenous suspension by stirring and ultrasonicating for at least 1 hour prior to dosing.

Statistical Analyses.

The means and standard errors of the mean (SEM) for food consumption, water consumption, and body weight change are calculated. One-way analysis of variance using Sytat (5.2.1) is used to test for group differences. A significant effect is defined as having a p value of <0.05.

The following parameters are defined: Body weight change is the difference between the body weight of the animal immediately prior to placement in the metabolic cage and its body weight at the end of the one hour test session. Food consumption is the difference in the weight of the food drawer prior to testing and the weight following the 1 hour test session. Water consumption is the difference in the weight of the water bottle prior to testing and the weight following the 1 hour test session.

OVERNIGHT FOOD INTAKE

Subjects.

Male Sprague-Dawley rats (Sasco, St. Louis, Mo.) weighing 210–300 g at the beginning of the experiment are used. Animals are pair or triple-housed in stainless steel hanging cages in a temperature (22° C.±20) and humidity (40–70% RH) controlled animal facility with a 12:12 hour light-dark cycle. Food (Standard Rat Chow, PMI Feeds Inc., #5012) and water are available ad libitum.

Apparatus.

Consumption and elimination data are obtained while the animals are housed in Nalgene Metabolic cages (Model #650-0100). Each cage is comprised of subassemblies made of clear polymethlypentene (PMP), polycarbonate (PC), or stainless steel (SS). All parts disassemble for quick and accurate data collection and for cleaning. The entire cylinder-shaped plastic and SS cage rests on a SS stand and houses one animal.

The animal is contained in the round Upper Chamber (PC) assembly (12 cm high and 20 cm in diameter) and rests on a SS floor. Two subassemblies are attached to the Upper Chamber. The first assembly consists of a SS feeding chamber (10 cm long, 5 cm high and 5 cm wide) with a PC feeding drawer attached to the bottom. The feeding drawer has two compartments: a food storage compartment with the capacity for approximately 50 g of pulverized rat chow, and a food spillage compartment. The animal is allowed access to the pulverized chow by an opening in the SS floor of the feeding chamber. The floor of the feeding chamber does not allow access to the food dropped into the spillage compartment. The second assemby includes a water bottle support, a PC water bottle (100 ml capacity) and a graduated water spillage collection tube. The water bottle support funnels any spilled water into the water spillage colllecton tube.

The lower chamber consists of a PMP separating cone, PMP collection funnel, PMP fluid (urine) collection tube, and a PMP solid (feces) collection tube. The separating cone is attached to the top of the collection funnel, which in turn is attached to the bottom of the Upper Chamber. The urine runs off the separating cone onto the walls of the collection funnel and into the urine collection tube. The separating cone also separates the feces and funnels it into the feces collection tube.

Food consumption, water consumption, urine excretion, feces excretion, and body weight are measured with an Ohaus Portable Advanced scale (±0.1 g accuracy).

Procedure.

On the day of the experiment, animals are weighed and assigned to treatment groups. Assignments are made using a quasi-random method utilizing the body weights to assure that the treatment groups have similar average body weight. Two hours prior to lights off (1830 hours), animals are administered either vehicle (0.5% methyl cellulose, MC) or test compound. At that time, the feeding drawer filled with pulverized chow, the filled water bottle, and the empty urine and feces collection tubes are weighed. Following dosing, each animal is weighed and placed in the Metabolic Cage. Animals are removed from the Metabolic Chamber the following morning (0800 hours) and body weight obtained. The food and water containers, and the feces and urine collection tubes, are weighed and the data recorded.

Test Compound.

Test compound (suspended in 0.5% MC) or 0.5% MC is administered orally (PO) using a gavage tube connected to a 3 or 5 ml syringe at a volume of 10 mVkg. Test compound is made into a homogenous suspension by stirring and ultrasonicating for at least 1 hour prior to dosing. In some experiments, animals are tested for more than 1 night. In these studies, animals are administered, on subsequent nights, the same treatment (test compound or 0.5% MC) they had received the first night.

Statistical Analyses.

The means and standard errors of the mean (SEM) for food consumption, water consumption, urine excretion, feces excretion, and body weight change were calculated. One-way analysis of variance using Sytat (5.2.1) is used to test for group differences. A significant effect is defined as having a p value of <.05.

The following parameters are defined: Body weight change is the difference between the body weight of the animal immediately prior to placement in the metabolic cage (1630 hours) and its body weight the following morning (0800 hours). Food consumption is the difference in the weight of the food drawer at 1630 and the weight at 0800. Water consumption is the difference in the weight of the water bottle at 1630 and the weight at 0800. Fecal excretion is the difference in the weight of the empty fecal collection tube at 1630 and the weight at 0800. Urinary excretion is the difference in the weight of the empty urine collection tube at 1630 and the weight at 0800.

Administration of the compounds of this invention can be via any method which delivers a compound of this invention preferentially to the desired tissue (e.g., brain, renal or intestinal tissues). These methods include oral routes, parenteral, intraduodenal routes, etc. Generally, the compounds of the present invention are administered in single (e.g., once daily) or multiple doses or via constant infusion.

Generally, the compounds of this invention are administered orally, or parenterally (e.g., intravenous, intramuscular, subcutaneous or intramedullary). Topical administration may also be indicated, for example, where the patient is suffering from swallowing disorders or whenever the medication is best applied to the surface of a tissue or organ as determined by the attending physician.

The amount and timing of compounds administered will, of course, be dependent on the subject being treated, on the severity of the affliction, on the manner of administration and on the judgement of the prescribing physician. Thus, because of patient to patient variability, the dosages given below are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases (e.g., cardiovascular disease).

Thus, for example, in one mode of administration the compounds of this invention may be administered orally. The compounds of this invention may also be administered in a chronic daily mode.

An amount of the compounds of this invention is used that is effective for the indications described above for example, the amount useful as an anti-obesity agent. A preferred dosage is about 0.001 to 100 mg/kg/day of the compound of this invention. An especially preferred dosage is about 0.01 to 50 mg/kg/day of the compound of this invention.

The second compound of the combination aspect of this invention, when administered to an animal, is dosed at a range between about 0.01 to about 100 mg/kg/day body weight, preferably about 0.1 mg/kg/day to about 10 mg/kg/day body weight, administered singly or as a divided dose. Particularly, when the second compound of this invention is (1) sibutramine, the dosage of sibutramine is about 0.01 mg/kg/day to about 30 mg/kg/day body weight, preferably about 0.1 mg/kg/day to about 1 mg/kg/day body weight; (2) dexfenfluramine, the dosage of dexfenfluramine is about 0.01 mg/kg/day to about 30 mg/kg/day body weight, preferably about 0.1 mg/kg/day to about 1 mg/kg/day body weight; (3) bromocriptine, the dosage of bromocriptine is about 0.01 to about 10 mg/kg/day body weight, preferably 0.1 mg/kg/day to about 10 mg/kg/day body weight; (4) phentermine, the dosage of phentermine is about 0.01 mg/kg/day to about 10 mg/kg/day, preferably about 0.1 mg/kg/day to about 1 mg/kg/day body.

An amount of the aldose reductase inhibitor of this invention that is effective for the activities of this invention may be used. Typically, an effective dosage for the aldose reductase inhibitors of this invention is in the range of about 0.1 mg/kg/day to 100 mg/kg/day in single or divided doses, preferably 0.1 mg/kg/day to 20 mg/kg/day in single or divided doses.

The compounds of the present invention are generally administered in the form of a pharmaceutical composition comprising at least one of the compounds of this invention together with a pharmaceutically acceptable carrier, vehicle or diluent. Thus, the compounds of this invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions, for example, in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Other administration methods include iontophoretic patches, implants and inhalation.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 15th Edition (1975).

Pharmaceutical compositions according to the invention may contain for example 0.0001%–95% of the compound(s) of this invention. In any event, the composition or formulation to be administered will contain a quantity of a compound(s) according to the invention in an amount effective to treat the disease/condition of the subject being treated.

The two different compounds of this combination of this invention can be co-administered simultaneously or sequentially in any order, or as a single pharmaceutical composition comprising a compound of Formula I, prodrug or salt thereof and the second compound as described above (e.g., 3 agonist). Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I, a prodrug thereof or a salt of such compound or prodrug and a second compound as described above. The kit comprises means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The following paragraphs describe exemplary formulations, dosages etc. useful for non-human animals. The administration of a compound of formula I can be effected orally or non-orally, for example by injection. An amount of a compound of formula I is administered such that an effective dose is received, generally a daily dose which, when administered orally to an animal is usually between 0.01 and 100 mg/kg of body weight, preferably between 0.1 and 50 mg/kg of body weight. Conveniently, the medication can be carried in the drinking water so that a therapeutic dosage of the agent is ingested with the daily water supply. The agent can be directly metered into drinking water, preferably in the form of a liquid, water-soluble concentrate (such as an aqueous solution of a water soluble salt). Conveniently, the active ingredient can also be added directly to the feed, as such, or in the form of an animal feed supplement, also referred to as a premix or concentrate. A premix or concentrate of therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound according to the invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

Drinking water and feed effective for increasing lean meat deposition and for improving lean meat to fat ratio are generally prepared by mixing a compound of the invention with a sufficient amount of animal feed to provide from about $10^{-3}$ to 500 ppm of the compound in the feed or water.

The preferred medicated swine, cattle, sheep and goat feed generally contain from 1 to 400 grams of active ingredient per ton of feed, the optimum amount for these animals usually being about 50 to 300 grams per ton of feed.

The preferred poultry and domestic pet feeds usually contain about 1 to 400 grams and preferably 10 to 400 grams of active ingredient per ton of feed.

For parenteral administration in animals, the compounds of the present invention may be prepared in the form of a paste or a pellet and administered as an implant, usually under the skin of the head or ear of the animal in which increase in lean meat deposition and improvement in lean mean to fat ratio is sought.

In general, parenteral administration involves injection of a sufficient amount of the compounds of the present invention to provide the animal with 0.01 to 100 mg/kg/day of body weight of the active ingredient. The preferred dosage for poultry, swine, cattle, sheep, goats and domestic pets is in the range of from 0.1 to 50 mg/kg/day.

Paste formulations can be prepared by dispersing the active compound in a pharmaceutically acceptable oil such as peanut oil, sesame oil, corn oil or the like.

Pellets containing an effective amount of a compound of the present invention can be prepared by admixing a compound of the present invention with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body.

The present invention has several advantagous veterinary features. For the pet owner or veterinarian who wishes to increase leanness and trim unwanted fat from pet animals, the present invention provides the means by which this can be accomplished. For poultry and swine raisers, using the method of the present invention yields leaner animals which command higher prices from the meat industry.

The compounds of this invention generally will be administered in a convenient formulation. The following formulation examples are illustrative only and are not intended to limit the scope of the present invention.

In the formulations which follow, "active ingredient" means a compound(s) of this invention.

Formulation 1: Gelatin Capsules

Hard gelatin capsules are prepared using the following:

| Ingredient | Quantity (mg/capsule) |
|---|---|
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
|---|---|
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25100 mg of active ingredients are made up as follows:

Formulation 3: Tablets

| Ingredient | Ouantity (mg/tablet) |
|---|---|
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |

-continued

| Ingredient | Ouantity (mg/tablet) |
|---|---|
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
|---|---|
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 74.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container. Suppositories are prepared as follows:

Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:
Formulation 7: Intravenous Solution

| Ingredient | Quantity |
| --- | --- |
| Active ingredient | 25 mg–10,000 mg |
| Isotonic saline | 1,000 mL |

The solution of the above ingredients is intravenously administered to a patient.

The active ingredient above may also be a combination of agents.

GENERAL EXPERIMENTAL PROCEDURES

NMR spectra were recorded on a Varian XL-300 (Varian Co., Palo Alto, Calif.) a Bruker AM-300 spectrometer (Bruker Co., Billerica, Mass.) or a Varian Unity 400 at about 23° C. at 300 or 400 MHz for proton. Chemical shifts are expressed in parts per million downfield from tetramethylsilane. The peak shapes are denoted as follows: s, singlet; d, doublet; t, triplet; q, quartet; m, multiplet; bs, broad singlet. Resonances designated as exchangeable did not appear in a separate NMR experiment where the sample was shaken with several drops of $D_2O$ in the same solvent. Atmospheric pressure chemical ionization mass spectra ($APC_1MS$) were obtained on a Fisons Platform II Spectrometer. Where the intensity of chlorine or bromine-containing ions are described the expected intensity ratio was observed (approximately 3:1 for $^{35}Cl/^{37}Cl$-containing ions and 1:1 for $^{79}Br/^{81}Br$-containing ions) and M is based on $^{35}Cl$ and $^{79}Br$. In some cases only representative $^1H$ NMR and APCIMS peaks are given.

Column chromatography was performed with either Baker Silica Gel (40 μm) (J. T. Baker, Phillipsburg, N.J.) or Silica Gel 60 (EM Sciences, Gibbstown, N.J.) in glass columns or in Flash 40™ or Flash 1 $_2$TM (Biotage) (Charlottesville, Va.) columns under low nitrogen pressure. Rotary Chromatography was performed using a Chromatron (Harrison Research, Palo Alto, Calif.). Unless otherwise specified, reagents were used as obtained from commercial sources. Dimethylformamide, 2-propanol, tetrahydrofuran, and dichloromethane used as reaction solvents were the anhydrous grade supplied by Aldrich Chemical Company (Milwaukee, Wis.). Microanalyses were performed by Schwarzkopf Microanalytical Laboratory, Woodside, N.Y. The terms "concentrated" and "coevaporated" refer to removal of solvent at water aspirator pressure on a rotary evaporator with a bath temperature of less than 50° C. Reactions conducted at "0–20° C." or "0–25° C." were conducted with initial cooling of the vessel in an insulated ice bath which was allowed to warm to room temperature over several hours. The abbreviations "min" and "h" stand for "minutes" and "hours" respectively.

Reference to the hydrochloride salt in the Example names below includes mono-or di-salts as appropriate in the particular Example.

EXAMPLE 1

Example 1A

2-Chloro-5-[4-(3,4-dichloro-phenyl)-1H-imidazol-2-yl]-pyridine:

Lithium hexamethyldisilazide (41.5 mL of a 1.0 M solution in THF) was added to a solution of 2-chloro-5-cyanopyridine (5.24 g) in THF (10 mL). The resultant mixture was stirred at room temperature for 30 min, and then 13 mL saturated aqueous sodium bicarbonate and 5 mL water were added to the reaction mixture. A solution of 3,4-dichlorophenacyl bromide (10.13 g) in chloroform (150 mL) was added in two portions approximately 15 min apart. The resultant mixture was stirred for 72 hours, and the reaction mixture was filtered. The filter cake was triturated with dichloromethane (50 mL) to provide 2-Chloro-5-[4-(3,4-dichloro-phenyl)-1H-imidazol-2-yl]-pyridine (10.46 g). MS m/z 324 ($M^+$), 326 ($M^+$+2).

Alternate Example 1A

2-Chloro-5-[4-(3,4-dichloro-phenyl)-1H-imidazol-2-yl]-pyridine.

A 1.0 M NaHMDS solution in THF (7.94 mL, 7.94 mmol) was added dropwise to a suspension of 2-Chloro-5-cyanopyrinde (1.00 g, 7.22 mmol) in 4 mL of anhydrous THF under $N_2$ at −30° C. The reaction mixture was stirred at −30° C. for 1 hour, was quenched at −30° C. with $KHCO_3/H_2O$ (2.2 g/4 mL), and was allowed to warm to ambient temperature. The reaction mixture was then heated to a vigorous reflux, and 3,4-dichlorophenacyl bromide (1.74 g, 6.50 mmol, 0.9 eq) in THF (8 mL) was added dropwise, keeping the reaction mixture at reflux. After 45 min at reflux, the reaction mixture was cooled to room temp. and 20 mL of EtOAc was added. The layers were separated, and the organic phase was washed with water (10 mL) and brine solution (10 mL), dried over $Na_2SO_4$, and concentrated in vacuo to give a dark brown residue. This was triturated in hot IPE (20 mL) for 10 min, and filtered. The filter cake was rinsed with additional 10 mL IPE. The solids collected were triturated once more using the same protocol to give 1.30 g of 2-Chloro-5-[4(3,4-dichloro-phenyl)-1H-imidazol-2-yl]-pyridine.

Example 1B

1-{5-[4-(3,4-dichloro-phenyl)-1H-imidazol-2-yl]-pyridin-2-yl}-piperazine:

A solution of 2-Chloro-5-[4-(3,4-dichloro-phenyl)-1H-imidazol-2-yl]-pyridine (72.8 g) and piperazine (61.8 g) in DMSO (478 mL) was heated to 105 degrees 16 hours. The reaction mixture was cooled to room temperature and diluted with 2500 mL half-saturated brine. The resultant precipitate was collected by filtration and triturated with 2000 mL hot methanol. The solids were collected by filtration, the mother liquor was concentrated to about 100 mL, and the additional precipitate was collected and combined with the original solids to provide 1-{5-[4-(3,4-dichloro-phenyl)-1H-imidazol-2-yl]-pyridin-2-yl}-piperazine (49 g).

MS m/z 374 ($M^+$+1).

Alternate Example 1B 1-{5-[4-(3,4-dichloro-phenyl)-1H-imidazol-2-yl]-pyridin-2-yl}-4-isobutyl-piperazine.

A suspension of 2-chloro-5-[4-(3,4-dichloro-phenyl)-1H-imidazol-2-yl]-pyridine dihydrochloride (1.07 g, 2.6 mmol), N-isobutylpiperazine (0.95 g, 6.72 mmol), potassium carbonate (0.5 g, 3.62 mmol), and potassium iodide (0.5 g, 0.54 mmol) in xylenes (5 mL) was heated to reflux under a nitrogen atmosphere for 24 hours. The reaction mixture was then cooled to ambient temperature and a solution of potassium carbonate (19) in water (10 mL) and cyclohexane (10 mL) were added. The mixture was stirred vigorously for 15 min, and the precipitate was collected by filtration. The filter cake was washed with water (10 mL) and triturated with methyl tert-butyl ether (4 mL) to provide 1-{5-[5(3,4-dichloro-phenyl)-1H-imidazol-2-yl]-pyridin-2-yl}-4-isobutyl-piperazine (2.07 mmol).

MS m/z 430 ($M^+$+1).

Examples 2–61 were prepared in a manner analogous to the sequence of reactions described for Example 1 as appropriate, employing the appropriate starting materials.

Example 2
5-(4-Phenyl-1H-imidazol-2-yl)-2-pyrrolidin-1-yl-pyridine.
MS m/z 291 (M$^+$+1).

Example 3
5'-4-Phenyl-1H-imidazol-2-yl)-3,4,5,6-tetrahydro-2H-[1,2']bipyridinyl.
MS m/z 304 (M$^+$+1).

Example 4
5-(4-Phenyl-1H-imidazol-2-yl)-3,4,5,6-tetrahydro-2H-[1,2']bipyridinyl-4-ol.
MS m/z 321 (M$^+$+1).

Example 5
{4-{5-[4-Phenyl-1H-imidazol-2-yl)-pyridin-2-yl]-piperazin-1-yl}-acetic acid ethyl ester.
MS m/z 392 (M$^+$+1).

Example 6
Dimethyl-(2-{4-[5-(4-phenyl-1H-imidazol-2-yl)-pyridin-2-yl]-piperazin-1-yl}-ethyl)-amine.
MS m/z 377 (M$^+$+1).

Example 7
2-(4-yl}-4-[4-(3,4-Dichloro-phenyl)-1H-imidazol-2-yl]-pyridin-2-yl}-piperazin-1-yl)-ethanol.
MS m/z 418 (M$^+$).

Example 8
5'-(4-Phenyl-1H-imidazol-2-yl)-4-pyrrolidin-1-yl-3,4,5,6-tetrahydro-2H-[1,2']bipyridinyl.
MS m/z 374 (M$^+$+1).

Example 9
{1-[5-(4-Phenyl-1H-imidazol-2-yl)-pyridin-2-yl]-pyrrolidin-3-yl}-carbamic acid tert-butyl ester.
MS m/z 406 (M$^+$+1).

Example 10
(1-{4-[4-(3,4-Dichloro-phenyl)-1H-imidazol-2-yl]-pyridin-2-yl}-pyrrolidin-3-yl)-carbamic acid tert-butyl ester.
MS m/z 474 (M$^+$).

Example 11
{4'-[4-(3,4-Dichloro-phenyl)-1H-imidazol-2-yl]-3,4,5,6-tetrahydro-2H-[1,2]bipyridinyl-3-yl}methanol.
MS m/z 403 (M$^+$).

Example 12
1-{-4-[4-(3,4-Dichloro-phenyl)-1H-imidazol-2-yl]-pyridin-2-yl}-pyrrolidin-3-ol.
MS m/z 375 (M$^+$).

Example 13
4'-[4-(3,4-Dichloro-phenyl)-1H-imidazol-2-yl]-3,4,5,tetrahydro-2H-[1,2']bipyridinyl-4-ol.
MS m/z 389 (M$^+$).

Example 14
(1-{4-[4-(3,4-Dichloro-phenyl)-1H-imidazol-2-yl]-pyridin-2-yl}-pyrrolidin-2-yl)-methanol.
MS m/z 389 (M$^+$).

Example 15
2-{4'-[4-(3,4-Dichloro-phenyl)-1H-imidazol-2-yl]-3,4,5,6-tetrahydro-2H-[1,2']bipyridinyl-4-yl}-ethanol.
MS m/z 417 (M$^+$).

Example 16
(1-{5-[4-(3,4-Dichloro-phenyl)-1H-imidazol-2-yl]-pyridin-2-yl}-pyrrolidin-2-yl)-methanol.
MS m/z 389 (M$^+$).

Example 17
1-{5-[4-(3,4-Dichloro-phenyl)-1H-imidazol-2-yl]-pyridin-2-yl}-pyrrolidin-3-ol.
MS m/z 375 (M$^+$).

Example 18
1-{5-[4-(4-Chloro-phenyl)-1H-imidazol-2-yl]-pyridin-2-yl}-piperazine.
MS m/z 340 (M$^+$).

Example 19
1-Ethyl-4-{5-[4-(4-trifluoromethyl-phenyl)-1H-imidazol-2-yl]-pyridin-2-yl}-piperazine.
MS m/z 402 (M$^+$+1).

Example 20
1-{5-[4-(2-Chloro-phenyl)-1H-imidazol-2-yl]-pyridin-2-yl}-4-ethyl-piperazine.
MS m/z 354 (M$^+$+1).

Example 21
1-Ethyl-4-{5-[4-(3-trifluoromethyl-phenyl)-1H-imidazol-2-yl]-pyridin-2-yl}-piperazine.
MS m/z 402 (M$^+$+1).

Example 22
4''-[4-(3,4-Difluoro-phenyl)-1H-imidazol-2-yl]-3,4,5,6,3',4,5',6'-octahydro-2H,2'H-[1,4';1',2'']terpyridine.
MS m/z 424 (M$^+$+1).

Example 23
4'-[4-(3,4-Difluoro-phenyl)-1H-imidazol-2-yl]-4-pyrrolidin-1-yl-3,4,5,6-tetrahydro-2H-[1,2']bipyridinyl.
MS m/z 410 (M$^+$+1).

Example 24
4-[2-(4-{4-[4-(3,4-Difluoro-phenyl)-1H-imidazol-2-yl]-pyridin-2-yl}-piperazin-1-yl)-ethyl]-morpholine.
MS m/z 455 (M$^+$+1).

Example 25
1-{5-[4-(3-Chloro-4-fluoro-phenyl)-1H-imidazol-2-yl]-pyridin-2-yl}-4-ethyl-piperazine.
MS m/z 396 (M$^+$+1).

Example 26
1-{5-[4-(2,3-Dichloro-phenyl)-1H-imidazol-2-yl]-pyridin-2-yl}-4-ethyl-piperazine.
MS m/z 402 (M$^+$+1).

Example 27
4-[5-(4-Phenyl-1H-imidazol-2-yl)-pyridin-2-yl]-morpholine.
MS m/z 307 (M$^+$+1).

Example 28
1-[5-(4-Phenyl-1H-imidazol-2-yl)-pyridin-2-yl]-piperazine.
MS m/z 306 (M$^+$+1).

Example 29
1-Methyl-4-[5-(4-phenyl-1H-imidazol-2-yl)-pyridin-2-yl]-piperazine.
MS m/z 320 (M$^+$+1).

Example 30
1-Ethyl-4-{5-[4-phenyl-1H-imidazol-2-yl)-pyridin-2-yl}-piperazine.
MS m/z 334 (M$^+$+1).

Example 31
1-Benzyl-4-[5-(4-phenyl-1H-imidazol-2-yl)-pyridin-2-yl]-piperazine.
MS m/z 396 (M$^+$+1).

Example 32
2-{4-[5-(4-Phenyl-1H-imidazol-2-yl)-pyridin-2-yl]-piperazin-1-yl}-ethanol.
MS m/z 350 (M$^+$+1).

Example 33
1-{5-[4-(3-Fluoro-4-methoxy-phenyl)-1H-imidazol-2-yl]-pyridin-2-yl}-piperazine.
MS m/z 354 (M$^+$+1).

Example 34
1-Ethyl-4-{5-[4-(3-fluoro-4-methoxy-phenyl)-1H-imidazol-2-yl]-pyridin-2-yl}-piperazine.
MS m/z 382 (M$^+$+1).

Example 35
1-{5-[4-(3,4-Dimethoxy-phenyl)-1H-imidazol-2-yl]-pyridin-2-yl}-piperazine.
MS m/z 366 (M$^+$+1).

Example 36
4-{2-[6-(4-Ethyl-piperazin-1-yl)-pyridin-3-yl]-1H-imidazol-4-yl}-benzonitrile.
MS m/z 359 (M$^+$+1).

Example 37
1-{5-[4-(3,4-Dichloro-phenyl)-1H-imidazol-2-yl]-pyridin-2-yl}-4-ethyl-piperazine.
MS m/z 402 (M$^+$+1).

Example 38
1-{5-[4-(4-Fluoro-phenyl)-1H-imidazol-2-yl]-pyridin-2-yl}-piperazine.
MS m/z 324 (M$^+$+1).

Example 39
2-(4-{5-[4-(4-Trifluoromethoxy-phenyl)-1H-imidazol-2-yl]-pyridin-2-yl}-piperazin-1-yl)-ethanol.
MS m/z 434 (M$^+$+1).

Example 40
2-(4-{5-[4-(4-Fluoro-phenyl)-1H-imidazol-2-yl]-pyridin-2-yl}-piperazin-1-yl)-ethanol.
MS m/z 368 (M$^+$+1).

Example 41
1-{5-[4-(4-Trifluoromethoxy-phenyl)-1H-imidazol-2-yl]-pyridin-2-yl}-piperazine.
MS m/z 390 (M$^+$+1).

Example 42
1-Ethyl-4-{5-[4-(4-trifluoromethoxy-phenyl)-1H-imidazol-2-yl]-pyridin-2-yl}-piperazine.
MS m/z 418 (M$^+$+1).

Example 43
1-Ethyl-4-{5-[4-(4-fluoro-phenyl)-1H-imidazol-2-yl]-pyridin-2-yl}-piperazine.
MS m/z 252 (M$^+$+1).

Example 44
1-[5-(4-Benzofuran-2-yl-1H-imidazol-2-yl)-pyridin-2-yl]-4-ethyl-piperazine.
MS m/z 374 (M$^+$+1).

Example 45
2-(4-{5-[4-(3,4-Dichloro-phenyl)-1H-imidazol-2-yl]-pyridin-2-yl}-piperazin-1-yl)-ethanol.
MS m/z 418 (M$^+$+1).

Example 46
1-{5-[4-(3,4-Dichloro-phenyl)-1H-imidazol-2-yl]-pyridin-2-yl}-4-phenyl-piperazine.
MS m/z 450 (M$^+$+1).

Example 47
1-{5-[4-(3,4-Dimethoxy-phenyl)-1H-imidazol-2-yl]-pyridin-2-yl}-4-ethyl-piperazine.
MS m/z 394 (M$^+$+1).

Example 48
2-(4-{5-[4-(3,4-Dimethoxy-phenyl)-1H-imidazol-2-yl]-pyridin-2-yl}-piperazin-1-yl)-ethanol.
MS m/z 410 (M$^+$+1).

Example 49
(1-{5-[4-(3,4-Dichloro-phenyl)-1H-imidazol-2-yl]-pyridin-2-yl}-pyrrolidin-3-yl)-carbamic acid tert-butyl ester.
MS m/z 474 (M$^+$+1).

Example 50
{5'-[4-(3,4-Dichloro-phenyl)-1H-imidazol-2-yl]-3,4,5,6-tetrahydro-2H-[1,2']bipyridinyl-4-yl}-carbamic acid tert-butyl ester.
MS m/z 488 (M$^+$+1).

Example 51
5'-[4-(3,4-Dichloro-phenyl)-1H-imidazol-2-yl]-3,4,5,6-tetrahydro-2H-[1,2']bipyridinyl-4-ol.
MS m/z 389 (M$^+$+1).

Example 52
5'-[4-(3,4-Dichloro-phenyl)-1H-imidazol-2-yl]-3,4,5,6-tetrahydro-2H-[1,2']bipyridinyl-4-ylamine.
MS m/z 388 (M$^+$+1).

Example 53
1-{5-[4-(4-Chloro-phenyl)-1H-imidazol-2-yl]-pyridin-2-yl}-4-ethyl-piperazine.
MS m/z 368 (M$^+$+1).

Example 54
1-{5-[4-(4-Chloro-phenyl)-1H-imidazol-2-yl]-pyridin-2-yl}-4-methyl-piperazine.
MS m/z 354 (M$^+$+1).

Example 55
1-{5-[4-(3-Chloro-phenyl)-1H-imidazol-2-yl]-pyridin-2-yl}-4-methyl-piperazine.
MS m/z 354 (M$^+$+1).

Example 56
1-{5-[4-(3-Chloro-phenyl)-1H-imidazol-2-yl]-pyridin-2-yl}-4-ethyl-piperazine.
MS m/z 368 (M$^+$+1).

Example 57
1-{5-[4-(4-Fluoro-phenyl)-1H-imidazol-2-yl]-pyridin-2-yl}-4-methyl-piperazine.
MS m/z 337 (M$^+$+1).

Example 58
1-{4-[4-(3,4-Dichlorophenyl)-1H-imidazol-2-yl]-pyridin-2-yl}-piperazine.
MS m/z 374 (M$^+$+1).

Example 59
{5'-[4-(3,4-Dichloro-phenyl)-1H-imidazol-2-yl]-3,4,5,6-tetrahydro-2H-[1,2']bipyridinyl-3-yl}-methanol.
MS m/z 403 (M$^+$+1).

Example 60
2-{5'-[4-(3,4-Dichloro-phenyl)-1H-imidazol-2-yl]-3,4,5,6-tetrahydro-2H-f[1,2]bipyridinyl-4-yl}-ethanol.
MS m/z 417 (M$^+$+1).

Example 61
(1-{5-[4-(3,4-Dichloro-phenyl)-1H-imidazol-2-yl]-pyridin-2-yl}-pyrrolidin-2-yl)-methanol.
MS m/z 389 (M$^+$+1).

Example 62
1-{5-[4-(3,4,-dichloro-phenyl)-1H-imidazol-2-yl]-pyridin-2-yl}-4-isobutyl-piperazine:

Sodium triacetoxyborohydride (20.2 g) was added to a suspension of 1-{5-[4-(3,4-dichloro-phenyl)-1H-imidazol-2-yl]-pyridin-2-yl}-piperazine (23.8 g), acetic acid (5.1 mL), and isobutyraldehyde (6.35 mL) in THF (250 mL). The resultant suspension was stirred at ambient temperature for 18 hours, and then the reaction mixture was diluted with 1 N NaOH (1000 mL) and ethyl acetate (450 mL). The layers were separated, and the organic phase was diluted with hexanes (1000 mL). The resultant precipitate was collected by filtration, and the mother liquors were concentrated to 400 mL. The second crop of precipitate was collected and combined with the first crop to provide 1-{5-[5(3,4,-dichloro-phenyl)-1H-imidazol-2-yl]-pyridin-2-yl}-4-isobutyl-piperazine (22.5 g).
MS m/z 430 (M$^+$+1).

Examples 62–94 were prepared in a manner analogous to Example 61, employing the appropriate starting materials.

Example 63
Isobutyl-{1-[5-(4-phenyl-1H-imidazol-2-yl)-pyridin-2-yl]-pyrrolidin-3-yl}-amine.
MS m/z 362 (M$^+$+1).

Example 64
(1-{4-[4-(3,4-Dichloro-phenyl)-1H-imidazol-2-yl]-pyridin-2-yl}-pyrrolidin-3-yl)-isobutyl-amine.
MS m/z 430 (M$^+$).

Example 65
1-{5-[4-(3-Chloro-phenyl)-1H-imidazol-2-yl]-pyridin-2-yl}-4-isobutyl-piperazine.
MS M/z 396 (M$^+$+1).

Example 66
1-{4-[4-(4-Chloro-3-methyl-phenyl)-1H-imidazol-2-yl]-pyridin-2-yl}-4-isobutyl-piperazine.
MS m/z 382 (M$^+$+1).

Example 67
1-{5-[4-(4-Fluoro-phenyl)-1H-imidazol-2-yl]-pyridin-2-yl}-4-propyl-piperazine.
MS m/z 366 (M$^+$+1).

Example 68
4-{5-[4-(4-Fluoro-phenyl)-1H-imidazol-2-yl]-pyridin-2-yl}-1-isobutyl-2-methyl-piperazine.
MS m/z 394 (M$^+$+1).

Example 69
4-{5-[4-(4-Fluoro-phenyl)-1H-imidazol-2-yl]-pyridin-2-yl}-4-phenethyl-piperazine.
MS m/z 428 (M$^+$+1).

Example 70
1-{5-[4-(2-Chloro-phenyl)-1H-imidazol-2-yl]-pyridin-2-yl}-4-isobutyl-piperazine.
MS m/z 396 (M$^+$+1).

Example 71
1-{5-[4-(2-Chloro-phenyl)-1H-imidazol-2-yl]-pyridin-2-yl}-4-propyl-piperazine.
MS m/z 382 (M$^+$+1).

Example 72
1-{5-[4-(4-Fluoro-phenyl)-1H-imidazol-2-yl]-pyridin-2-yl}-4-(3-methyl-but-2-enyl)-piperazine.
MS m/z 392 (M$^+$+1).

Example 73
3-(4-{4-[4-(3-Chloro-phenyl)-1H-imidazol-2-yl]-pyridin-2-yl}-piperazin-1-yl)-2-methyl-butan-1-ol.
MS m/z 426 (M$^+$+1).

Example 74
1-{4-[4-(3-Chloro-phenyl)-1H-imidazol-2-yl]-pyridin-2-yl}-4-(1.2-dimethyl-butyl)-piperazine.
MS m/z 424 (M$^+$+1).

Example 75
1-{4-[4-(3-Chloro-phenyl)-1H-imidazol-2-yl]-pyridin-2-yl}-4-(1-ethyl-2-methyl-propyl)-piperazine.
MS m/z 424 (M$^+$+1).

Example 76
1-{5-[4-(2,3-Dichloro-phenyl)-1H-imidazol-2-yl]-pyridin-2-yl}-4-isobutyl-piperazine.
MS m/z 430 (M$^+$+1).

Example 77
1-{5-[4-(3-Chloro-4-fluoro-phenyl)-1H-imidazol-2-yl]-pyridin-2-yl}-4-isobutyl-piperazine.
MS m/z 414 (M$^+$+1).

Example 78
1-Cyclobutyl-4-[5-(4-phenyl)-1H-imidazol-2-yl)-pyridin-2-yl]-piperazine.
MS m/z 360 (M$^+$+1).

Example 79
1-Cyclopentyl-4-[5-(4-phenyl-1H-imidazol-2-yl)-pyridin-2-yl]-piperazine.
MS m/z 374 (M$^+$+1).

Example 80
1-Isopropyl-4-[5-(4-phenyl-1H-imidazol-2-yl)-pyridin-2-yl]-piperazine.
MS m/z 348 (M$^+$+1).

Example 81
1-{5-[4-(4-Fluoro-phenyl)-1H-imidazol-2-yl]-pyridin-2-yl}-4-isobutyl-piperazine.
MS m/z 380 (M$^+$+1).

Example 82
1-Cyclopropylmethyl-4-{5-[4-(4-fluoro-phenyl)-1H-imidazol-2-yl]-pyridin-2-yl}-piperazine.
MS m/z 378 (M$^+$+1).

Example 83
1-Isobutyl-4-{5-[4-(4-trifluoromethoxy-phenyl)-1H-imidazol-2-yl]-pyridin-2-yl}-piperazine.
MS m/z 446 (M$^+$+1).

Example 84
1-Cyclopropylmethyl-4-{5-[4-(4-trifluoromethoxy-phenyl)-1H-imidazol-2-yl]-pyridin-2-yl}-piperazine.
MS m/z 444 (M$^+$+1).

Example 85
1-{5-[4-(3,4-dimethoxy-phenyl)-1H-imidazol-2-yl]-pyridin-2-yl}-4-isobutyl-piperazine.
MS m/z 422 (M$^+$+1).

Example 86
1-Cyclohexylmethyl-4-{5-[4-(3,4-dichloro-phenyl)-1H-imidazol-2-yl]-pyridin-2-yl}-piperazine.
MS m/z 471 (M$^+$+1).

Example 87
1-Cyclopropylmethyl-4-{5-[4-(3,4-dichloro-phenyl)-1H-imidazol-2-yl]-pyridin-2-yl}-piperazine.
MS m/z 428 (M$^+$+1).

Example 88
1-Cyclopropylmethyl-4-{5-[4-(3,4-dimethoxy-phenyl)-1H-imidazol-2-yl]-pyridin-2-yl}-piperazine.
MS m/z 420 (M$^+$+1).

Example 89
(1-{5-[4-(3,4-Dichloro-phenyl)-1H-imidazol-2-yl-pyridin-2-yl]-pyrrolidin-3-yl}-isobutyl-amine.
MS m/z 430 (M$^+$+1).

Example 90
1-{5-[4-(4-Chlorophenyl)-1H-imidazol-2-yl]-pyridin-2-yl}-4-isobutyl-piperazine.
MS m/z 396 (M$^+$+1).

Example 91
1-{5-[4-(3,4-Dichloro-phenyl)-1H-imidazol-2-yl]-pyridin-2-yl}-4-methyl-piperazine.
MS m/z 388 (M$^+$+1).

Example 92
1-{5-[4-(3,4-Dichloro-phenyl)-1H-imidazol-2-yl]-pyridin-2-yl}-4-propyl-piperazine.
MS m/z 416 (M$^+$+1).

Example 93
1-{5-[4-(3,4-Dichloro-phenyl)-1H-imidazol-2-yl]-pyridin-2-yl}-4-isopropyl-piperazine.
MS m/z 416 (M$^+$+1).

Example 94
1-{5-[4-(3,4-Dichloro-phenyl)-1H-imidazol-2-yl]-pyridin-2-yl}-4-(2,2-dimethyl-propyl)-piperazine.
MS m/z 444 (M$^+$+1).

Example 95
1-Cyclopropyl-4-[5-(4-phenyl-1H-imidazol-2-yl)-pyridin-2-yl]-piperazine:

(Reference: *Tetrahedron Lett.* 1995, 36 (41), 7399) To a solution of 1-[5-(5-phenyl-1H-imidazol-2-yl)-pyridin-2-yl]-piperazine (99 mg, 0.32 mmol) in anhydrous methanol (5 ml) under nitrogen atmosphere was added 3A molecular sieves (50 mg). This solution was stirred for 5 min, then glacial acetic acid (0.19 ml, 200 mg, 3.3 mmol, 10 equiv), (1-ethoxy-cyclopropoxy)-trimethyl-silane (0.32 ml, 281 mg, 1.62 mmol, 5 equiv), and sodium cyanoborohydride (81 mg, 1.29 mmol, 4.0 equiv) were added. The reaction was heated at reflux overnight, then cooled to room temperature. The mixture was filtered, then diluted with an aqueous solution of 1 N NaOH and extracted with ethyl acetate. The combined organics were dried over anhydrous magnesium sulfate, filtered, and concentrated in vacuo to give the desired product (74 mg, 66%).
MS m/z 346 (M$^+$+1).

Examples 96–98 were prepared in a manner analogous to Example 95, employing the appropriate starting materials.

Example 96
1-Cyclopropyl-4-{5-[4-(3-fluoro-4-methoxy-phenyl)-1H-imidazol-2-yl]-pyridin-2-yl}-piperazine.
MS m/z 394 (M$^+$+1).

Example 97
1-Cyclopropyl-4-{5-[4-(4-fluoro-phenyl)-1H-imidazol-2-yl]-pyridin-2-yl}-piperazine.
MS m/z 364 (M$^+$+1).

Example 98
1-Cyclopropyl-4-{5-[4-(4-trifluoromethoxy-phenyl)-1H-imidazol-2-yl]-pyridin-2-yl}-piperazine.
MS m/z 430 (M$^+$+1).

Example 99
2-{4-[5-(4-Phenyl-1H-imidazol-2-yl)-pyridin-2-yl]-piperazin-1-yl}-pyrimidine:

(Reference: *J. Am. Chem. Soc.* 1954, 1484) A solution of 1-[5(5-phenyl-1H-imidazol-2-yl)-pyridin-2-yl]-piperazine (0.16 g, 0.52 mmol), triethylamine (0.22 ml, 0.16 g, 1.58 mmol, 3.0 equiv) and 2-chloro-pyrimidine (0.90 mg, 0.79 mmol, 1.5 equiv) in absolute ethanol (5 ml) under nitrogen atmosphere was heated at reflux for 1 hour, after which additional triethylamine (0.22 ml, 0.16 g, 1.58 mmol, 3.0 equiv) and 2-chloro-pyrimidine (0.90 mg, 0.79 mmol, 1.5 equiv) were added. The reaction was heated at reflux for an additional 1.5 hour, then stirred at room temperature for two days. The mixture was basified to pH 10 with concentrated ammonium hydroxide, and then concentrated in vacuo. The residue was partitioned between water (20 ml) and ethyl acetate (50 ml). The organic phase was dried over anhydrous magnesium sulfate, filtered, and concentrated in vacuo to a solid, which was triturated with ether to give the desired product (0.15 g, 74%). MS m/z 446 (M$^+$+1).

Examples 100–101 were prepared in a manner analogous to the sequence of reactions described for Example 99 as appropriate, employing the appropriate starting materials.

Example 100
1-{5-[4-(3,4-Dichloro-phenyl)-1H-imidazol-2-yl]-pyridin-2-yl}-4-pyridin-2-yl-piperazine.

MS m/z 451 ($M^+$+1).

Example 101
2-(4-{5-[4-(3,4-Dichloro-phenyl)-1H-imidazol-2-yl]-pyridin-2-yl}-piperazin-1-yl)-pyrimidine.

MS m/z 452 ($M^+$+1).

Example 102
1-(4-{5-[4-(3,4-Dichloro-phenyl)-1H-imidazol-2-yl]-pyridin-2-yl}-piperazin-1-yl)-2-methyl-propan-2-ol:

(Reference: *Ind. Acad. Sci.* 1939, 49, 101–4.) A solution of 1-{5-[4-(3,4-dichloro-phenyl)-1H-imidazol-2-yl]-pyridin-2-yl}-piperazine (155 mg, 0.41 mmol), sodium carbonate (66 mg, 0.62 mmol, 1.5 equiv) and 1-chloro-2-methyl-propan-2-ol (51 μl, 53 mg, 0.50 mmol, 1.2 equiv) in 50% aqueous ethanol (20 ml) under nitrogen atmosphere was heated at reflux overnight. The reaction mixture was then diluted with brine and extracted with ethyl acetate (3×25 ml). The combined organic phases were dried over anhydrous magnesium sulfate, filtered, and -concentrated in vacuo. Purification of the residue by flash column chromatography (50% THF/0.5% ammonium hydroxide/hexanes) provided the desired product (100 mg, 54%).

MS m/z 446 ($M^+$+1).

Example 103
(4-{5-[4-(3,4-Dichloro-phenyl)-1H-imidazol-2-yl]-pyridin-2-yl}-piperazin-1-yl)-furan-2-yl-methanone:

To a solution of {5-[4-(3,4-dichloro-phenyl)-1H-imidazol-2-yl]-pyridin-2-yl}-piperazine (150 mg, 0.40 mmol) in chloroform (10 ml) was added 4-dimethylaminopyridine (50 mg, 0.44 mmol, 1.1 equiv), followed by furan-2-carbonyl chloride (40 μl, 53 mg, 0.44 mmol, 1.1 equiv). The reaction was stirred for two days at room temperature. The reaction mixture was then diluted with dichloromethane (10 ml) and extracted with an aqueous solution of saturated sodium bicarbonate (2×10 ml), dried over anhydrous magnesium sulfate, filtered, and concentrated in vacuo. Purification of the residue by flash column chromatography (20% ethyl acetate/hexanes grading to 100% ethyl acetate, then 10% methanol/dichloromethane) provided the desired product (110 mg, 59%).

MS m/z 468 ($M^+$+1).

Examples 104–108 were prepared in a manner analogous to the sequence of reactions described for Example 103 as appropriate, employing the appropriate starting materials.

Example 104
1-(4-{5-[4(3,4-Dichloro-phenyl)-1H-imidazol-2-yl]-pyridin-2-yl}-piperazin-1-yl)-ethanone.

MS m/z 416 ($M^+$+1).

Example 105
(4-{5-[4-(3,4-Dichloro-phenyl)-1H-imidazol-2-yl]-pyridin-2-yl}-piperazin-1-yl)-(2,4-difluoro-phenyl)-methanone.

MS m/z 514 ($M^+$+1).

Example 106
(4-{5-[4-(3,4-Dichloro-phenyl)-1H-imidazol-2-yl]-pyridin-2-yl}-piperazin-1-yl)-phenyl-methanone.

MS m/z 478 ($M^+$+1).

Example 107
(4-{5-[4-(3,4-Dichlorophenyl)-1H-imidazol-2-yl]-pyridin-2-yl}-piperazin-1-yl)-pyridin-3-yl-methanone.

MS m/z 479 ($M^+$+1).

Example 108
1-(4-{5-[4-(3,4-Dichloro-phenyl)-1H-imidazol-2-yl]-pyridin-2-yl}-piperazin-1-yl)-2-(3-methoxy-phenyl)-ethanone.

MS m/z 522 ($M^+$+1).

Example 109
1-{5-[4-(3,4-Dichloro-phenyl)-1H-imidazol-2-yl]-pyridin-2-yl}-pyrrolidin-3-ylamine:

A solution of 1-{5-[5-(3,4-dichloro-phenyl)-1H-imidazol-2-yl]-pyridin-2-yl}-pyrrolidin-3-yl)-carbamic acid tert-butyl ester (0.31 g, 0.66 mmol), 4.0 M HCl/dioxane (0.82 ml, 3.28 mmol, 5.0 equiv), and trifluoroacetic acid (0.50 ml, 0.74 g, 6.49 mmol, 10 equiv) under nitrogen atmosphere was stirred for 5 hours. The reaction mixture was concentrated in vacuo, and the residue was co-evaporated with toluene and triturated with ether to give the desired product (400 mg, 85%) as a tan solid. MS m/z 374 ($M^+$).

Example 110 was prepared in a manner analogous to the sequence of reactions described for Example 109 as appropriate, employing the appropriate starting materials.

Example 110
5'-[4-(3,4-Dichloro-phenyl)-1H-imidazol-2-yl]-3,4,5,6-tetrahydro-2H-[1,2']bipyridinyl-4-ylamine.

MS m/z 388 ($M^+$+1).

Example 111A
2-piperazin-1-yl-isonicotinonitrile:

2-Chloro-isonicotinonitrile (80 g, 0.58 mol) and piperazine (199 g, 2.32 mol, 5 equiv) were combined and heated at 70 DC for 2.5 hours. The resulting suspension was cooled to room temperature and partitioned between a solution of 50% ethyl acetate/dichloromethane and water. The organic phase was separated, and the aqueous phase was extracted with dichloromethane. The combined organic phases were concentrated in vacuo to about half the initial volume and ether was added. The suspension was stirred overnight, then filtered. The solid was dried under vacuum to give the desired product (31 g). The mother liquors were concentrated in vacuo and the residue was triturated with ether and filtered. The solid collected in this second batch was dried under vacuum and combined with the first batch to give the total amount of desired product (46 g, 42%).

MS m/z 189 ($M^+$+1).

Example 111B
2-(4-Isopropyl-piperazin-1-yl)-isonicotinonitrile:

To a solution of 2-piperazin-1-yl-isonicotinonitrile (10 g, 53 mmol), glacial acetic acid (4.26 ml, 4.5 g, 74.4 mmol, 1.4 equiv) and acetone (4.29 ml, 3.39 g, 58 mmol, 1.1 equiv) in anhydrous dichloromethane was added sodium triacetoxyborohydride (13.5 g, 63.8 mmol, 1.2 equiv). The reaction was stirred overnight, then an aqueous solution of 1 N NaOH solution was added (150 ml) and the mixture was extracted once with dichloromethane, then twice with a solution of 10% methanol/dichloromethane. The organic layers were combined, dried over anhydrous sodium sulfate, filtered, and concentrated in vacuo. Purification of the residue by flash column chromatography (5% methanol/$CH_2Cl_2$ grading to 10% methanol/$CH_2Cl_2$) provided the desired product (6.52 g, 59%).

MS m/z 231 ($M^+$+1).

Example 111C

1-{4-[4-(3-Chloro-4-fluoro-phenyl)-1H-imidazol-2-yl]-pyridin-2-yl}-4-isoproplpiperazine:

To a flame-dried flask was added 2-(4-isopropyl-piperazin-1-yl)-isonicotinonitrile (1.09 g, 4.75 mmol) and anhydrous THF (5 ml). To this stirred solution under nitrogen atmosphere was added a 1.0 M solution of lithium bis(trimethylsilyl)amide in tetrahydrofuran (4.75 ml, 1.0 equiv) via syringe. The reaction mixture was stirred at room temperature for 3 hours. Saturated aqueous sodium bicarbonate solution (7.78 ml) was added, followed by water (7.8 ml), $K_2CO_3$ (0.59 g, 4.27 mmol, 0.9 equiv), and a solution of 2-bromo-3'-chloro-4'-fluoroacetophenone (1.19 g, 4.75 mmol, 1.0 equiv) in chloroform (20 ml). After stirring overnight, the aqueous phase was separated and extracted with chloroform. The organic phases were combined, dried over anhydrous magnesium sulfate, filtered, and concentrated in vacuo. The residue was dissolved in glacial acetic acid (10 ml) and heated to 50° C. for 1 hour. The mixture was cooled to room temperature and partitioned between aqueous 1 N NaOH solution and ethyl acetate. The organic phase was removed, and the aqueous phase was saturated with NaCl and extracted again with ethyl acetate. The organic phases were combined, dried over anhydrous magnesium sulfate, filtered, and concentrated in vacuo. Purification of the residue by flash column chromatography ($CH_2Cl_2$ grading to 10% methanol/0.5% ammonium hydroxide/$CH_2Cl_2$) provided the desired product, which was converted to its hydrochloride salt (MeOH/ethereal HCl; 0.92 g).

MS m/z 400 ($M^+$+1).

Examples 112–170 were prepared in a manner analogous to the sequence of reactions described for Example 111A–111C as appropriate, employing the appropriate starting materials.

Example 112

1-{4-[4-(4-Fluoro-phenyl)-1H-imidazol-2-yl]-pyridin-2-yl}-4-isopropyl-piperazine.

MS m/z 366 ($M^+$+1).

Example 113

1-Ethyl-4-{4-[4-(4-fluoro-phenyl)-1H-imidazol-2-yl]-pyridin-2-yl}-piperazine.

MS m/z 352 ($M^+$+1).

Example 114

1-{4-[4-(3-Chloro-4-fluorophenyl)-1H-imidazol-2-yl]-pyridin-2-yl}-4-ethyl-piperazine.

MS m/z 386 ($M^+$+1).

Example 115

1-{4-[4-(4-Chloro-3-methyl-phenyl)-1H-imidazol-2-yl]-pyridin-2-yl}-4-ethyl-piperazine.

MS m/z 382 ($M^+$+1).

Example 116

1-{4-[4-(3-Chloro-phenyl)-1H-imidazol-2-yl]-pyridin-2-yl}-4-isobutyl-piperazine.

MS m/z 396 ($M^+$+1).

Example 117

1-{4-[4-(4-Chloro-phenyl)-1H-imidazol-2-yl]-pyridin-2-yl}-4-isobutyl-piperazine.

MS m/z 396 ($M^+$+1).

Example 118

1-{4-[4-(3,4-difluoro-phenyl)-1H-imidazol-2-yl]-pyridin-2-yl}-4-isobutyl-piperazine.

MS m/z 398 ($M^+$+1).

Example 119

1-{4-[4-(4-Chloro-phenyl)-1H-imidazol-2-yl]-pyridin-2-yl}-4-cyclopropylmethyl-piperazine.

MS m/z 394 ($M^+$+1).

Example 120

1-{4-[4-(3-Chloro-phenyl)-1H-imidazol-2-yl]-pyridin-2-yl}-4-cyclopropylmethyl-piperazine.

MS m/z 394 ($M^+$+1).

Example 121

1-{14-[4-(3,4-Difluoro-phenyl)-1H-imidazol-2-yl]-pyridin-2-yl}-4-cyclopropylmethyl-piperazine.

MS m/z 396 ($M^+$+1).

Example 122

1-{4-[4-(4-Chloro-phenyl)-1H-imidazol-2-yl]-pyridin-2-yl}-4-propyl-piperazine.

MS m/z 382 ($M^+$+1).

Example 123

1-{4-[4-(3-Chloro-phenyl)-1H-imidazol-2-yl]-pyridin-2-yl}-4-propyl-piperazine.

MS m/z 382 ($M^+$+1).

Example 124

1-{4-[4-(4-Fluoro-phenyl)-1H -imidazol-2-yl]-pyridin-2-yl}-4-cyclopropylmethyl-piperazine.

MS m/z 378 ($M^+$+1).

Example 125

1-{4-[4-(3-Chloro-4-fluorophenyl)-1H-imidazol-2-yl]-pyridin-2-yl}-4-cyclopropylmethyl-piperazine.

MS m/z 412 ($M^+$+1).

Example 126

1-{4-[4-(4-Chloro-3-methyl-phenyl)-1H-imidazol-2-yl]-pyridin-2-yl}-4-cyclopropylmethyl-piperazine.

MS m/z 408 ($M^+$+1).

Example 127

1-{4-[4-(4-Fluorophenyl)-1H-imidazol-2-yl]-pyridin-2-yl}-4-cyclopropylethyl-piperazine.

MS m/z 392 ($M^+$+1).

Example 128

1-{4-[4-(3-Chloro-4-fluoro-phenyl)-1H-imidazol-2-yl]-pyridin-2-yl}-4-cyclopropylethyl-piperazine.

MS m/z 426 ($M^+$+1).

Example 129

1-{4-[4-(4-Fluoro-phenyl)-1H-imidazol-2-yl]-pyridin-2-yl}-4-propyl-piperazine.

MS m/z 366 ($M^+$+1).

Example 130

1-{4-[4-(4-Fluoro-phenyl)-1H-imidazol-2-yl]-pyridin-2-yl}-4-isobutyl-piperazine

MS m/z 380 ($M^+$+1).

Example 131

1-{4-[4-(3-Chloro-4-Fluoro-thenyl)-1H-imidazol-2-yl]-pyridin-2-yl}-4-isobutyl-piperazine.

MS m/z 414 (M+1).

Example 132
1-{4-[4-(3,4-Difluoro-phenyl)-1H-imidazol-2-yl]-pyridin-2-yl}-4-cyclopropylethyl-piperazine.
MS m/z 410 (M$^+$+1).

Example 133
1-{4-[4-(3-Chloro-phenyl)-1H-imidazol-2-yl]-pyridin-2-yl}-4-cyclopropyl-piperazine.
MS m/z 380 (M$^+$+1).

Example 134
1-{4-[4-(4-Fluoro-phenyl)-1H-imidazol-2-yl]-pyridin-2-yl}-4-cyclopropyl-piperazine.
MS m/z 364 (M$^+$+1).

Example 135
1-{4-[4-(4-Chloro-3-methyl-phenyl)-1H-imidazol-2-yl]-pyridin-2-yl}-4-isobutyl-piperazine.
MS m/z 410 (M$^+$+1).

Example 136
1-{4-[4-(3-Trifluoromethyl-phenyl)-1H-imidazol-2-yl]-pyridin-2-yl}-4-cyclopropylmethyl-piperazine.
MS m/z 428 (M$^+$+1).

Example 137
1-Cyclopropylmethyl-4-{4-[4-pyridin-2-yl-1H-imidazol-2-yl]-pyridin-2-yl}-piperazine.
MS m/z 361 (M$^+$+1).

Example 138
1-{4-[4-(3-Methoxy-phenyl)-1H-imidazol-2-yl]-pyridin-2-yl}-4-isobutyl-piperazine.
MS m/z 392 (M$^+$+1).

Example 139
3-{2-[2-(4-Cyclopropylmethyl-piperazin-1-yl)-pyridin-4-yl]-1H-imidazol-4-yl}-benzonitrile.
MS m/z 385 (M$^+$+1).

Example 140
3-{2-[2-(4-Isobutyl-piperazin-1-yl)-pyridin-4-yl]-1H-imidazol-4-yl}-benzonitrile.
MS m/z 387 (M$^+$+1).

Example 141
1-{4-[4-(3-Ethyl-phenyl)-1H-imidazol-2-yl]-pyridin-2-yl}-4-cyclopropylmethyl-piperazine.
MS m/z 388 (M$^+$+1).

Example 142
1-{4-[4-(3-Ethyl-phenyl)-1H-imidazol-2-yl]-pyridin-2-yl}-4-isobutyl-piperazine.
MS m/Z 390 (M$^+$+1).

Example 143
1-{4-[4-(3-Trifluoromethoxy-phenyl)-1H-imidazol-2-yl]-pyridin-2-yl}-4-cyclopropylmethyl-piperazine.
MS m/z 446 (M$^+$+1).

Example 144
1-{4-[4-(3-Trifluoromethoxy-phenyl)-1H-imidazol-2-yl]-pyridin-2-yl}-4-isobutyl-piperazine.
MS m/z 446 (M$^+$+1).

Example 145
1-{4-[4-(4-Trifluoromethyl-phenyl)-1H-imidazol-2-yl]-pyridin-2-yl}-4-cyclopropylmethyl-piperazine.
MS m/z 430 (M$^+$+1).

Example 146
1-{4-[4-(3,5-Bis-trifluoromethyl-phenyl)-1H-imidazol-2-yl]-pyridin-2-yl}-4-ethyl-piperazine.
MS m/z 470 (M$^+$+1).

Example 147
1-{4-[4-(3,5-Dichloro-phenyl)-1H-imidazol-2-yl]-pyridin-2-yl}-4-isobutyl-piperazine.
MS m/z 430 (M$^+$).

Example 148
1-{4-[4-(4-Fluoro-3-trifluoromethyl-phenyl)-1H-imidazol-2-yl]-pyridin-2-yl}-4-isobutyl-piperazine.
MS m/z 420 (M$^+$+1).

Example 149
1-{5-[4-(3-Chloro-phenyl)-1H-imidazol-2-yl]-pyridin-2-yl}-4-(2-methoxy-ethyl)-piperazine.
MS m/z 356 (M$^+$+1).

Example 150
1-{5-[4-(3-Trifluoromethyl-phenyl)-1H-imidazol-2-yl]-pyridin-2-yl}-4-(2-methoxy-ethyl)-piperazine.
MS m/z 432 (M$^+$+1).

Example 151
1-{4-[4-(3,5Difluoro-phenyl)-1H-imidazol-2-yl]-pyridin-2-yl}-4-isobutyl-piperazine.
MS m/z 398 (M$^+$+1).

Example 152
1-{5-[4-(4-Fluoro-phenyl)-1H-imidazol-2-yl]-pyridin-2-yl}-4-(2-methoxy-ethyl)-piperazine.
MS m/z 382 (M$^+$+1).

Example 153
1-{4-[4-(3,4-Dichlorophenyl)-1H-imidazol-2-yl]-pyridin-2-yl}-4-ethyl-piperazine.
MS m/z 402 (M$^+$+1).

Example 154
1-{4-[4-(3,4-Dichloro-phenyl)-1H-imidazol-2-yl]-pyridin-2-yl}-4-isobutyl-piperazine.
MS m/z 430 (M$^+$+1).

Example 155
1-Cyclopropylmethyl-4-{4-[4-(3,4-dichloro-phenyl)-1H-imidazol-2-yl]-pyridin-2-yl}-piperazine.
MS n/z 428 (M$^+$+1).

Example 156
1-{4-[4-(3,4-Dichloro-phenyl)-1H-imidazol-2-yl]-pyridin-2-yl}-4-isopropyl-piperazine.
MS Tn/z 416 (M$^+$+1).

Example 157
2-(4-{4-[4-(3,4-Difluoro-phenyl)-1H-imidazol-2-yl]-pyridin-2-yl}-piperazin-1-yl)-ethanol.
MS m/z 386 (M$^+$).

Example 158
2-(4-{4-[4-(4-Fluoro-phenyl)-1H-imidazol-2-yl]-pyridin-2-yl}-piperazin-1-yl)-ethanol.
MS m/z 367 (M$^+$+1).

Example 159
1-{4-[4-(4-Chloro-phenyl)-1H-imidazol-2-yl]-pyridin-2-yl}-4-ethyl-piperazine.
MS m/z 368 (M$^+$+1).

Example 160
1-{4-[4-(3-Chloro-phenyl)-1H-imidazol-2-yl]-pyridin-2-yl}-4-ethyl-piperazine.
MS m/z 368 (M$^+$+1).

Example 161
1-{4-[4-(3,4-Difluoro-phenyl)-1H-imidazol-2-yl]-pyridin-2-yl}-4-ethyl-piperazine.
MS m/z 370 (M$^+$+1).

Example 162
2-(4-{4-[4-(3-Chloro-4-fluoro-phenyl)-1H-imidazol-2-yl]-pyridin-2-yl}-piperazin-1-yl)-ethanol.
MS m/z 402 (M$^+$+1).

Example 163
1-(2,2,2-Trifluoro-ethyl)-4-{4-[4-(3-trifluoromethyl-phenyl)-1H-imidazol-2-yl]-pyridin-2-yl}-piperazin.
MS m/z 456 (M$^+$+1).

Example 164
1-{4-[4-(3-Chloro-phenyl)-1H-imidazol-2-yl]-pyridin-2-yl}-(2,2,2-trifluoro-ethyl)-piperazine.
MS m/z 422 (M$^+$+1).

Example 165
1-{4-[4-(4-Trifluoromethyl-phenyl)-1H-imidazol-2-yl]-pyridin-2-yl}-4-(2,2,2-trifluoro-ethyl)-piperazine.
MS m/z 456 (M$^+$+1).

Example 166
1-{4-[4-(4-Fluoro-phenyl)-1H-imidazol-2-yl]-pyridin-2-yl}-4-(2,2,2-trifluoro-ethyl)-piperazine.
MS m/z 406 (M$^+$+1).

Example 167
1-{4-[4-(4-Trifluoromethyl-phenyl)-1H-imidazol-2-yl]-pyridin-2-yl}-4-(2,2,2-trifluoro-ethyl)-piperazine.
MS m/z 456 (M$^+$+1).

Example 168
1-{4-[4-(3-Trifluoromethyl-phenyl)-1H-imidazol-2-yl]-pyridin-2-yl}-4-(2,2,2-trifluoro-ethyl)-piperazine.
MS m/z 456 (M+1).

Example 169
1-{4-[4-(3-Chloro-phenyl)-1H-imidazol-2-yl]-pyridin-2-yl}-4-(2,2,2-trifluoro-ethyl)-piperazine.
MS m/z 422 (M$^+$+1).

Example 170
1-{4-[4-(4-Chloro-phenyl)-1H-imidazol-2-yl]-pyridin-2-yl}-4-(2,2,2-trifluoro-ethyl)-piperazine.
MS m/z 422 (M$^+$+1).

Example 171
4-{5-[4-(4-Fluoro-phenyl)-1H-imidazol-2-yl]-pyridin-2-yl}-piperazine-1-sulfonic acid dimethylamide:

N,N-Dimethylsulfamoyl chloride (0.09 g) was added to a solution of 1-{5-[4-(4-Fluoro-phenyl)-1H-imidazol-2-yl]-pyridin-2-yl}-piperazine (0.2 g) and pyridine (0.05 g) in THF. The reaction mixture was held at room temperature overnight and then concentrated in vacuo. The residue was diluted with 1 N NaOH and the resultant mixture extracted with dichloromethane. The organics were extracted with 6N HCl, and the acidic extracts basified with 1 N NaOH. The basic aqueous layer was then extracted with dichloromethane. The organics were dried over magnesium sulfate and were concentrated. The residue was purified by flash column chromatography on silica (20% ethyl acetate in hexanes grading to ethyl acetate grading to dichloromethane) to provide 4-{5-[4-(4-Fluoro-phenyl)-1H-imidazol-2-yl]-pyridin-2-yl}-piperazine-1-sulfonic acid dimethylamide (0.11 g).

MS m/z 431 (M$^+$+1).

Examples 172–177 were prepared in a manner analogous to the sequence of reactions described for Example 171 as appropriate, employing the appropriate starting materials.

Example 172
1-{5-[4-(4-Chloro-phenyl)-1H-imidazol-2-yl]-pyridin-2-yl}-4-methanesulfonyl-piperazine.
MS m/z 418 (M$^+$+1).

Example 173
1-{5-[4-(4-Chloro-phenyl)-1H-imidazol-2-yl]-pyridin-2-yl}-4-propanesulfonyl-piperazine.
MS m/z 430 (M$^+$+1).

Example 174
1-{5-[4-(4-Fluoro-phenyl)-1H-imidazol-2-yl]-pyridin-2-yl}-4-phenylmethanesulfonyl-piperazine.
MS m/z 478 (M$^+$+1).

Example 175
1-{5-[4-(4-Fluoro-phenyl)-1H-imidazol-2-yl]-pyridin-2-yl}-4-isopropylsulfonyl-piperazine.
MS m/z 430 (M$^+$+1).

Example 176
1-{5-[4-(4-Fluoro-phenyl)-1H-imidazol-2-yl]-pyridin-2-yl}-4-(toluene-4-sulfonyl)-piperazine.
MS m/z 478 (M$^+$+1).

Example 177
1-{5-[4-(4-Fluoro-phenyl)-1H-imidazol-2-yl]-pyridin-2-yl}-4-(2,2,2-trifluoro-ethanesulfonyl)-piperazine.
MS m/z 470 (M+1).

Example 178
1-{4-[4-(3-Hydroxy-phenyl)-1H-imidazol-2-yl]-pyridin-2-yl}-4-isopropyl-piperazine:

Boron tribromide (25 mL of a 1 M solution in dichloromethane) was added to a solution of 1-{4-[5(3-methoxy-phenyl)-1H-imidazol-2-yl]-pyridin-2-yl}-4-isopropyl-piperazine (1.94 g) in dichloromethane. The resultant yellow suspension was kept at ambient temperature overnight and then quenched by the addition of ice and diluted with water. The resultant mixture was stirred for 30 min and then filtered. The filtrate was extracted with 3N HCl, the solids that had been removed were recombined with the aqueous extracts, and the pH was adjusted to 8 with saturated NaHCO$_3$. The resultant mixture was extracted with 9:1 chloroform/methanol. The combined extracts were concentrated in vacuo, and the residue was concentrated from methanol to provide 1-{4-[5(3-Hydroxy-phenyl)-1H-imidazol-2-yl]-pyridin-2-yl}-4-isopropyl-piperazine (quantitative).

MS m/z 378 (M$^+$+1).

Example 179
1-{4-[4-(3-Isopropoxy-phenyl)-1H-imidazol-2-yl]-pyridin-2-yl}-4-isopropyl-piperazine:

Diethyl azodicarboxylate (0.22 mL) was added via syringe to a solution of 1-{4-[5-(3-Hydroxy-phenyl)-1H-imidazol-2-yl]-pyridin-2-yl}-4-isopropyl-piperazine (304 mg) and triphenylphosphine (0.371 g) in a 1:1 mixture of isopropanol and dichloromethane (13 mL). The resultant solution was stirred at ambient temperature for 3 days and then washed with water. The organic phase was dried over magnesium sulfate and concentrated. The residue was purified by flash column chromatography (5% methanol in dichloromethane) to provide 1-{4-[5-(3-Isopropoxy-phenyl)-1H-imidazol-2-yl]-pyridin-2-yl}-4-isopropyl-piperazine (0.112 g).

MS m/z 420 ($M^+$+1).

Example 180 was prepared in a manner analogous to the sequence of reactions described for Example 179 as appropriate, employing the appropriate starting materials.

Example 180
1-{4-[4-(3-Ethoxy-phenyl)-1H-imidazol-2-yl]-pyridin-2-yl}-4-isopropyl-piperazine.

MS m/z 406 ($M^+$+1).

Example 181
2-(4-{5-[4-(3,4-Dichloro-phenyl)-1H-imidazol-2-yl]-pyridin-2-yl}-piperazin-1-yl)-ethanol; hydrochloride.

A 1N solution of HCl in diethyl ether (0.96 mL, 0.96 mmol) was added via syringe to a solution of 2-(4-{-[5(3,4-Dichloro-phenyl)-1H-imidazol-2-yl]-pyridin-2-yl}-piperazin-1-yl)-ethanol (403 mg, 0.96 mmol) in methanol (10 mL). The resultant solution was stirred for 5 min at ambient temperature and then concentrated to provide 2-(4-{5-[5(3,4-Dichloro-phenyl)-1H-imidazol-2-yl]-pyridin-2-yl}-piperazin-1-yl)-ethanol; hydrochloride (409 mg). MS m/z 418 ($M^+$+1 for free base).

Examples 182–193 were prepared in a manner analogous to Example 181 as appropriate, employing the appropriate starting materials.

Example 182
1-Cyclopropylmethyl-4-{5-[4-(4-fluoro-phenyl)-1H-imidazol-2-yl]-pyridin-2-yl}-piperazine; hydrochloride.

MS m/z 378 ($M^+$+1 of free base).

Example 183
1-{5-[4-(4-Fluoro-phenyl)-1H-imidazol-2-yl]-pyridin-2-yl}-4-isobutyl-piperazine: hydrochloride.

MS m/z 380 ($M^+$+1 of free base).

Example 184
1-{4-[4-(3,4-difluoro-phenyl)-1H-imidazol-2-yl]-pyridin-2-yl}-4-isobutyl-piperazine: hydrochloride.

MS m/z 398 ($M^+$+1 of free base).

Example 185
1-{4-[4-(3-Chloro-4-Fluoro-phenyl)-1H-imidazol-2-yl]-pyridin-2-yl}-4-isobutyl-piperazine; hydrochloride.

MS m/z 414 ($M^+$+1 of free base).

Example 186
3-{2-[2-(4-Isobutyl-piperazin-1-yl)-pyridin-4-yl]-3H-imidazol-4-yl}-benzonitrile; hydrochloride.

MS m/z 387 ($M^+$+1 of free base).

Example 187
1-{4-[4-(3,5-Difluoro-phenyl)-1H-imidazol-2-yl]-pyridin-2-yl}-4-isobutyl-piperazine: hydrochloride.

MS m/z 398 ($M^+$+1 of free base).

Example 188
1-{4-[4-(4-Fluoro-phenyl)-1H-imidazol-2-yl]-pyridin-2-yl}-4-(2,2,2-trifluoro-ethyl)-Piperazine: hydrochloride.

MS m/z 406 ($M^+$+1 of free base).

Example 189
1-{5-[4-(3,4-Dichloro-phenyl)-1H-imidazol-2-yl]-pyridin-2-yl}-isobutyl-piperazine, hydrochloride.

MS m/z 430 ($M^+$+1 of free base).

Example 190
1-{4-[4-(3-Chloro-phenyl)-1H-imidazol-2-yl]-pyridin-2-yl}-4-(2,2,2-trifluoro-ethyl)-piperazine; hydrochloride.

MS m/z 422 ($M^+$+1 of free base).

Example 191
1-Cyclopropylmethyl-4-{5-[4-(3,4-dichloro-phenyl)-1H-imidazol-2-yl]-pyridin-2-yl}-piperazine, hydrochloride.

MS m/z 428 ($M^+$+1 of free base).

Example 192
1-{5-[4-(2-Chloro-phenyl)-1H-imidazol-2-yl]-pyridin-2-yl}-4-ethyl-piperazine: hydrochloride.

MS m/z 354 ($M^+$+1 of free base).

Example 193
1-{5-[4-(4-Chloro-phenyl)-1H-imidazol-2-yl]-pyridin-2-yl}-4-ethyl-piperazine: hyrrochloride.

MS m/z 368 ($M^+$+1 of free base).

What is claimed is:

1. A compound of the Formula I

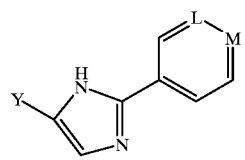

Formula 1 a prodrug thereof, or a pharmaceutically acceptable salt of said compound or of said prodrug;

wherein Y is an aromatic five to eight membered ring optionally having one to two heteroatoms selected independently from oxygen, sulfur and nitrogen or an aromatic bicyclic ring consisting of two fused five to six membered rings, taken independently, optionally having one to four heteroatoms selected independently from nitrogen, sulfur and oxygen;

wherein said Y ring has a maximum of three substituents selected independently from Group 1, Group II and Group III:

Group I: said Y ring is optionally mono-, di-, or tri-substituted independently with nitro, amino, hydroxy, ($C_2$–$C_6$)alkenyl, ($C_1$–$C_4$)alkylthio, halo, cyano, ($C_3$–$C_6$)cycloalkyl($C_1$–$C_6$)alkyl, ($C_3$–$C_6$)cycloalkyl ($C_1$–$C_6$)alkyloxy,($C_1$–$C_6$)alkyl, ($C_3$–$C_6$)cycloalkyl, ($C_1$–$C_6$)alkoxy or ($C_3$–$C_6$)cycloalkoxy, said ($C_3$–$C_6$) cycloalkyl($C_1$–$C_6$)alkyl, ($C_3$–$C_6$)cycloalkyl($C_1$–$C_6$) alkyloxy, ($C_1$–$C_6$)alkyl, ($C_3$–$C_6$)cycloalkyl, ($C_1$–$C_6$) alkoxy and ($C_3$–$C_6$)cycloalkoxy moieties optionally substituted with one to nine fluorines;

Group II: said Y ring is optionally mono-substituted with a four to seven membered saturated nitrogen containing ring optionally having one to two additional heteroatoms selected independently from sulfur, oxygen or nitrogen, said four to seven membered ring optionally mono- or di-substituted independently with $(C_1-C_5)$ alkyl, said $(C_1-C_5)$alkyl optionally substituted with one to nine fluorines; or Group III: said Y ring is optionally mono-, or di-substituted independently with mono-N- or di-N,N-$(C_1-C_6)$alkylamino, mono-N- or di-N,N-$(C_3-C_6)$ cycloalkylamino or N-$(C_1-C_6)$alkyl-N-$(C_3-C_6)$ cycloalkylamino, said mono-N- or di-N,N-$(C_1-C_6)$ alkylamino, mono-N- or di-N,N-$(C_3-C_6)$ cycloalkylamino or N-$(C_1-C_6)$alkyl-N-$(C_3-C_6)$ cycloalkylamino optionally mono-, di-, or tri-substituted independently on each $(C_1-C_6)$alkyl or $(C_3-C_6)$cycloalkyl with $(C_3-C_6)$cycloalkyl, hydroxy, $(C_1-C_3)$alkoxy, $(C_3-C_6)$cycloalkoxy, $(C_3-C_6)$ cycloalkyl$(C_1-C_3)$alkoxy, cyano or fluoro;

L and M are each independently carbon or nitrogen, with the proviso that L and M are not the same, wherein said carbon is bonded to an $R^3$ ring through an $R^3$ ring nitrogen;

wherein $R^3$ is a six to eight membered saturated or partially saturated nitrogen containing ring optionally having one additional heteratom selected independently from sulfur, oxygen or nitrogen;

wherein said additional optional $R^3$ ring nitrogen is optionally mono-substituted with:

1) H or a T ring, optionally linked through $(C_1-C_8)$alkyl or carbonyl wherein said T ring is a partially saturated or fully unsaturated five to eight membered ring optionally having one to two heteroatoms selected independently from oxygen, sulfur and nitrogen or said T ring is a four to seven membered saturated ring having one to two heteroatoms selected independently from sulfur, oxygen or nitrogen or said T ring is an aromatic bicyclic ring consisting of two fused three to six membered rings, taken independently, optionally having one to four heteratoms selected independently from nitrogen, sulfur and oxygen;

wherein said T ring is substituted with a maximum of three substituents selected independently from Group IV, Group V and Group VI:

Group IV: said T ring is optionally mono-, di- or tri-substituted independently with nitro, amino, hydroxy, $(C_2-C_6)$alkenyl, $(C_1-C_4)$alkylthio, halo, cyano, $(C_1-C_6)$alkyl, $(C_3-C_6)$cycloalkyl, $(C_3-C_6)$cycloalkyl $(C_1-C_6)$alkyl, $(C_3-C_6)$cycloalkyl$(C_1-C_6)$alkyloxy, $(C_1-C_6)$alkoxy, $(C_3-C_6)$cycloalkoxy, said $(C_1-C_6)$ alkyl, $(C_3-C_6)$cycloalkyl, $(C_1-C_6)$alkoxy, $(C_3-C_6)$ cycloalkyl$(C_1-C_6)$alkyl, $(C_3-C_6)$cycloalkyl$(C_1-C_6)$ alkyloxy and $(C_3-C_6)$cycloalkoxy moieties optionally substituted with one to nine fluorines;

Group V: said T ring optionally mono- or di-substituted independently with mono-N- or di-N,N-$(C_1-C_6)$ alkylamino, mono-N- or di-N,N-$(C_3-C_6)$ cycloalkylamino or N-$(C_1-C_6)$alkyl-N-$(C_1-C_6)$ cycloalkylamino wherein said mono-N- or di-N,N-$(C_1-C_6)$alkylamino, mono-N- or di-N,N-$(C_3-C_6)$ cycloalkylamino or N-$(C_1-C_6)$alkyl-N-$(C_3-C_6)$ cycloalkylamino is optionally mono-, di-, or tri-substituted independently on each of said $(C_1-C_6)$alkyl or $(C_3-C_6)$cycloalkyl with $(C_3-C_6)$cycloalkyl, hydroxy, $(C_1-C_3)$alkoxy, $(C_1-C_6)$cycloalkoxy, $(C_3-C_6)$ cycloalkyl$(C_1-C_3)$alkoxy, cyano or fluoro;

Group VI: said T ring is optionally mono-substituted with a four to seven membered saturated nitrogen containing ring optionally having one to two additional heteroatoms selected independently from sulfur, oxygen or nitrogen linked to the aromatic T ring through nitrogen, said four to seven membered ring optionally mono-substituted with $(C_1-C_5)$alkyl, said $(C_1-C_5)$alkyl optionally substituted with one to nine fluorines;

2) $(C_1-C_8)$alkyl, $(C_3-C_8)$cycloalkyl or $(C_3-C_8)$cycloalkyl $(C_1-C_8)$alkyl; wherein said $(C_1-C_8)$alkyl, $(C_3-C_8)$ cycloalkyl or $(C_3-C_8)$cycloalkyl$(C_1-C_8)$alkyl is optionally substituted with one to nine fluorines and wherein said $(C_1-C_8)$alkyl, $(C_3-C_8)$cycloalkyl or $(C_3-C_8)$cycloalkyl$(C_1-C_8)$alkyl is optionally substituted with a maximum of three substituents selected independently from Group VII, Group VIII, Group IX and Group X:

Group VII: said $(C_1-C_8)$alkyl, $(C_3-C_8)$cycloalkyl or $(C_3-C_8)$cycloalkyl$(C_1-C_8)$alkyl optionally mono-, di- or tri-substituted independently with mono-N- or di-N, N-$(C_1-C_6)$alkylaminocarbonyl, mono-N- or di-N,N-$(C_3-C_6)$cycloalkylaminocarbonyl, N-$(C_1-C_6)$alkyl-N-$(C_3-C_6)$cycloalkylaminocarbonyl, carboxy, nitro, amino, hydroxy, $(C_2-C_6)$alkenyl, $(C_1-C_4)$alkylthio, halo, cyano, $(C_1-C_6)$alkyl, $(C_3-C_6)$cycloalkyl, $(C_1-C_6)$ alkoxy, or $(C_3-C_6)$cycloalkoxy, said mono-N- or di-N, N-$(C_1-C_6)$alkylaminocarbonyl, mono-N- or di-N,N-$(C_3-C_6)$cycloalkylaminocarbonyl, N-$(C_1-C_6)$alkyl-N-$(C_3-C_6)$cycloalkylaminocarbonyl, $(C_1-C_6)$alkyl, $(C_3-C_6)$cycloalkyl, $(C_1-C_6)$alkoxy, and $(C_3-C_6)$ cycloalkoxy moieties optionally having one to nine fluorines;

Group VIII: said $(C_1-C_8)$alkyl, $(C_3-C_8)$cycloalkyl or $(C_3-C_8)$cycloalkyl$(C_1-C_8)$alkyl optionally mono-substituted with a four to seven membered saturated nitrogen containing ring, linked through a ring nitrogen, said ring optionally having one to two additional heteroatoms selected independently from suflur, oxygen or nitrogen, said four to seven membered ring optionally substituted with $(C_1-C_5)$alkyl, said $(C_1-C_5)$ alkyl optionally substituted with one to nine fluorines;

Group IX: said $(C_1-C_8)$alkyl, $(C_3-C_8)$cycloalkyl or $(C_3-C_8)$cycloalkyl$(C_1-C_8)$alkyl optionally mono-, di- or tri-substituted independently with mono-N- or di-N, N-$(C_1-C_6)$alkylamino, mono-N- or di-N,N-$(C_3-C_6)$ cycloalkylamino or N-$(C_1-C_6)$alkyl-N-$(C_3-C_6)$ cycloalkylamino, said mono-N- or di-N,N-$(C_1-C_6)$ alkylamino, mono-N- or di-N,N-$(C_3-C_6)$ cycloalkylamino or N-$(C_1-C_6)$alkyl-N-$(C_3-C_6)$ cycloalkylamino optionally mono-, di-, or tri-subsfituted independently on each $(C_1-C_6)$alkyl or $(C_3-C_6)$cycloalkyl with $(C_3-C_6)$cycloalkyl, hydroxy, $(C_1-C_3)$alkoxy, $(C_3-C_6)$cycloalkoxy, cyano, or fluoro;

Group X: said $(C_1-C_8)$alkyl, $(C_3-C_8)$cycloalkyl or $(C_3-C_8)$cycloalkyl$(C_1-C_8)$alkyl optionally mono-, di- or tri-substituted independently with $(C_1-C_6)$ alkoxycarbonyl or $(C_1-C_6)$alkylformyl, said $(C_1-C_6)$ alkoxycarbonyl or $(C_1-C_6)$alkylformyl optionally mono-, di- or tri-substituted independently with hydroxy, cyano, fluoro, $(C_1-C_6)$alkyl, $(C_1-C_6)$alkoxy, $(C_3-C_6)$cycloalkyl, $(C_3-C_6)$cycloalkyl$(C_1-C_6)$alkyl, $(C_3-C_6)$cycloalkyl$(C_1-C_6)$alkoxy or $(C_3-C_6)$ cycloalkoxy said $(C_1-C_6)$alkyl, $(C_1-C_6)$alkoxy, $(C_3-C_6)$cycloalkyl, $(C_3-C_6)$cycloalkyl$(C_1-C_6)$alkyl, $C_3-C_6)$cycloalkyl$(C_1-C_6)$alkoxy or $(C_3-C_6)$ cycloalkoxy optionally substituted with one to nine fluorines;

3) $(C_1-C_8)$alkoxycarbonyl, $(C_3-C_8)$cycloalkoxycarbonyl, $(C_3-C_8)$cycloalkyl$(C_1-C_8)$alkoxycarbonyl, $(C_1-C_8)$ alkylformyl, $(C_3-C_8)$cycloalkylformyl or $(C_3-C_8)$ cycloalkyl$(C_1-C_8)$alkylformyl, said $(C_1-C_8)$ alkoxycarbonyl, $(C_3-C_8)$cycloalkoxycarbonyl, $(C_3-C_8)$cycloalkyl$(C_1-C_8)$alkoxycarbonyl, $(C_1-C_8)$ alkylformyl, $(C_3-C_8)$cycloalkylformyl or $(C_3-C_8)$ cycloalkyl$(C_1-C_8)$alkylformyl optionally mono-, di- or tri-substituted independently with hydroxy, cyano, fluoro, $(C_1-C_6)$alkoxy, $(C_1-C_6)$alkyl, $(C_3-C_6)$ cycloalkyl, $(C_3-C_6)$cycloalkyl$(C_1-C_6)$alkyl, $(C_3-C_6)$ cycloalkyl$(C_1-C_6)$alkoxy or $(C_3-C_6)$cycloalkoxy, said $(C_1-C_6)$alkoxy, $(C_1-C_6)$alkyl, $(C_3-C_6)$cycloalkyl, $(C_3-C_6)$cycloalkyl$(C_1-C_6)$alkyl, $(C_3-C_6)$cycloalkyl $(C_1-C_6)$alkoxy or $(C_3-C_6)$cycloalkoxy optionally substituted with from one to nine fluorines;

4) sulfonyl, said sulfonyl optionally mono-substituted with amino, hydroxy, $(C_2-C_8)$alkenyl, $(C_1-C_8)$alkyl, $(C_3-C_8)$cycloalkyl, $(C_1-C_8)$alkoxy, $(C_3-C_8)$ cycloalkoxy, $(C_3-C_8)$cycloalkyl$(C_1-C_8)$alkyl or $(C_3-C_8)$cycloalkyl$(C_1-C_8)$alkyloxy said $(C_2-C_8)$ alkenyl, $(C_1-C_8)$alkyl, $(C_3-C_8)$cycloalkyl, $(C_1-C_8)$ alkoxy, $(C_3-C_8)$cycloalkyl$(C_1-C_8)$alkyl, $(C_3-C_8)$ cycloalkyl$(C_1-C_8)$alkyloxy and $(C_3-C_8)$cycloalkoxy moieties optionally substituted with one to nine fluoros;

or said sulfonyl optionally mono-substituted with mono-N- or di-N,N-$(C_1-C_6)$alkylamino, mono-N- or di-N,N-$(C_3-C_6)$cycloalkylamino or N-$(C_1-C_6)$alkyl-N-$(C_3-C_6)$cycloalkylamino,;

wherein said mono-N- or di-N,N-$(C_1-C_6)$alkylamino, mono-N- or di-N,N-$(C_3-C_6)$cycloalkylamino or N-$(C_1-C_6)$alkyl-N-$(C_3-C_6)$cycloalkylamino is optionally mono-, di-, or tri-substituted independently on each of said $(C_1-C_6)$alkyl or $(C_3-C_6)$cycloalkyl with $(C_3-C_6)$cycloalkyl, hydroxy, $(C_1-C_3)$alkoxy, $(C_3-C_6)$ cycloalkoxy, cyano or fluoro;

or said sulfonyl is optionally monosubstituted with a partially unsaturated or fully unsaturated five to eight membered ring optionally having one to two heteroatoms selected independently from oxygen, sulfur and nitrogen, a four to seven membered saturated ring having one to two heteroatoms selected independently from oxygen, sulfur or nitrogen or an aromatic bicyclic ring consisting of two fused three to six membered rings, taken independently, optionally having one to four heteratoms selected independently from nitrogen, sulfur and oxygen;

wherein said ring is optionally mono-, di-, or tri-substituted independently with nitro, amino, hydroxy, $(C_2-C_6)$alkenyl, $(C_1-C_4)$alkylthio, halo, cyano, $(C_3-C_6)$cycloalkyl$(C_1-C_6)$alkyl, $(C_3-C_6)$cycloalkyl $(C_1-C_6)$alkyloxy, $(C_1-C_6)$alkyl, $(C_3-C_6)$cycloalkyl, $(C_1-C_6)$alkoxy, $(C_3-C_6)$cycloalkoxy, said $(C_3-C_6)$ cycloalkyl$(C_1-C_6)$alkyl, $(C_3-C_6)$cycloalkyl$(C_1-C_6)$ alkyloxy, $(C_1-C_6)$alkyl, $(C_3-C_6)$cycloalkyl, $(C_1-C_6)$ alkoxy and $(C_3-C_6)$cycloalkoxy moieties optionally substituted with one to nine fluorines;

wherein said R ring is optionally mono-, or di-substituted independently on a single carbon or optionally mono-substituted independently on two separate carbons with $R^5$ or $R^8$ wherein $R^5$ and $R^6$ are independently 1) H, carboxy, oxo, amino, halo, cyano, hydroxy, nitro, $(C_2-C_6)$alkenyl, $(C_1-C_4)$alkylthio, $(C_1-C_8)$alkoxy, $(C_3-C_8)$cycloalkoxy, $(C_3-C_8)$cycloalkyl$(C_1-C_8)$ alkoxy, said $(C_1-C_8)$alkoxy, $(C_3-C_8)$cycloalkyl $(C_1-C_8)$alkoxy and $(C_3-C_8)$cycloalkoxy substituents optionally substituted with one to nine fluorines or optionally mono- or di-substituted with hydroxy;

2) mono-N- or di-N,N-$(C_1-C_6)$alkylamino, mono-N- or di-N,N-$(C_3-C_6)$cycloalkylamino or N-$(C_1-C_6)$alkyl-N-$(C_3-C_6)$cycloalkylamino, said mono-N- or di-N,N-$(C_1-C_6)$alkylamino, mono-N- or di-N,N-$(C_3-C_6)$ cycloalkylamino or N-$(C_1-C_6)$alkyl-N-$(C_3-C_6)$ cycloalkylamino optionally mono-, di-, or tri-substituted independently on each $(C_1-C_6)$alkyl or $(C_3-C_6)$cycloalkyl with $(C_3-C_6)$cycloalkyl, hydroxy, $(C_1-C_6)$alkoxy, $(C_3-C_6)$cycloalkoxy, $(C_3-C_6)$ cycloalkyl$(C_1-C_6)$alkoxy, cyano or having one to nine fluorines;

3) $(C_1-C_8)$alkoxycarbonyl, $(C_1-C_8)$cycloalkoxycarbonyl, $(C_3-C_8)$cycloalkyl$(C_1-C_8)$alkoxycarbonyl, $(C_1-C_8)$ alkylformyl, $(C_3-C_8)$cycloalkylformyl or $(C_3-C_8)$ cycloalkyl$(C_1-C_8)$alkylformyl said $(C_1-C_8)$ alkoxycarbonyl, $(C_3-C_8)$cycloalkoxycarbonyl, $(C_3-C_8)$cycloalkyl$(C_1-C_8)$alkoxycarbonyl, $(C_1-C_8)$ alkylformyl, $(C_3-C_8)$cycloalkylformyl or $(C_3-C_8)$ cycloalkyl$(C_1-C_8)$alkylformyl optionally mono-, di- or tri-substituted independently with hydroxy, cyano, fluoro, $(C_1-C_6)$alkoxy or $(C_1-C_6)$alkyl, said$(C_1-C_6)$ alkoxy or $(C_1-C_6)$alkyl optionally substituted with from one to nine fluorines;

4) an X ring, optionally linked through $(C_1-C_8)$alkyl or carbonyl, wherein said X ring is a partially unsaturated or fully unsaturated five to eight membered ring optionally having one to two heteroatoms selected independently from oxygen, sulfur and nitrogen or said X ring is a four to seven membered saturated ring having one to three heteroatoms selected independently from oxygen, sulfur and nitrogen or said X ring is an aromatic bicyclic ring consisting of two fused three to six membered rings, taken independently, optionally having one to four heteroatoms selected independently from nitrogen, sulfur and oxygen; wherein said X ring is optionally substituted with a maximum of three substituents selected independently from Group XI, Group XII or Group XIII Group XI: wherein said X ring is optionally mono-, di- or tri-substituted independently with nitro, amino, hydroxy, $(C_2-C_6)$alkenyl, $(C_1-C_4)$alkylthio, halo, cyano, $(C_1-C_6)$alkyl, $(C_3-C_6)$cycloalkyl, $(C_3-C_6)$ cycloalkyl$(C_1-C_6)$alkyl, $(C_3-C_6)$cycloalkyl$(C_1-C_6)$ alkoxy, $(C_1-C_6)$alkoxy, $(C_3-C_6)$cycloalkoxy, said $(C_1-C_6)$alkyl, $(C_3-C_6)$cycloalkyl, $(C_1-C_6)$alkoxy, $(C_3-C_6)$cycloalkyl$(C_1-C_6)$alkyl, $(C_3-C_6)$cycloalkyl $(C_1-C_6)$alkoxy, and $(C_3-C_5)$cycloalkoxy moieties optionally substituted with one to nine fluorines;

Group XII: said X ring is optionally mono- or di-substituted independently with mono-N- or di-N,N-$(C_1-C_6)$alkylamino, mono-N- or di-N,N-$(C_1-C_6)$ cycloalkylamino or N-$(C_1-C_6)$alkyl-N-$(C_3-C_6)$ cycloalkylamino;

wherein said mono-N- or di-N,N-$(C_1-C_6)$alkylamino, mono-N- or di-N,N-$(C_3-C_6)$cycloalkylamino or N-$(C_1-C_6)$alkyl-N-$(C_3-C_6)$cycloalkylamino is optionally mono-, di-, or tri-substituted independently on each of said $(C_1-C_6)$alkyl or $(C_3-C_6)$cycloalkyl with $(C_3-C_6)$cycloalkyl, hydroxy, $(C_1-C_3)$alkoxy, $(C_3-C_6)$ cycloalkoxy, cyano or fluoro; or Group XIII: said X ring is optionally monosubstituted with a four to seven membered saturated nitrogen containing ring optionally having one to two additional heteroatoms selected independently from sulfur, oxygen or nitrogen linked to the aromatic X ring through nitrogen, said four to seven membered ring optionally substituted with $(C_1-C_5)$alkyl, said $(C_1-C_5)$alkyl optionally substituted with one to nine fluorines;

5) $(C_1-C_8)$alkyl, $(C_3-C_8)$cycloalkyl or $(C_3-C_8)$cycloalkyl$(C_1-C_8)$alkyl, said $(C_1-C_8)$alkyl, $(C_3-C_8)$cycloalkyl or $(C_3-C_8)$cycloalkyl$(C_1-C_8)$alkyl optionally substituted with one to nine fluorines and said $(C_1-C_8)$alkyl, $(C_3-C_8)$cycloalkyl or $(C_3-C_8)$cycloalkyl$(C_1-C_8)$alkyl optionally substituted with a maximum of three substituents selected independently from Group XIV, XV, XVI or XVII; wherein Group XIV: said $(C_1-C_8)$alkyl, $(C_3-C_8)$cycloalkyl $(C_1-C_8)$alkyl or $(C_3-C_8)$cycloalkyl is optionally mono-, di- or tri-substituted independently with mono-N- or di-N,N-$(C_1-C_6)$alkylaminocarbonyl mono-N- or di-N,N-$(C_3-C_6)$cycloalkylaminocarbonyl, N-$(C_1-C_6)$alkyl-N-$(C_3-C_6)$cycloalkylaminocarbonyl, carboxy, nitro, amino, hydroxy, $(C_2-C_6)$alkenyl, $(C_1-C_4)$alkylthio, halo, cyano, $(C_1-C_6)$alkyl, $(C_3-C_6)$cycloalkyl, $(C_1-C_6)$alkoxy, $(C_1-C_6)$cycloalkoxy, $(C_1-C_6)$alkoxycarbonyl, said mono-N- or di-N,N-$(C_1-C_6)$alkylaminocarbonyl, mono-N- or di-N,N-$(C_3-C_6)$cycloalkylaminocarbonyl, N-$(C_1-C_6)$alkyl-N-$(C_3-C_6)$cycloalkylaminocarbonyl, $(C_1-C_6)$alkyl, $(C_3-C_6)$cycloalkyl, $(C_1-C_6)$alkoxy and $(C_3-C_6)$cycloalkoxy moieties optionally substituted with one to nine fluorines;

Group XV: said $(C_1-C_8)$alkyl, $(C_3-C_8)$cycloalkyl or $(C_3-C_8)$cycloalkyl$(C_1-C_8)$alkyl optionally mono-substituted with a four to seven membered saturated nitrogen containing ring, linked through a ring nitrogen, optionally having one to two additional heteroatoms selected independently from sulfur, oxygen or nitrogen, said four to seven membered ring optionally substituted with $(C_1-C_5)$alkyl, said $(C_1-C_5)$alkyl optionally substituted with one to nine fluorines;

Group XVI: said $(C_1-C_8)$alkyl, $(C_3-C_8)$cycloalkyl or $(C_3-C_8)$cycloalkyl$(C_1-C_8)$alkyl optionally mono-, di- or tri-substituted independently with mono-N- or di-N,N-$(C_1-C_6)$alkylamino, mono-N- or di-N,N-$(C_3-C_6)$cycloalkylamino or N-$(C_1-C_6)$alkyl-N-$(C_3-C_6)$cycloalkylamino, said mono-N- or di-N,N-$(C_1-C_6)$alkylamino, mono-N- or di-N,N-$(C_3-C_6)$cycloalkylamino or N-$(C_1-C_6)$alkyl-N-$(C_3-C_6)$cycloalkylamino optionally mono-, di-, or tri-substituted independently on each $(C_1-C_6)$alkyl or $(C_3-C_6)$cycloalkyl with $(C_3-C_6)$cycloalkyl, hydroxy, $(C_1-C_3)$alkoxy, $(C_3-C_6)$cycloalkoxy, cyano or fluoro;

Group XVII: said $(C_1-C_8)$alkyl, $(C_3-C_8)$cycloalkyl or $(C_3-C_8)$cycloalkyl$(C_1-C_8)$alkyl optionally mono-, di- or tri-substituted independently with $(C_1-C_6)$alkoxycarbonyl or $(C_1-C_6)$alkylformyl, said $(C_1-C_6)$alkoxycarbonyl or $(C_1-C_6)$alkylformyl optionally mono-, di- or tri-substituted independently with hydroxy, cyano, fluoro, $(C_1-C_6)$alkyl, $(C_1-C_6)$alkoxy, $(C_3-C_6)$cycloalkyl or $(C_3-C_6)$cycloalkoxy said $(C_1-C_6)$alkyl, $(C_1-C_6)$alkoxy, $(C_3-C_6)$cycloalkyl or $(C_3-C_6)$cycloalkoxy optionally substituted with one to nine fluorines; 6) sulfonyl, said sulfonyl optionally mono-substituted with amino, hydroxy, $(C_2-C_8)$alkenyl, $(C_1-C_8)$alkyl, $(C_3-C_8)$cycloalkyl, $(C_3-C_8)$cycloalkyl$(C_1-C_8)$alkyl, $(C_3-C_8)$cycloalkyl$(C_1-C_8)$alkoxy, $(C_1-C_8)$alkoxy, $(C_3-C_8)$cycloalkoxy, said $(C_2-C_8)$alkenyl, $(C_3-C_8)$cycloalkyl$(C_1-C_8)$alkyl, $(C_3-C_8)$cycloalkyl$(C_1-C_8)$alkoxy, $(C_1-C_8)$alkyl, $(C_3-C_8)$cycloalkyl, $(C_1-C_8)$alkoxy or $(C_3-C_8)$cycloalkoxy moieties optionally substituted with one to nine fluorines or said sulfonyl optionally monosubstituted with mono-N- or di-N,N-$(C_1-C_6)$alkylamino, mono-N- or di-N,N-$(C_3-C_6)$cycloalkylamino or N-$(C_1-C_6)$alkyl-N-$(C_3-C_6)$cycloalkylamino;

wherein said mono-N- or di-N,N-$(C_1-C_6)$alkylamino, mono-N- or di-N,N-$(C_3-C_6)$cycloalkylamino or N-$(C_1-C_6)$alkyl-N-$(C_3-C_6)$cycloalkylamino is optionally mono-, di-, or tri-substituted independently on each of said $(C_1-C_6)$alkyl or $(C_3-C_6)$cycloalkyl with $(C_3-C_6)$cycloalkyl, hydroxy, $(C_1-C_3)$alkoxy, $(C_3-C_6)$cycloalkoxy, cyano or fluoro.

2. A compound as recited in claim 1 wherein

Y is phenyl, benzofuranyl, pyrrolyl or thiophenyl, said Y aromatic rings optionally mono- or di-subsfituted independently with chloro, fluoro, $(C_1-C_4)$alkoxy, hydroxy, $(C_1-C_4)$ alkyl, cyano, trifluoromethyl or trifluoromethoxy;

L is carbon;

M is nitrogen;

$R^3$ is a six to seven membered diaza saturated ring;

$R^3$ is optionally mono-substituted on nitrogen with $(C_1-C_8)$alkyl, $(C_3-C_8)$cycloalkyl or $(C_3-C_8)$cycloalkyl$(C_1-C_8)$alkyl;

wherein said $(C_1-C_8)$alkyl, $(C_3-C_8)$cycloalkyl or $(C_3-C_8)$cycloalkyl$(C_1-C_8)$alkyl are optionally mono- or di-substituted independently with hydroxy and optionally substituted with one to nine fluorines; or $R^3$ is optionally mono-substituted on nitrogen with a carbonyl linked T ring wherein the T ring is phenyl, furanyl or thiophenyl, wherein said ring is optionally mono-, di-, or tri-substituted independently with hydroxy, halo, $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy, said $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy moieties optionally substituted with one to nine fluorines; or $R^3$ is optionally mono-substituted on nitrogen with a five to eight membered aromatic T ring optionally having one or two heteroatoms selected from nitrogen or sulfur, said T ring optionally linked through $(C_1-C_6)$alkyl, wherein said T ring is optionally mono-, di-, or tri-substituted independently with hydroxy, halo, $(C_3-C_6)$cycloalkyl$(C_1-C_6)$alkyl, $(C_3-C_6)$cycloalkyl$(C_1-C_6)$alkoxy, $(C_1-C_6)$alkyl, $(C_3-C_6)$cycloalkyl, $(C_1-C_6)$alkoxy or $(C_3-C_6)$cycloalkoxy;

wherein said $(C_3-C_6)$cycloalkyl$(C_1-C_6)$alkyl, $(C_3-C_6)$cycloalkyl$(C_1-C_6)$alkoxy, $(C_1-C_6)$alkyl, $(C_3-C_6)$cycloalkyl, $(C_1-C_6)$alkoxy or $(C_3-C_6)$cycloalkoxy moieties are optionally substituted with one to nine fluorines;

or a pharmaceutically acceptable salt thereof.

3. A compound as recited in claim 2 wherein $R^3$ is a six membered diaza saturated ring; and $R^3$ is optionally mono-substituted on nitrogen with $(C_1-C_8)$alkyl, $(C_3-C_8)$cycloalkyl or $(C_3-C_8)$cycloalkyl$(C_1-C_8)$alkyl wherein said $(C_1-C_8)$alkyl, $(C_3-C_8)$cycloalkyl or $(C_3-C_8)$cycloalkyl$(C_1-C_8)$alkyl are optionally mono- or di-substituted with hydroxy and optionally substituted with one to nine fluorines; or R³ is optionally mono-substituted on nitrogen with phenyl, said phenyl optionally linked through $(C_1-C_6)$ alkyl, said phenyl optionally mono-, di-, or tri-substituted independently with hydroxy, halo, $(C_3-C_6)$ cycloalkyl$(C_1-C_6)$alkyl, $(C_3-C_6)$cycloalkyl$(C_1-C_6)$ alkoxy,$(C_1-C_6)$alkyl, $(C_3-C_8)$cycloalkyl, $(C_1-C_8)$ alkoxy or $(C_3-C_6)$cycloalkoxy;

wherein said $(C_3-C_6)$cycloalkyl$(C_1-C_6)$alkyl, $(C_3-C_6)$ cycloalkyl$(C_1-C_6)$alkoxy, $(C_1-C_6)$alkyl, $(C_3-C_6)$ cycloalkyl, $(C_1-C_6)$alkoxy or $(C_3-C_6)$cycloalkoxy moieties optionally substituted with one to nine fluorines; or R³ is optionally mono-substituted on nitrogen with pyridyl or pyrimidyl, said pyridyl or pyrimidyl optionally linked through $(C_1-C_6)$alkyl, or a pharmaceutically acceptable salt thereof.

4. A compound as recited in claim 3 wherein

Y is phenyl optionally mono- or di-substituted independently with chloro, fluoro, $(C_1-C_2)$ alkyl, cyano or trifluoromethyl; and R³ is piperazinyl optionally mono-substituted on the nitrogen with $(C_1-C_4)$alkyl, $(C_3-C_6)$cycloalkyl or $(C_3-C_6)$cycloalkyl$(C_1-C_4)$alkyl, said substituents optionally mono-substituted with hydroxy or mono-, di-, or tri-substituted with fluoro, or a pharmaceutically acceptable salt thereof.

5. A compound as recited in claim 4 wherein
Y is 3,4-dichlorophenyl; and
R³ is N-ethylpiperazinyl,
or a pharmaceutically acceptable salt thereof.

6. A compound as recited in claim 4 wherein
Y is 3-chlorophenyl; and
R³ is N-isobutylpiperazinyl,
or a pharmaceutically acceptable salt thereof.

7. A compound as recited in claim 4 wherein
Y is 3,4-difluorophenyl; and
R³ is N-cyclopropylmethylpiperazinyl,
or a pharmaceutically acceptable salt thereof.

8. A compound as recited in claim 4 wherein
Y is 3-chlorophenyl; and
R³ is N-(n-propyl)piperazinyl,
or a pharmaceutically acceptable salt thereof.

9. A compound as recited in claim 4 wherein
Y is 3-chloro,4-fluorophenyl; and
R³ is N-cyclopropylmethylpiperazinyl,
or a pharmaceutically acceptable salt thereof.

10. A compound as recited in claim 4 wherein
Y is 4-chloro-3-methylphenyl; and
R³ is N-cyclopropylmethylpiperazinyl,
or a pharmaceutically acceptable salt thereof.

11. A compound as recited in claim 4 wherein
Y is 3,4-difluorophenyl; and
R³ is N-(2-cyclopropylethyl)-piperazinyl,
or a pharmaceutically acceptable salt thereof.

12. A compound as recited in claim 4 wherein
Y is 3-chloro-4-fluorophenyl; and
R³ is N-isobutylpiperazinyl,
or a pharmaceutically acceptable salt thereof.

13. A compound as recited in claim 4 wherein
Y is 3-chloro-4-fluorophenyl; and
R³ is N-(2-cyclopropylethyl)-piperazinyl,
or a pharmaceutically acceptable salt thereof.

14. A compound as recited in claim 4 wherein
Y is 3-ethylphenyl; and
R³ is N-isobutylpiperazinyl,
or a pharmaceutically acceptable salt thereof.

15. A compound as recited in claim 4 wherein
Y is 3-chlorophenyl; and
R³ is N-2,2,2-trifluoroethylpiperazinyl,
or a pharmaceutically acceptable salt thereof.

16. A compound as recited in claim 4 wherein
Y is 4-trifluoromethylphenyl; and
- is N-isobutylpiperazinyl,
or a pharmaceutically acceptable salt thereof.

17. A compound as recited in claim 4 wherein
Y is 3,5-di-fluorophenyl; and
R³ is N-isobutylpiperazinyl,
or a pharmaceutically acceptable salt thereof.

18. A compound as recited in claim 4 wherein
Y is 3-chlorophenyl; and
R³ is N-(3-hydroxy-1,2-dimethyl-n-propyl)piperazinyl,
or a pharmaceutically acceptable salt thereof.

19. A compound as recited in claim 4 wherein
Y is 3-cyanophenyl; and
R³ is N-isobutylpiperazinyl,
or a pharmaceutically acceptable salt thereof.

20. A compound as recited in claim 4 wherein
Y is 3-cyanophenyl; and
R³ is N-cyclopropylmethylpiperazinyl,
or a pharmaceutically acceptable salt thereof.

21. A compound as recited in claim 1 wherein said compound is
1-{4-[4-(3,4-Dichloro-phenyl)-1H-imidazol-2-yl]-pyridin-2-yl}-4-ethyl-piperazine;
1-{4-[4-(3-Chloro-phenyl)-1H-imidazol-2-yl]-pyridin-2-yl}-4-isobutyl-piperazine;
1-{4-[4-(3,4-Difluoro-phenyl)-1H-imidazol-2-yl]-pyridin-2-yl}-4-cyclopropylmethyl-piperazine;
1-{4-[4-(3-Chloro-phenyl)-1H-imidazol-2-yl]-pyridin-2-yl}-4-propyl-piperazine;
1-{4-[4-(3-Chloro-4-fluoro-phenyl)-1H-imidazol-2-yl]-pyridin-2-yl}-4-cyclopropylmethyl-piperazine;
1-{4-[14-(4-Chloro-3-methyl-phenyl)-1H-imidazol-2-y]-pyridin-2-yl}-4-cyclopropylmethyl-piperazine;
1-{4-[4-(3,4-Difluoro-phenyl)-1H-imidazol-2-yl]-pyridin-2-yl}-4-cyclopropylethyl-piperazine;
1-{4-[4-(3-Chloro-4Fluoro-phenyl)-1H-imidazol-2-yl]-pyridin-2-yl}-4-isobutyl-piperazine; or
the pharmaceutically acceptable salts thereof.

22. A compound as recited in claim 1 wherein said compound is
1-{4-[4-(3-Chloro-4-fluoro-phenyl)-1H-imidazol-2-yl]-pyridin-2-yl}-4-cyclopropylethyl-piperazine;
1-{4-[4-(3-Ethyl-phenyl)-1H-imidazol-2-yl]-pyridin-2-yl}-4-isobutyl-piperazine;
1-{4-[4-(3-Chloro-phenyl)-1H-imidazol-2-yl]-pyridin-2-yl}A-(2,2,2-trifluoro-ethyl)-piperazine;
1-{4-[4-(4-Trifluoromethyl-phenyl)-1H-imidazol-2-yl]-pyridin-2-yl}-4-cyclopropylmethyl-piperazine;
1-{4-[4-(3,5-Difluoro-phenyl)-1H-imidazol-2-yl]-pyridin-2-yl}-4-isobutyl-piperazine;
3-(4-{4-[5-(3-Chloro-phenyl)-1H-imidazol-2-yl]-pyridin-2-yl}-piperazin-1-yl)-2-methyl-butan-1-ol;

3-{2-[2-(4-Isobutyl-piperazin-1-yl)-pyridin-4-yl]-1H-imidazol-4-yl}-benzonitrile; or 3-{2-[2-(4-Cyclopropylmethyl-piperazin-1-yl)-pyridin-4-yl]-1H-imidazol-4-yl}-benzonitrile or the pharmaceutically acceptable salts thereof.

23. A compound as recited in claim 1 wherein

Y is phenyl, benzofuranyl, pyrrolyl or thiophenyl, said Y aromatic rings optionally mono- or di-substituted independently with chloro, fluoro, $(C_1-C_4)$alkoxy, hydroxy, $(C_1-C_4)$ alkyl, cyano, trifluoromethyl or trifluoromethoxy;

L is nitrogen

M is carbon;

$R^3$ is a six to seven membered diaza saturated ring;

$R^3$ is optionally mono-substituted on nitrogen with $(C_1-C_8)$alkyl, $(C_3-C_8)$cycloalkyl or $(C_3-C_8)$cycloalkyl$(C_1-C_8)$alkyl;

wherein said $(C_1-C_8)$alkyl, $(C_3-C_8)$cycloalkyl or $(C_3-C_8)$ cycloalkyl$(C_1-C_8)$alkyl are optionally mono- or di-substituted independently with hydroxy and optionally substituted with one to nine fluorines; or $R^3$ is optionally mono-substituted on nitrogen with a carbonyl linked T ring wherein said T ring is phenyl, furanyl or thiophenyl, wherein said ring is optionally mono-, di-, or tri-substituted independently with hydroxy, halo, $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$ cycloalkoxy, said $(C_1-C_6)$cycloalkyl$(C_1-C_6)$alkyl, $(C_1-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$ cycloalkoxy moieties optionally substituted with one to nine fluorines; or $R^3$ is optionally mono-substituted on nitrogen with a five to eight membered aromatic T ring optionally having one or two heteroatoms selected independently from nitrogen or sulfur, said T ring optionally linked through $(C_1-C_6)$alkyl, wherein said T ring is optionally mono-, di-, or tri-substituted independently with hydroxy, halo, $(C_3-C_6)$cycloalkyl$(C_1-C_6)$alkyl, $(C_3-C_6)$cycloalkyl $(C_1-C_6)$alkoxy, $(C_1-C_6)$alkyl, $(C_3-C_6)$cycloalkyl, $(C_1-C_6)$alkoxy or $(C_3-C_6)$cycloalkoxy;

wherein said $(C_3-C_6)$cycloalkyl$(C_1-C_6)$alkyl, $(C_3-C_6)$ cycloalkyl$(C_1-C_6)$alkoxy, $(C_1-C_6)$alkyl, $(C_3-C_6)$ cycloalkyl, $(C_1-C_6)$alkoxy or $(C_3-C_6)$cycloalkoxy moieties are optionally substituted with one to nine fluorines;

or a pharmaceutically acceptable salt thereof.

24. A compound as recited in claim 23 wherein $R^3$ is a six membered diaza saturated ring; and $R^3$ is optionally mono-substituted on nitrogen with $(C_1-C_8)$alkyl, $(C_3-C_8)$cycloalkyl or $(C_1-C_8)$cycloalkyl $(C_1-C_8)$alkyl wherein said $(C_1-C_8)$alkyl, $(C_3-C_8)$cycloalkyl or $(C_1-C_8)$ cycloalkyl$(C_1-C_8)$alkyl are optionally mono- or di-substituted with hydroxy and optionally substituted with one to nine fluorines; or $R^3$ is optionally mono-substituted on nitrogen with phenyl, said phenyl optionally linked through $(C_1-C_6)$ alkyl, said phenyl optionally mono-, di-, or tri-substituted independently with hydroxy, halo, $(C_3-C_6)$ cycloalkyl$(C_1-C_6)$alkyl, $(C_3-C_6)$cycloalkyl$(C_1-C_6)$ alkoxy, $(C_1-C_6)$alkyl, $(C_3-C_6)$cycloalkyl, $(C_1-C_6)$ alkoxy or $(C_3-C_6)$cycloalkoxy;

wherein said $(C_3-C_6)$cycloalkyl$(C_1-C_6)$alkyl, $(C_3-C_6)$ cycloalkyl$(C_1-C_6)$alkoxy, $(C_1-C_6)$alkyl, $(C_3-C_6)$ cycloalkyl, $(C_1-C_6)$alkoxy or $(C_3-C_6)$cycloalkoxy moieties are optionally substituted with one to nine fluorines; or $R^3$ is optionally mono-substituted on nitrogen with pyridyl or a pyrimidyl ring, said pyridyl or pyrimidyl ring optionally linked through $(C_1-C_6)$alkyl, or a pharmaceutically acceptable salt thereof.

25. A compound as recited in claim 24 wherein

Y is phenyl optionally mono- or di-substituted independently with chloro, fluoro, $(C_1-C_2)$ alkyl, cyano or trifluoromethyl; and $R^3$ is piperazinyl optionally mono-substituted on the nitrogen with $(C_1-C_4)$alkyl, $(C_3-C_6)$cycloalkyl or $(C_1-C_6)$cycloalkyl$(C_1-C_4)$alkyl, said substituents optionally mono-substituted with hydroxy or mono-, di- or tri-substituted with fluoro, or a pharmaceutically acceptable salt thereof.

26. A compound as recited in claim 25 wherein

Y is 4-fluorophenyl; and $R^3$ is N-isobutylpiperazinyl, or a pharmaceutically acceptable salt thereof.

27. A compound as recited in claim 25 wherein

Y is 4-fluorophenyl; and $R^3$ is N-cyclopropylmethylpiperazinyl, or a pharmaceutically acceptable salt thereof.

28. A compound as recited in claim 25 wherein

Y is 3,4-dichlorophenyl; and $R^3$ is N-cyclopropylmethylpiperazinyl, or a pharmaceutically acceptable salt thereof.

29. A compound as recited in claim 25 wherein

Y is 3,4-dichlorophenyl; and $R^3$ is N-isobutylpiperazinyl, or a pharmaceutically acceptable salt thereof.

30. A compound as recited in claim 25 wherein

Y is 4-chlorophenyl; and $R^3$ is N-ethylpiperazinyl, or a pharmaceutically acceptable salt thereof.

31. A compound as recited in claim 25 wherein

Y is 4-chlorophenyl; and $R^3$ is N-isobutylpiperazinyl, or a pharmaceutically acceptable salt thereof.

32. A compound as recited in claim 25 wherein

Y is 3-chlorophenyl; and $R^3$ is N-ethylpiperazinyl, or a pharmaceutically acceptable salt thereof.

33. A compound as recited in claim 25 wherein

Y is 2-chlorophenyl; and $R^3$ is N-ethylpiperazinyl, or a pharmaceutically acceptable salt thereof.

34. A compound as recited in claim 25 wherein

Y is 4-chlorophenyl; and $R^3$ is N-2,2,2-trifluoroethylpiperazinyl, or a pharmaceutically acceptable salt thereof.

35. A compound as recited in claim 25 wherein

Y is 3-chlorophenyl; and $R^3$ is N-2,2,2-trifluoroethylpiperazinyl, or a pharmaceutically acceptable salt thereof.

36. A compound as recited in claim 25 wherein
Y is 4-chlorophenyl; and
R³ is N-2,2,2-trifluoroethylpiperazinyl,
or a pharmaceutically acceptable salt thereof.

37. A compound as recited in claim 25 wherein
Y is 3-chloro-4-fluoro-phenyl; and
R³ is N-ethylpiperazinyl,
or a pharmaceutically acceptable salt thereof.

38. A compound as recited in claim 1 wherein said compound is
1-{5-[4-(4-Fluoro-phenyl)-1H-imidazol-2-yl]-pyridin-2-yl}-4-isobutyl-piperazine;
1-Cyclopropylmethyl-4-{5-[4-(4-fluoro-phenyl)-1H-imidazol-2-yl]-pyridin-2-yl}-piperazine;
1-Cyclopropylmethyl-4-{5-[4-(3,4-dichloro-phenyl)-1H-imidazol-2-yl]-pyridin-2-yl}-piperazine;
1-{5-[4-(3,4-Dichloro-phenyl)-1H-imidazol-2-yl]-pyridin-2-yl}-4-isobutyl-piperazine;
1-{5-[4-(4-Chloro-phenyl)-1H-imidazol-2-yl]-pyridin-2-yl}-4-ethyl-piperazine; or
1-{5-[4-(4-Chloro-phenyl)-1H-imidazol-2-yl]-pyridin-2-yl}-4-isobutyl-piperazine
or the pharmaceutically acceptable salts thereof.

39. A compound as recited in claim 1 wherein said compound is
1-{5-[4-(3-Chloro-phenyl)-1H-imidazol-2-yl]-pyridin-2-yl}-ethyl-piperazine;
1-{5-[4-(2-Chloro-phenyl)-1H-imidazol-2-yl]-pyridin-2-yl}-4-ethyl-piperazine;
1-{4-[4-(4-Fluoro-phenyl)-1H-imidazol-2-yl]-pyridin-2-yl}-4-(2,2,2-trifluoro ethyl)-piperazine;
1-{4-[4(3-Chloro-phenyl)-1H-imidazol-2-yl]-pyridin-2-yl}-4-(2,2,2-trifluoro-ethyl)-piperazine;
1-{4-[4-(4-Chloro-phenyl)-1H-imidazol-2-yl]-pyridin-2-yl}-4-(2,2,2-trifluoro-ethyl)-piperazine; or
1-{5-[4-(3-Chloro-4-fluoro-phenyl)-1H-imidazol-2-yl]-pyridin-2-yl}-4-ethyl-piperazine or the pharmaceutically acceptable salts thereof.

40. A compound as recited in claim 1 wherein
Y is phenyl, benzofuranyl, pyrrolyl or thiophenyl, said Y rings optionally mono- or di-substituted independently with chloro, fluoro, ($C_1$–$C_4$)alkoxy, hydroxy, ($C_1$–$C_4$) alkyl, cyano, trifluoromethyl or trifluoromethoxy;
L is carbon;
M is nitrogen;
R³ is a six membered saturated mono-aza ring optionally substituted on carbon;
R³ is optionally mono- or di-substituted independently with hydroxy, oxo, amino, halo, mono-N- or di-N,N-($C_1$–$C_6$)alkylamino, mono-N- or di-N,N-($C_3$–$C_6$) cycloalkylamino, N-($C_1$–$C_6$)alkyl-N-($C_3$–$C_6$) cycloalkylamino, ($C_1$–$C_8$)alkyl, ($C_3$–$C_8$)cycloalkyl, ($C_3$–$C_8$)cycloalkyl($C_1$–$C_8$)alkyl, ($C_1$–$C_8$)alkoxy, ($C_3$–$C_8$)cycloalkoxy or ($C_3$–$C_8$)cycloalkyl($C_1$–$C_8$) alkoxy;
wherein said mono-N- or di-N,N-($C_1$–$C_6$)alkylamino, mono-N- or di-N,N-($C_3$–$C_6$)cycloalkylamino, N-($C_1$–$C_6$)alkyl-N-($C_3$–$C_6$)cycloalkylamino, ($C_1$–$C_8$) alkyl, ($C_3$–$C_8$)cycloalkyl, ($C_3$–$C_8$)cycloalkyl($C_1$–$C_8$) alkyl, ($C_1$–$C_8$)alkoxy, ($C_3$–$C_8$)cycloalkoxy or ($C_3$–$C_8$) cycloalkyl($C_1$–$C_8$)alkoxy are optionally mono- or di-substituted with hydroxy and optionally substituted with one to nine fluorines; or R³ is optionally mono-substituted with a five to eight membered aromatic X ring optionally having one to two heteroatoms selected independently from nitrogen or sulfur, said X ring optionally linked through ($C_1$–$C_6$) alkyl or carbonyl
wherein said X ring is optionally mono-, di-, or tri-substituted independently with hydroxy, halo, ($C_3$–$C_6$) cycloalkyl($C_1$–$C_6$)alkyl, ($C_3$–$C_6$)cycloalkyl($C_1$–$C_6$) alkoxy, ($C_1$–$C_6$)alkyl, ($C_3$–$C_6$)cycloalkyl, ($C_1$–$C_6$) alkoxy or ($C_3$–$C_6$)cycloalkoxy;
wherein said ($C_3$–$C_6$)cycloalkyl($C_1$–$C_6$)alkyl, ($C_3$–$C_6$) cycloalkyl($C_1$–$C_6$)alkoxy, ($C_1$–$C_6$)alkyl, ($C_3$–$C_6$) cycloalkyl, ($C_1$–$C_6$)alkoxy or ($C_3$–$C_6$)cycloalkoxy moieties are optionally substituted with one to nine fluorines; or
R³ is optionally mono-substituted with a four to seven membered saturated nitrogen containing X ring optionally having one to two additional heteroatoms selected independently from oxygen, nitrogen and sulfur, said ring linked to R³ through N, said link optionally containing a ($C_1$–$C_6$)alkyl,
or a pharmaceutically acceptable salt thereof.

41. A compound as recited in claim 40 wherein
R³ is optionally mono-substituted with hydroxy, amino, halo, mono-N- or di-N,N-($C_1$–$C_6$)alkylamino, ($C_1$–$C_8$) alkoxy, ($C_3$–$C_8$)cycloalkoxy, ($C_1$–$C_8$)alkyl, ($C_4$–$C_8$) cycloalkyl, ($C_3$–$C_8$)cycloalkyl($C_1$–$C_8$)alkoxy or ($C_3$–$C_8$)cycloalkyl($C_1$–$C_8$)alkyl, said mono-N- or di-N, N-($C_1$–$C_6$)alkylamino, ($C_1$–$C_8$)alkoxy, ($C_3$–$C_8$) cycloalkoxy, ($C_1$–$C_8$)alkyl, ($C_3$–$C_8$)cycloalkyl, ($C_3$–$C_8$)cycloalkyl($C_1$–$C_8$)alkoxy or ($C_3$–$C_8$) cycloalkyl($C_1$–$C_8$)alkyl optionally mono- or di-substituted with hydroxy or optionally substituted with one to nine fluorines; or
R³ is optionally mono-substituted with X, wherein X is phenyl, optionally linked through ($C_1$–$C_6$)alkyl or carbonyl, said phenyl optionally mono-, di- or tri-substituted independently with hydroxy, halo, ($C_3$–$C_6$) cycloalkyl($C_1$–$C_6$)alkyl, ($C_3$–$C_6$)cycloalkyl($C_1$–$C_6$) alkoxy,($C_1$–$C_6$)alkyl, ($C_3$–$C_6$)cycloalkyl, ($C_1$–$C_6$) alkoxy or ($C_3$–$C_6$)cycloalkoxy, said ($C_3$–$C_6$)cycloalkyl ($C_1$–$C_6$)alkyl, ($C_3$–$C_6$)cycloalkyl($C_1$–$C_6$)alkoxy, ($C_1$–$C_6$)alkyl, ($C_3$–$C_6$)cycloalkyl, ($C_1$–$C_6$)alkoxy or ($C_3$–$C_6$)cycloalkoxy moieties optionally substituted with one to nine fluorines; or
R³ is optionally mono-substituted with pyridyl or a pyrimidyl X ring, said X ring optionally linked through carbonyl,
or a pharmaceutically acceptable salt thereof.

42. A compound as recited in claim 41 wherein
Y is phenyl, said phenyl optionally mono- or di-substituted independently with chloro, fluoro, ($C_1$–$C_4$)alkoxy, hydroxy, ($C_1$–$C_4$) alkyl, cyano, trifluoromethyl or trifluoromethoxy;
R³ is or piperidinyl;
R³ is optionally mono-substituted with hydroxy, amino, halo, mono-N- or di-N,N-($C_1$–$C_6$)alkylamino, ($C_1$–$C_8$) alkoxy, ($C_3$–$C_8$)cycloalkoxy, ($C_1$–$C_8$)alkyl, ($C_3$–$C_8$) cycloalkyl, ($C_3$–$C_8$)cycloalkyl($C_1$–$C_8$)alkoxy or ($C_3$–$C_8$)cycloalkyl($C_1$–$C_8$)alkyl, said ($C_1$–$C_8$)alkoxy, ($C_3$–$C_8$)cycloalkoxy, ($C_1$–$C_8$)alkyl, ($C_3$–$C_8$)cycloalkyl, ($C_3$–$C_8$)cycloalkyl($C_1$–$C_8$)alkoxy or ($C_3$ –$C_8$) cycloalkyl($C_1$–$C_8$)alkyl optionally mono- or di-substituted with hydroxy or optionally having one to nine fluorines; or
R³ is optionally mono-substituted with phenyl, said phenyl optionally mono-substituted with hydroxy,($C_3$–$C_6$)

cycloalkyl($C_1$–$C_6$)alkyl, ($C_3$–$C_6$)cycloalkyl($C_1$–$C_6$) alkoxy,($C_1$–$C_6$))alkyl, ($C_3$–$C_6$)cycloalkyl, ($C_1$–$C_6$) alkoxy or ($C_3$–$C_6$)cycloalkoxy, said ($C_3$–$C_6$)cycloalkyl ($C_1$–$C_6$)alkyl, ($C_3$–$C_6$)cycloalkyl($C_1$–$C_6$)alkoxy, ($C_1$–$C_6$)alkyl, ($C_3$–$C_6$)cycloalkyl, ($C_1$–$C_6$)alkoxy or ($C_3$–$C_6$)cycloalkoxy moieties optionally substituted with one to nine fluorines, or a pharmaceutically acceptable salt thereof.

43. A compound as recited in claim 42 wherein $R^3$ is or piperidinyl;

$R^3$ is optionally mono-substituted with hydroxy, amino, halo, mono-N- or di-N,N-($C_1$–$C_6$)alkylamino, ($C_1$–$C_8$) alkoxy, ($C_1$–$C_8$)cycloalkoxy, ($C_1$–$C_8$)alkyl, ($C_3$–$C_8$) cycloalkyl, ($C_3$–$C_8$)cycloalkyl($C_1$–$C_8$)alkoxy or ($C_3$–$C_8$)cycloalkyl($C_1$–$C_8$)alkyl, said ($C_1$–$C_8$)alkoxy, ($C_3$–$C_8$)cycloalkoxy, ($C_1$–$C_8$)alkyl, ($C_3$–$C_8$)cycloalkyl, ($C_3$–$C_8$)cycloalkyl($C_1$–$C_8$)alkoxy or ($C_3$–$C_8$) cycloalkyl($C_1$–$C_8$)alkyl optionally mono- or di-substituted with hydroxy or optionally substituted with one to nine fluorines, or a pharmaceutically acceptable salt thereof.

44. A compound as recited in claim 43 wherein

Y is 3,4-di-chlorophenyl; and $R^3$ is 4-hydroxypiperidinyl, or a pharmaceutically acceptable salt thereof.

45. A compound as recited in claim 43 wherein

Y is 3,4-di-chlorophenyl; and $R^3$ is 3-hydroxypiperidinyl, or a pharmaceutically acceptable salt thereof.

46. A compound as recited in claim 1 wherein said compound is

4'-[4-(3,4-Dichloro-phenyl)-1H-imidazol-2-yl]-3,4,5,6-tetrahydro-2H-[1,2]bipyridinyl-4-ol;

2-{4'-[4-(3,4-Dichloro-phenyl)-1H-imidazol-2-yl]-3,4,5,6-tetrahydro-2H-[1,2]bipyridinyl-4-yl}-ethanol; or 1-{4-[4-(3,4-Dichloro-phenyl)-1H-imidazol-2-yl]-pyridin-2-yl}-pyrrolidin-3-ol or the pharmaceutically acceptable salts thereof.

47. A compound as recited in claim 1 wherein

Y is phenyl, benzofuranyl, pyrrolyl or thiophenyl, said Y rings optionally mono- or di-substituted independently with chloro, fluoro, ($C_1$–$C_4$)alkoxy, hydroxy, ($C_1$–$C_4$) alkyl, cyano, trifluoromethyl or trifluoromethoxy;

L is nitrogen;

M is carbon;

$R^3$ is a six membered saturated mono-aza ring optionally substituted on carbon;

$R^3$ is optionally mono- or di-substituted independently with hydroxy, oxo, amino, halo, mono-N- or di-N,N-($C_1$–$C_6$)alkylamino, mono-N- or di-N,N-($C_3$–$C_6$) cycloalkylamino, N-($C_1$–$C_6$)alkyl-N-($C_3$–$C_6$) cycloalkylamino, ($C_1$–$C_8$)alkyl, ($C_3$–$C_8$)cycloalkyl, ($C_3$–$C_8$)cycloalkyl($C_1$–$C_8$)alkyl, ($C_1$–$C_8$)alkoxy, ($C_3$–$C_8$)cycloalkoxy or ($C_3$–$C_8$)cycloalkyl($C_1$–$C_8$) alkoxy;

wherein said mono-N- or di-N,N-($C_1$–$C_6$)alkylamino, mono-N- or di-N,N-($C_3$–$C_6$)cycloalkylamino, N-($C_1$–$C_6$)alkyl-N-($C_3$–$C_6$)cycloalkylamino, ($C_1$–$C_8$) alkyl, ($C_3$–$C_8$)cycloalkyl, ($C_3$–$C_8$)cycloalkyl($C_1$–$C_8$) alkyl, ($C_1$–$C_8$)alkoxy, ($C_3$–$C_8$)cycloalkoxy or ($C_3$–$C_8$) cycloalkyl($C_1$–$C_8$)alkoxy are optionally mono- or di-substituted with hydroxy and optionally substituted with one to nine fluorines; or $R^3$ is optionally mono-subsfituted with a five to eight membered aromatic X ring optionally having one or two heteroatoms selected independently from nitrogen or sulfur, said X ring optionally linked through ($C_1$–$C_6$) alkyl or carbonyl, wherein said X ring is optionally mono-, di-, or tri-substituted independently with hydroxy, halo, ($C_3$–$C_6$) cycloalkyl($C_1$–$C_6$)alkyl, ($C_3$–$C_6$)cycloalkyl($C_1$–$C_6$) alkoxy, ($C_1$–$C_6$)alkyl, ($C_1$–$C_6$)cycloalkyl, ($C_1$–$C_6$) alkoxy or ($C_3$–$C_6$)cycloalkoxy;

wherein said ($C_1$–$C_6$)cycloalkyl($C_1$–$C_6$)alkyl, ($C_3$–$C_6$) cycloalkyl($C_1$–$C_6$)alkoxy, ($C_1$–$C_6$)alkyl, ($C_3$–$C_6$) cycloalkyl, ($C_1$–$C_6$)alkoxy or ($C_3$–$C_6$)cycloalkoxy moieties optionally substituted with one to nine fluorines; or $R^3$ is optionally mono-substituted with a four to seven membered saturated nitrogen containing X ring optionally having one to two additional heteroatoms selected independently from oxygen, nitrogen and sulfur, said ring linked to $R^3$ through N, said link optionally containing a ($C_1$–$C_6$)alkyl, or a pharmaceutically acceptable salt thereof.

48. A compound as recited in claim 47 wherein $R^3$ is optionally mono-substituted with hydroxy, amino, halo, mono-N- or di-N,N-($C_1$–$C_6$)alkylamino, ($C_1$–$C_8$) alkoxy, ($C_3$–$C_8$)cycloalkoxy, ($C_1$–$C_8$)alkyl, ($C_3$–$C_8$) cycloalkyl, ($C_3$–$C_8$)cycloalkyl($C_1$–$C_8$)alkoxy or ($C_3$–$C_8$)cycloalkyl($C_1$–$C_8$)alkyl, said mono-N- or di-N, N-($C_1$–$C_6$)alkylamino, ($C_1$–$C_8$)alkoxy, ($C_3$–$C_8$) cycloalkoxy, ($C_1$–$C_8$)alkyl, ($C_3$–$C_8$)cycloalkyl, ($C_3$–$C_8$)cycloalkyl($C_1$–$C_8$)alkoxy or ($C_3$–$C_8$) cycloalkyl($C_1$–$C_8$)alkyl optionally mono- or di-substituted with hydroxy or optionally substituted with one to nine fluorines; or $R^3$ is optionally mono-substituted with X, wherein X is phenyl, said phenyl optionally mono-, di- or tri-substituted independently with hydroxy, halo, ($C_3$–$C_6$) cycloalkyl($C_1$–$C_6$)alkyl, ($C_3$–$C_6$)cycloalkyl($C_1$–$C_6$) alkoxy,($C_1$–$C_6$)alkyl, ($C_3$–$C_6$)cycloalkyl, ($C_1$–$C_6$) alkoxy or ($C_3$–$C_6$)cycloalkoxy, said ($C_3$–$C_6$)cycloalkyl ($C_1$–$C_6$)alkyl, ($C_3$–$C_6$)cycloalkyl($C_1$–$C_6$)alkoxy, ($C_1$–$C_6$)alkyl, ($C_3$–$C_6$)cycloalkyl, ($C_1$–$C_6$)alkoxy or ($C_3$–$C_6$)cycloalkoxy moieties optionally substituted with one to nine fluorines; or $R^3$ is optionally mono-substituted with a pyridyl or pyrimidyl X ring, said X ring optionally linked through carbonyl, or a pharmaceutically acceptable salt thereof.

49. A compound as recited in claim 48 wherein

Y is phenyl, said phenyl optionally mono- or di-substituted independently with chloro, fluoro, ($C_1$–$C_4$)alkoxy, hydroxy, ($C_1$–$C_4$) alkyl, cyano, trifluoromethyl or trifluoromethoxy;

$R^3$ is or piperidinyl;

$R^3$ is optionally mono-substituted with hydroxy, amino, halo, mono-N- or di-N,N-($C_1$–$C_6$)alkylamino, ($C_1$–$C_6$) alkoxy, ($C_3$–$C_8$)cycloalkoxy, ($C_1$–$C_8$)alkyl, ($C_3$–$C_8$) cycloalkyl, ($C_3$–$C_8$)cycloalkyl($C_1$–$C_8$)alkoxy or ($C_3$–$C_8$)cycloalkyl($C_1$–$C_8$)alkyl, said ($C_1$–$C_8$)alkoxy, ($C_3$–$C_8$)cycloalkoxy, ($C_1$–$C_8$)alkyl, ($C_3$–$C_8$)cycloalkyl, ($C_3$–$C_8$)cycloalkyl($C_1$–$C_8$)alkoxy or ($C_3$–$C_8$) cycloalkyl($C_1$–$C_8$)alkyl optionally mono- or di-substituted with hydroxy or optionally substituted with one to nine fluorines; or $R^3$ is optionally mono-substituted with phenyl, said phenyl optionally mono-substituted with hydroxy,($C_3$–$C_6$) cycloalkyl($C_1$–$C_6$)alkyl, ($C_3$–$C_6$)cycloalkyl($C_1$–$C_6$)

alkoxy,$(C_1-C_6)$alkyl, $(C_3-C_6)$cycloalkyl, $(C_1-C_6)$ alkoxy or $(C_3-C_6)$cycloalkoxy, said $(C_3-C_6)$cycloalkyl $(C_1-C_6)$alkyl, $(C_3-C_6)$cycloalkyl$(C_{12}-C_6)$alkoxy, $(C_1-C_6)$alkyl, $(C_3-C_6)$cycloalkyl, $(C_1-C_6)$alkoxy or $(C_3-C_6)$cycloalkoxy moieties optionally substituted with one to nine fluorines, or a pharmaceutically acceptable salt thereof.

50. A compound as recited in claim 49 wherein $R^3$ is or piperidinyl;

$R^3$ is optionally mono-substituted with hydroxy, amino, halo, mono-N- or di-N,N-$(C_1-C_6)$alkylamino, $(C_1-C_8)$ alkoxy, $(C_3-C_8)$cycloalkoxy, $(C_1-C_8)$alkyl, $(C_3-C_8)$ cycloalkyl, $(C_3-C_8)$cycloalkyl$(C_1-C_8)$alkoxy or $(C_3-C_8)$cycloalkyl$(C_1-C_8)$alkyl, said $(C_1-C_8)$alkoxy, $(C_3-C_8)$cycloalkoxy, $(C_1-C_8)$alkyl, $(C_3-C_8)$cycloalkyl, $(C_3-C_8)$cycloalkyl$(C_1-C_8)$alkoxy or $(C_3-C_8)$ cycloalkyl$(C_1-C_8)$alkyl optionally mono- or di-substituted with hydroxy or optionally substituted with one to nine fluorines, or a pharmaceutically acceptable salt thereof.

51. A compound as recited in claim 50 wherein

Y is 3,4-di-chlorophenyl; and $R^3$ is 4-hydroxypiperidinyl, or a pharmaceutically acceptable salt thereof.

52. A compound as recited in claim 1 wherein said compound is

5'-[4-(3,4-Dichloro-phenyl)-1H-imidazol-2-yl]-3,4,5,6-tetrahydro-2H-[1,2]bipyridinyl-4-ol; or (1-{5-[4-(3,4-Dichloro-phenyl)-1H-imidazol-2-yl]-pyridin-2-yl}-pyrrolidin-3-yl)-isobutyl-amine or the pharmaceutically acceptable salts thereof.

53. A compound as recited in claim 1 wherein

Y is phenyl, benzofuranyl, pyrrolyl or thiophenyl, said Y rings optionally mono- or di-substituted independently with chloro, fluoro, $(C_1-C_4)$alkoxy, hydroxy, $(C_1-C_4)$ alkyl, cyano, trifluoromethyl or trifluoromethoxy;

L is carbon;

M is nitrogen;

$R^3$ is a six to seven membered diaza mono- or di-substituted saturated ring; wherein $R^3$ is optionally mono- or di-substituted independently on carbon with hydroxy, amino, halo, mono-N- or di-N, N-$(C_1-C_6)$alkylamino, mono-N- or di-N,N-$(C_3-C_6)$ cycloalkylamino, N-$(C_1-C_6)$alkyl-N-$(C_3-C_6)$ cycloalkylamino, $(C_1-C_8)$alkyl, $(C_3-C_8)$cycloalkyl, $(C_3-C_8)$cycloalkyl$(C_1-C_8)$alkyl, $(C_1-C_8)$alkoxy, $(C_3-C_8)$cycloalkoxy or $(C_3-C_8)$cycloalkyl$(C_1-C_8)$ alkoxy;

wherein said mono-N- or di-N,N-$(C_1-C_6)$alkylamino, mono-N- or di-N,N-$(C_3-C_6)$cycloalkylamino, N-$(C_1-C_6)$alkyl-N-$(C_3-C_6)$cycloalkylamino, $(C_1-C_8)$ alkyl, $(C_3-C_8)$cycloalkyl, $(C_3-C_8)$cycloalkyl$(C_1-C_8)$ alkyl, $(C_1-C_8)$alkoxy, $(C_3-C_8)$cycloalkoxy or $(C_3-C_8)$ cycloalkyl$(C_1-C_8)$alkoxy are optionally mono- or di-substituted with hydroxy and optionally substituted with one to nine fluorines; or $R^3$ is optionally mono-substituted on carbon with a five to eight membered aromatic X ring optionally having one heteroatom selected from nitrogen or sulfur, said X ring optionally linked through $(C_1-C_6)$alkyl, wherein said X ring is optionally mono-, di-, or tri-substituted independently with hydroxy, halo, $(C_3-C_6)$ cycloalkyl$(C_1-C_6)$alkyl, $(C_3-C_6)$cycloalkyl$(C_1-C_6)$ alkoxy, $(C_1-C_6)$alkyl, $(C_3-C_6)$cycloalkyl, $(C_1-C_6)$ alkoxy or $(C_3-C_6)$cycloalkoxy;

wherein said $(C_3-C_6)$cycloalkyl$(C_1-C_6)$alkyl, $(C_1-C_6)$ cycloalkyl$(C_1-C_6)$alkoxy, $(C_1-C_6)$alkyl, $(C_3-C_6)$ cycloalkyl, $(C_1-C_6)$alkoxy or $(C_1-C_6)$cycloalkoxy moieties are optionally substituted with one to nine fluorines; or $R^3$ is optionally mono-substituted on carbon with an X ring linked through carbonyl, wherein X is phenyl, furanyl or thiophenyl, wherein said X ring is optionally mono-, di-, or tri-substituted independently with hydroxy, halo, $(C_3-C_6)$ cycloalkyl$(C_1-C_6)$alkyl, $(C_1-C_6)$cycloalkyl$(C_1-C_6)$ alkoxy,$(C_1-C_6)$alkyl, $(C_3-C_6)$cycloalkyl, $(C_1-C_6)$ alkoxy or $(C_3-C_6)$cycloalkoxy, said $(C_3-C_6)$cycloalkyl $(C_1-C_6)$alkyl, $(C_3-C_6)$cycloalkyl$(C_1-C_6)$alkoxy, $(C_1-C_6)$alkyl, $(C_3-C_6)$cycloalkyl, $(C_1-C_6)$alkoxy or $(C_3-C_6)$cycloalkoxy moieties optionally substituted with one to nine fluoros; or $R^3$ is optionally mono-substituted on carbon with a four to seven membered saturated nitrogen containing X ring optionally having one to two additional heteroatoms selected independently from oxygen, nitrogen and sulfur, said ring linked to $R^3$ through N, said link optionally containing a $(C_1-C_6)$alkyl; and $R^3$ is optionally mono-substituted on nitrogen with $(C_1-C_8)$alkyl, $(C_3-C_8)$cycloalkyl or $(C_3-C_8)$cycloalkyl $(C_1-C_8)$alkyl;

wherein said $(C_1-C_8)$alkyl, $(C_3-C_8)$cycloalkyl or $(C_3-C_8)$ cycloalkyl$(C_1-C_8)$alkyl are optionally mono- or di-substituted independently with hydroxy and optionally substituted with one to nine fluorines; or $R^3$ is optionally mono-substituted on nitrogen with a carbonyl linked T ring wherein said T ring is phenyl, furanyl or thiophenyl, wherein said ring is optionally mono-, di-, or tri-substituted independently with hydroxy, halo, $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_8)$ cycloalkoxy, said $(C_1-C_6)$cycloalkyl$(C_1-C_6)$alkyl, $(C_3-C_6)$cycloalkyl$(C_1-C_6)$alkoxy,$(C_1-C_6)$alkyl, $(C_3-C_8)$cycloalkyl, $(C_1-C_6)$alkoxy or $(C_3-C_6)$ cycloalkoxy moieties optionally substituted with one to nine fluorines; or $R^3$ is optionally mono-substituted on nitrogen with a five to eight membered aromatic T ring optionally having one or two heteroatoms selected independently from nitrogen or sulfur, said T ring optionally linked through $(C_1-C_6)$alkyl, wherein said T ring is optionally mono-, di-, or tri-substituted independently with hydroxy, halo, $(C_3-C_6)$ cycloalkyl$(C_1-C_6)$alkyl, $(C_3-C_6)$cycloalkyl$(C_1-C_6)$ alkoxy, $(C_1-C_6)$alkyl, $(C_3-C_6)$cycloalkyl, $(C_1-C_6)$ alkoxy or $(C_3-C_6)$cycloalkoxy;

wherein said $(C_3-C_8)$cycloalkyl$(C_1-C_6)$alkyl, $(C_3-C_6)$ cycloalkyl$(C_1-C_6)$alkoxy, $(C_1-C_6)$alkyl, $(C_3-C_6)$ cycloalkyl, $(C_1-C_6)$alkoxy or $(C_3-C_6)$cycloalkoxy moieties are optionally substituted with one to nine fluorines;

or a pharmaceutically acceptable salt thereof.

54. A compound of claim 53 wherein $R^3$ is a six to seven membered diaza saturated ring mono-substituted on carbon;

wherein $R^3$ is optionally mono-substituted with hydroxy, amino, halo, mono-N- or di-N,N-$(C_1-C_6)$alkylamino, $(C_1-C_8)$ alkoxy, $(C_3-C_8)$cycloalkoxy, $(C_1-C_8)$alkyl, $(C_3-C_8)$cycloalkyl, $(C_3-C_8)$cycloalkyl$(C_1-C_8)$alkoxy or $(C_3-C_8)$cycloalkyl$(C_1-C_8)$alkyl, said $(C_1-C_8)$alkoxy, $(C_3-C_8)$cycloalkoxy, $(C_1-C_8)$alkyl, $(C_3-C_8)$cycloalkyl, $(C_3-C_8)$cycloalkyl$(C_1-C_8)$alkoxy or $(C_3-C_8)$cycloalkyl$(C_1-C_8)$alkyl optionally mono- or di-substituted with hydroxy or optionally substituted with one to nine fluorines; or $R^3$ is optionally mono-substituted with phenyl, said phenyl optionally mono-substituted with hydroxy,$(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy, said $(C_3-C_6)$cycloalkyl$(C_1-C_6)$alkyl, $(C_3-C_6)$cycloalkyl$(C_1-C_6)$alkoxy, $(C_1-C_6)$alkyl, $(C_3-C_6)$cycloalkyl, $(C_1-C_6)$alkoxy or $(C_3-C_6)$cycloalkoxy moieties optionally substituted with one to nine fluorines, or a pharmaceutically acceptable salt thereof.

55. A compound of claim 53 wherein $R^3$ is a six to seven membered diaza saturated ring, said ring mono-substituted on carbon and mono-substituted on nitrogen; wherein $R^3$ is optionally mono-substituted on nitrogen with $(C_1—C_8)$alkyl, $(C_3-C_8)$cycloalkyl or $(C_3-C_8)$cycloalkyl$(C_1-C_8)$alkyl wherein said $(C_1-C_8)$alkyl, $(C_3-C_8)$cycloalkyl or $(C_3-C_8)$cycloalkyl$(C_1-C_8)$alkyl are optionally mono-, di- or tri-substituted independently with hydroxy, halo, $(C_1-C_8)$cycloalkyl; or $R^3$ is optionally mono-substituted on nitrogen with phenyl, said phenyl optionally linked through $(C_1-C_6)$alkyl, said phenyl optionally mono-, di- or tri-substituted independently with hydroxy, halo, $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy;

wherein said $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy moieties are optionally substituted with one to nine fluorines; or $R^3$ is optionally mono-substituted on nitrogen with a pyridyl or pyrimidyl ring, said pyridyl or pyrimidyl ring optionally linked through $(C_1-C_6)$alkyl; or $R^3$ is mono-substituted on carbon with hydroxy, amino, halo, mono-N- or di-N,N-$(C_1-C_6)$alkylamino, $(C_1-C_8)$alkoxy, $(C_3-C_8)$cycloalkoxy, $(C_1-C_8)$alkyl, $(C_3-C_8)$cycloalkyl, $(C_3-C_8)$cycloalkyl$(C_1-C_8)$alkoxy or $(C_3-C_8)$cycloalkyl$(C_1-C_8)$alkyl, said $(C_1-C_8)$alkoxy, $(C_3-C_8)$cycloalkoxy, $(C_1-C_8)$alkyl, $(C_3-C_8)$cycloalkyl, $(C_3-C_8)$cycloalkyl$(C_1-C_8)$alkoxy or $(C_3-C_8)$cycloalkyl$(C_1-C_8)$alkyl optionally mono- or di-substituted with hydroxy or optionally substituted with one to nine fluorines, or a pharmaceutically acceptable salt thereof.

56. A compound as recited in claim 1 wherein

Y is phenyl, benzofuranyl, pyrrolyl or thiophenyl, said Y rings optionally mono- or di-substituted independently with chloro, fluoro, $(C_1-C_4)$alkoxy, hydroxy, $(C_1-C_4)$alkyl, cyano, trifluoromethyl or trifluoromethoxy;

L is nitrogen;

M is carbon;

$R^3$ is a six to seven membered diaza mono- or di-substituted saturated ring;

wherein $R^3$ is optionally mono- or di-substituted independently on carbon with hydroxy, amino, halo, mono-N- or di-N,N-$(C_1-C_6)$alkylamino, mono-N- or di-N,N-$(C_3-C_6)$cycloalkylamino, N-$(C_1-C_6)$alkyl-N-$(C_3-C_6)$cycloalkylamino, $(C_1-C_8)$alkyl, $(C_3-C_8)$cycloalkyl, $(C_3-C_8)$cycloalkyl$(C_1-C_8)$alkyl, $(C_1-C_8)$alkoxy, $(C_3-C_8)$cycloalkoxy or $(C_3-C_8)$cycloalkyl$(C_1-C_8)$alkoxy;

wherein said mono-N- or di-N,N-$(C_1-C_6)$alkylamino, mono-N- or di-N,N-$(C_3-C_6)$cycloalkylamino, N-$(C_1-C_6)$alkyl-N-$(C_3-C_6)$cycloalkylamino, $(C_1-C_8)$alkyl, $(C_3-C_8)$cycloalkyl, $(C_3-C_8)$cycloalkyl$(C_1-C_8)$alkyl, $(C_1-C_8)$alkoxy, $(C_3-C_8)$cycloalkoxy or $(C_3-C_8)$cycloalkyl$(C_1-C_8)$alkoxy are optionally mono- or di-substituted with hydroxy and optionally substituted with one to nine fluorines; or $R^3$ is optionally mono-substituted on carbon with a five to eight membered aromatic X ring optionally having one heteroatom selected from nitrogen or sulfur, said X ring optionally linked through $(C_1-C_6)$alkyl, wherein said X ring is optionally mono-, di-, or tri-substituted independently with hydroxy, halo, $(C_3-C_6)$cycloalkyl$(C_1-C_6)$alkyl, $(C_3-C_6)$cycloalkyl$(C_1-C_6)$alkoxy, $(C_1-C_6)$alkyl, $(C_3-C_6)$cycloalkyl, $(C_1-C_6)$alkoxy or $(C_3-C_6)$cycloalkoxy;

wherein said $(C_3-C_6)$cycloalkyl$(C_1-C_6)$alkyl, $(C_3-C_6)$cycloalkyl$(C_1-C_6)$alkoxy, $(C_1-C_6)$alkyl, $(C_3-C_6)$cycloalkyl, $(C_1-C_6)$alkoxy or $(C_3-C_6)$cycloalkoxy moieties are optionally substituted with one to nine fluorines;

$R^3$ is optionally mono-substituted on carbon with an X ring linked through carbonyl, wherein X is phenyl, furanyl or thiophenyl, wherein said X ring is optionally mono-, di-, or tri-substituted independently with hydroxy, halo, $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy, said $(C_3-C_6)$cycloalkyl$(C_1-C_6)$alkyl, $(C_3-C_6)$cycloalkyl$(C_1-C_6)$alkoxy, $(C_1-C_6)$alkyl, $(C_3-C_6)$cycloalkyl, $(C_1-C_6)$alkoxy or $(C_3-C_6)$cycloalkoxy moieties optionally substituted with one to nine fluoros; or $R^3$ is optionally mono-substituted on carbon with a four to seven membered saturated nitrogen containing X ring optionally having one to two additional heteroatoms selected independently from oxygen, nitrogen and sulfur, said ring linked to $R^3$ through N, said link optionally containing a $(C_1-C_6)$alkyl; and $R^3$ is optionally mono-substituted on nitrogen with $(C_1-C_8)$alkyl, $(C_3-C_8)$cycloalkyl or $(C_3-C_8)$cycloalkyl$(C_1-C_8)$alkyl;

wherein said $(C_1-C_8)$alkyl, $(C_1-C_8)$cycloalkyl or $(C_3-C_8)$cycloalkyl$(C_1-C_8)$alkyl are optionally mono- or di-substituted with hydroxy and optionally substituted with one to nine fluorines; or $R^3$ is optionally mono-substituted on nitrogen with a carbonyl linked T ring wherein said T ring is phenyl, furanyl or thiophenyl, wherein said ring is optionally mono-, di-, or tri-substituted independently with hydroxy, halo, $(C_3-C_6)$cycloalkyl$(C_1-C_6)$alkyl, $(C_3-C_6)$cycloalkyl$(C_1-C_6)$alkoxy,$(C_1-C_6)$alkyl, $(C_3-C_6)$cycloalkyl, $(C_1-C_6)$alkoxy or $(C_3-C_6)$cycloalkoxy, said $(C_3-C_6)$cycloalkyl$(C_1-C_6)$alkyl, ($C_3$–$C_6$)cycloalkyl($C_1$–$C_6$)alkoxy,($C_1$–$C_6$)alkyl, ($C_1$–$C_6$)cycloalkyl, ($C_1$–$C_6$)alkoxy or ($C_3$–$C_6$) cycloalkoxy moieties optionally substituted with one to nine fluoros; or $R^3$ is optionally mono-substituted on nitrogen with a five to eight membered aromatic T ring optionally having one or two heteroatoms selected independently from nitrogen or sulfur, said T ring optionally linked through ($C_1$–$C_6$)alkyl, wherein said T ring is optionally mono-, di-, or tri-substituted independently with hydroxy, halo, ($C_3$–$C_6$) cycloalkyl($C_1$–$C_6$)alkyl, ($C_3$ –$C_6$)cycloalkyl($C_1$–$C_6$) alkoxy, ($C_1$–$C_6$)alkyl, ($C_3$–$C_6$)cycloalkyl, ($C_1$–$C_6$) alkoxy or ($C_3$–$C_6$)cycloalkoxy;

wherein said ($C_1$–$C_6$)cycloalkyl($C_1$–$C_6$)alkyl, ($C_3$–$C_6$) cycloalkyl($C_1$–$C_6$)alkoxy, ($C_1$–$C_6$)alkyl, ($C_3$–$C_6$) cycloalkyl, ($C_1$–$C_6$)alkoxy or ($C_3$–$C_6$)cycloalkoxy moieties optionally substituted with one to nine fluorines;

or a pharmaceutically acceptable salt thereof.

57. A compound of claim 56 wherein $R^3$ is a six to seven membered diaza saturated ring mono-substituted on carbon;

wherein $R^3$ is optionally mono-substituted with hydroxy, amino, halo, mono-N- or di-N,N-($C_1$–$C_6$)alkylamino, ($C_1$–$C_8$) alkoxy, ($C_3$–$C_8$)cycloalkoxy, ($C_1$–$C_8$)alkyl, ($C_3$–$C_8$) cycloalkyl, ($C_3$–$C_8$)cycloalkyl($C_1$–$C_8$)alkoxy or ($C_3$–$C_8$)cycloalkyl($C_1$–$C_8$)alkyl, said ($C_1$–$C_8$)alkoxy, ($C_3$–$C_8$)cycloalkoxy, ($C_1$–$C_8$)alkyl, ($C_3$–$C_8$)cycloalkyl, ($C_3$–$C_8$)cycloalkyl($C_1$–$C_8$)alkoxy or ($C_3$–$C_8$) cycloalkyl($C_1$–$C_8$)alkyl optionally mono- or di-substituted with hydroxy or optionally substituted with one to nine fluorines; or $R^3$ is optionally mono-substituted with phenyl, said phenyl optionally mono-substituted with hydroxy,($C_3$–$C_6$) cycloalkyl($C_1$–$C_6$)alkyl, ($C_3$–$C_6$)cycloalkyl($C_1$–$C_6$) alkoxy,($C_1$–$C_6$)alkyl, ($C_3$–$C_6$)cycloalkyl, ($C_1$–$C_6$) alkoxy or ($C_3$–$C_6$)cycloalkoxy, said ($C_3$–$C_6$)cycloalkyl ($C_1$–$C_6$)alkyl, ($C_3$–$C_6$)cycloalkyl($C_1$–$C_6$)alkoxy, ($C_1$–$C_6$)alkyl, ($C_3$–$C_6$)cycloalkyl, ($C_1$–$C_6$)alkoxy or ($C_3$–$C_6$)cycloalkoxy moieties optionally substituted with one to nine fluorines, or a pharmaceutically acceptable salt thereof.

58. A compound of claim 57 wherein $R^3$ is a six to seven membered diaza saturated ring, said ring mono-substituted on carbon and mono-substituted on nitrogen;

wherein $R^3$ is optionally mono-substituted on nitrogen with ($C_1$–$C_8$)alkyl, ($C_3$–$C_8$)cycloalkyl or ($C_3$–$C_8$) cycloalkyl($C_1$–$C_8$)alkyl wherein said ($C_1$–$C_8$)alkyl, ($C_3$–$C_8$)cycloalkyl or ($C_3$–$C_8$) cycloalkyl($C_1$–$C_8$)alkyl are optionally mono-, di- or tri-substituted independently with hydroxy, halo, ($C_1$–$C_6$)cycloalkyl; or $R^3$ is optionally mono-substituted on nitrogen with phenyl, said phenyl optionally linked through ($C_1$–$C_6$) alkyl, said phenyl optionally mono-, di-, or tri-substituted independently with hydroxy, halo, ($C_3$–$C_6$) cycloalkyl($C_1$–$C_6$)alkyl, ($C_3$–$C_6$)cycloalkyl($C_1$—$C_6$) alkoxy,($C_1$–$C_6$)alkyl, ($C_3$–$C_6$)cycloalkyl, ($C_1$–$C_6$) alkoxy or ($C_3$–$C_6$)cycloalkoxy;

wherein said ($C_3$–$C_6$)cycloalkyl($C_1$–$C_6$)alkyl, ($C_3$–$C_6$) cycloalkyl($C_1$–$C_6$)alkoxy,($C_1$–$C_6$)alkyl, ($C_3$–$C_6$) cycloalkyl, ($C_1$–$C_6$)alkoxy or ($C_3$–$C_6$)cycloalkoxy moieties are optionally substituted with one to nine fluorines; or $R^3$ is optionally mono-substituted on nitrogen with a pyridyl or pyrimidyl ring, said pyridyl or pyrimidyl ring optionally linked through ($C_1$–$C_6$)alkyl; and $R^3$ is mono-substituted on carbon with hydroxy, amino, halo, mono-N- or di-N,N-($C_1$–$C_6$)alkylamino, ($C_1$–$C_8$) alkoxy, ($C_3$–$C_8$)cycloalkoxy, ($C_1$–$C_8$)alkyl, ($C_3$–$C_8$) cycloalkyl, ($C_3$–$C_8$)cycloalkyl($C_1$–$C_8$)alkoxy or ($C_3$–$C_8$)cycloalkyl($C_1$–$C_8$)alkyl, said ($C_1$–$C_8$)alkoxy, ($C_3$–$C_8$)cycloalkoxy, ($C_1$–$C_8$)alkyl, ($C_3$–$C_8$)cycloalkyl, (3–$C_8$)cycloalkyl($C_1$–$C_8$)alkoxy or ($C_3$–$C_8$)cycloalkyl ($C_1$–$C_8$)alkyl optionally mono- or di-substituted with hydroxy or optionally substituted with one to nine fluorines, or a pharmaceutically acceptable salt thereof.

59. A compound as recited in claim 58 wherein

Y is 4-fluorophenyl; and $R^3$ is 4-isobutyl-3-methylpiperazinyl;

or a pharmaceutically acceptable salt thereof.

60. A compound as recited in claim 1 wherein said compound is 4-{5-[4-(4-Fluoro-phenyl)-1H-imidazol-2-yl]-pyridin-2-yl}-1-isobutyl-2-methyl-piperazine or the pharmaceutically acceptable salts thereof.

61. A compound having the Formula LXX

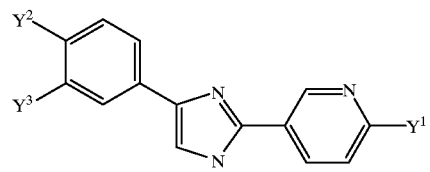

wherein $Y^1$ is piperazinyl or besylate; and $Y_2$ and $Y_3$ are independently H, halo, ($C_1$–$C_6$)alkyl, ($C_3$–$C_6$)cycloalkyl, cyano, ($C_1$–$C_6$)alkoxy, or ($C_3$–$C_6$) cycloalkoxy, said $Y_2$ and $Y_3$ substituents optionally substituted with from one to nine fluorines.

62. A compound as recited in claim 61 wherein $Y^1$ is piperazinyl; and $Y^2$ and $Y^3$ are chloro.

63. A compound as recited in claim 61 wherein $Y^1$ is piperazinyl; and $Y^2$ is chloro and $Y^3$ is fluoro.

64. A compound as recited in claim 61 wherein $Y^1$ is piperazinyl; and $Y^2$ is H and $Y^3$ is cyano.

65. A method of treating obesity comprising administering to a mammal in need of such treatment a therapeutically effective amount of a compound of claim 1 or a prodrug thereof or a pharmaceutically acceptable salt of said compound or of said prodrug.

66. A method as recited in claim 65 wherein the amount of the Formula I compound is about 0.01 mg/kg/day to about 50 mg/kg/day.

67. A method as recited in claim 66 wherein the mammal is a female or male human.

68. A pharmaceutical composition which comprises a therapeutically effective amount of a compound of claim 1 or a prodrug thereof or a pharmaceutically acceptable salt of said compound or of said prodrug and a pharmaceutically acceptable carrier, vehicle or diluent.

69. A pharmaceutical composition for the treatment of obesity which comprises an obesity treating amount of a compound of claim 1 or a prodrug thereof or a pharmaceutically acceptable salt of said compound or of said prodrug and a pharmaceutically acceptable carrier, vehicle or diluent.

70. A pharmaceutical combination composition comprising: a therapeutically effective amount of a composition comprising a first compound, said first compound being a compound of claim 1, a prodrug thereof, or a pharmaceutically acceptable salt of said compound or of said prodrug;

a second compound, said second compound being a 3 agonist, a thyromimetic agent, an eating behavior modifying agent, or a NPY antagonist; and a pharmaceutical carrier, vehicle or diluent.

71. A method of treating obesity comprising administering to a mammal in need of such treatment an amount of a first compound, said first compound being a compound of claim 1, a prodrug thereof, or a pharmaceutically acceptable salt of said compound or of said prodrug;

an amount of a second compound, said second compound being a 3 agonist, a thyromimetic agent, an eating behavior modifying agent, or a NPY antagonist;

wherein the amounts of the first and second compounds result in a therapeutic effect.

72. A kit comprising:

a. a first compound, said first compound being a compound of claim 1, a prodrug thereof, or a pharmaceutically acceptable salt of said compound or of said prodrug and a pharmaceutically acceptable carrier, vehicle or diluent in a first unit dosage form;

b. a second compound, said second compound being a $\beta_3$ agonist, a thyromimetic agent, an eating behavior modifying agent, or a NPY antagonist and a pharmaceutically acceptable carrier, vehicle or diluent in a second unit dosage form; and c. means for containing said first and second dosage forms wherein the amounts of first and second compounds result in a therapeutic effect.

73. A pharmaceutical combination composition comprising: a therapeutically effective amount of a composition comprising a first compound, said first compound being a compound of claim 1, a prodrug thereof, or a pharmaceutically acceptable salt of said compound or of said prodrug;

a second compound, said second compound being an aldose reductase inhibitor, a glycogen phosphorylase inhibitor, a sorbitol dehydrogenase inhibitor, insulin, metformin, acarbose, a thiazolidinedione, a glitazone, rezulin, troglitazone, a sulfonylurea, glipazide, glyburide, or chlorpropamide; and a pharmaceutical carrier, vehicle or diluent.

74. A pharmaceutical composition as recited in claim 79 wherein the aldose reductase inhibitor is 1-phthalazineacetic acid, 3,4-dihydro-4-oxo-3-[[5-trifluoromethyl)-2-benzothiazolyl]methyl]- or a pharmaceutically acceptable salt thereof.

* * * * *

UNITED STATES PATENT AND TRADEMARK OFFICE
CERTIFICATE OF CORRECTION

PATENT NO. : 6,355,635 B1
DATED : March 12, 2002
INVENTOR(S) : Richard L. Elliott, Richard F. Hank and Marlys Hammond It is certified that error appears in the above-identified patent and that said Letters Patent is hereby corrected as shown below:

Column 102,
Line 25, the claim reference numeral "79" should read -- 73 --.

Signed and Sealed this

Twenty-second Day of July, 2003

JAMES E. ROGAN
*Director of the United States Patent and Trademark Office*